US010221408B2

(12) United States Patent
Okhamafe et al.

(10) Patent No.: US 10,221,408 B2
(45) Date of Patent: Mar. 5, 2019

(54) COMPOSITIONS OF PROKARYOTIC PHENYLALANINE AMMONIA-LYASE VARIANTS AND METHODS OF USING COMPOSITIONS THEREOF

(71) Applicant: BioMarin Pharmaceutical Inc., Novato, CA (US)

(72) Inventors: Augustus O. Okhamafe, Concord, CA (US); Sean M. Bell, Novato, CA (US); G. Nick Zecherle, Novato, CA (US); Kris Antonsen, San Rafael, CA (US); Yanhong Zhang, San Rafael, CA (US); Kieu Ly Tran, San Francisco, CA (US); Paul A. Fitzpatrick, Berkeley, CA (US); Emil D. Kakkis, San Rafael, CA (US); Michel Claude Vellard, San Rafael, CA (US); Daniel J. Wendt, Walnut Creek, CA (US); Mubarack Muthalif, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 15/130,694

(22) Filed: Apr. 15, 2016

(65) Prior Publication Data

US 2016/0362675 A1    Dec. 15, 2016

Related U.S. Application Data

(63) Continuation of application No. 13/576,625, filed as application No. PCT/US2011/023534 on Feb. 3, 2011, now abandoned.

(Continued)

(51) Int. Cl.
*C12N 9/88*        (2006.01)
*C07K 1/00*        (2006.01)
(Continued)

(52) U.S. Cl.
CPC .............. *C12N 9/88* (2013.01); *A61K 9/0019* (2013.01); *A61K 38/51* (2013.01); *A61K 47/60* (2017.08);
(Continued)

(58) Field of Classification Search
None
See application file for complete search history.

(56) References Cited

U.S. PATENT DOCUMENTS

| 4,252,822 A | 2/1981 | Berry |
| 4,562,151 A | 12/1985 | Kishore |

(Continued)

FOREIGN PATENT DOCUMENTS

| EP | 0 167 411 A2 | 7/1985 |
| WO | WO 1990/12874 | 11/1990 |

(Continued)

OTHER PUBLICATIONS

Branden et al. Introduction to Protein Structure, Garland Publishing Inc., New York, p. 247, 1991.*

(Continued)

*Primary Examiner* — Yong D Pak
(74) *Attorney, Agent, or Firm* — Jones Day

(57) ABSTRACT

Provided herein are phenylalanine ammonia-lyase (PAL) variants produced by prokaryotes, wherein such prokaryotic PAL variant has a greater phenylalanine-converting activity and/or a reduced immunogenicity as compared to a wild-type PAL. Further provided are compositions of prokaryotic PAL and biologically active fragments, mutants, variants or analogs thereof, as well as methods for the production, purification, formulation, and use of such compositions for industrial and therapeutic purposes, e.g., treating hyperphe- (Continued)

nylalaninemia, including phenylketonuria, and other disorders, including cancer.

18 Claims, 34 Drawing Sheets

Specification includes a Sequence Listing.

Related U.S. Application Data

(60) Provisional application No. 61/301,478, filed on Feb. 4, 2010.

(51) Int. Cl.
    *C07K 1/14* (2006.01)
    *A61K 38/51* (2006.01)
    *A61K 9/00* (2006.01)
    *A61K 47/60* (2017.01)

(52) U.S. Cl.
    CPC ........ *C07K 1/14* (2013.01); *C12Y 403/01024* (2013.01)

(56) References Cited

U.S. PATENT DOCUMENTS

| | | | |
|---|---|---|---|
| 5,166,322 | A | 11/1992 | Shaw et al. |
| 5,206,344 | A | 4/1993 | Katre et al. |
| 5,466,781 | A | 11/1995 | Dorin et al. |
| 5,690,929 | A | 11/1997 | Lishko et al. |
| 5,753,487 | A | 5/1998 | Eigtved et al. |
| 5,766,897 | A | 6/1998 | Braxton |
| 5,981,239 | A | 11/1999 | Liu |
| 6,057,292 | A | 5/2000 | Cunningham et al. |
| 6,312,939 | B1 | 11/2001 | Roberts et al. |
| 6,433,148 | B1 | 8/2002 | Macias et al. |
| 6,451,986 | B1 | 9/2002 | Pettit |
| 6,461,849 | B1 | 10/2002 | Olsen et al. |
| 6,548,644 | B1 | 4/2003 | Pettit |
| 6,586,398 | B1 | 7/2003 | Kinstler et al. |
| 6,596,849 | B1 | 7/2003 | Roffler et al. |
| 6,617,118 | B2 | 9/2003 | Roffler et al. |
| 6,686,164 | B1 | 2/2004 | Olsen et al. |
| 6,737,259 | B1 | 5/2004 | Clark |
| 6,939,541 | B2 | 9/2005 | Roberts et al. |
| 6,939,941 | B2 | 9/2005 | Gilmore et al. |
| 6,967,097 | B2 | 11/2005 | Yoshida et al. |
| 7,141,544 | B2 | 11/2006 | Somers et al. |
| 7,531,341 | B1 | 5/2009 | Vellard et al. |
| 7,534,595 | B2 | 5/2009 | Vellard et al. |
| 7,537,923 | B2 | 5/2009 | Kakkis et al. |
| 7,553,653 | B2 | 6/2009 | Gamez et al. |
| 7,560,263 | B2 | 7/2009 | Kakkis et al. |
| 7,790,433 | B2 | 9/2010 | Kakkis et al. |
| 8,114,958 | B2 | 2/2012 | Soares et al. |
| 2003/0082238 | A1 | 5/2003 | Babich et al. |
| 2004/0126358 | A1 | 7/2004 | Warne et al. |
| 2005/0163708 | A1 | 7/2005 | Robinson et al. |
| 2008/0008695 | A1* | 1/2008 | Vellard .................... C12N 9/88 424/94.3 |
| 2008/0064856 | A1 | 3/2008 | Warne et al. |
| 2008/0274952 | A1 | 11/2008 | Soares et al. |
| 2009/0038023 | A1 | 2/2009 | Weiner et al. |
| 2009/0047265 | A1* | 2/2009 | Kakkis .................... A61K 38/51 424/94.1 |
| 2011/0201022 | A1 | 8/2011 | Foehr et al. |

FOREIGN PATENT DOCUMENTS

| | | |
|---|---|---|
| WO | WO 2002/094853 | 11/2002 |
| WO | WO 2003/018759 | 3/2003 |
| WO | WO 2003/072743 | 9/2003 |
| WO | WO 2004/044169 | 5/2004 |
| WO | WO 2006-034373 | 3/2006 |
| WO | WO 2006/099207 | 9/2006 |
| WO | WO 2008/069958 | 6/2008 |
| WO | WO 2008/153776 | 12/2008 |
| WO | WO 2009/025760 | 2/2009 |
| WO | WO 2010/014225 | 2/2010 |
| WO | WO 2011/097335 | 8/2011 |

OTHER PUBLICATIONS

TOSOH. Toyopearl Giga Cap Q 650M. 2007.*
TOSOH. Toyopearl Butyl 650M. 2007.*
Abell et al., "The Effects of Phenylalanine Ammonia-Lyase on Leukemic Lymphocytes in Vitro," *Cancer Research*, 32:285-290 (1972).
Abell et al., "An In Vivo Evaluation of the Chemotherapeutic Potency of Phenylalanine Ammonia-Lyase," *Cancer Research*, 33:2529-2532 (1973).
Abell et al., "Phenylalanine Ammonia-Lyase from the Yeast *Rhodotorula glutinis*," *Methods in Enzymology*, 142:242-253 (1987).
Abrams et al., "Rational Antigen Modification as a Strategy to Upregulate or Downregulate Antigen Recognition," *Current Opinion Immunology*, 12:85-91 (2000).
Alunni et al., "Mechanisms of Inhibition of Phenylalanine Ammonia-Lyase by Phenol Inhibitors and Phenol/Glycine Synergistic Inhibitors," *Archives of Biochemistry and Biophysics*, 412:170-175 (2003).
Ambrus et al., "Phenylalanine Reactors with Immobilized Depletion for the Management of Phenylketonuria: Use of Enzyme Enzymes," *Science*, 201:837-839 (1978).
Ambrus et al., "Depletion of Phenylalanine in the Blood of Phenylketonuric Patients Using a PAL-Enzyme Reactor, an In Vitro Study," *Research Communications in Chemical Pathology and Pharmacology*, 37(1):105-111 (1982).
Ambrus et al., "In Vivo Safety of Hollow Fiber Enzyme-Reactors with Immobilized Phenylalanine and Ammonia-Lyase in a Large Animal Model for Phenylketonuria," *The Journal of Pharmacology Experimental Therapeutics*, 224(3):598-602 (1983).
Ambrus et al., "Extracorporeal Enzyme Reactors for Depletion of Phenylalanine in Phenylketonuria," *Annals of Internal Medicine*, 106:531-537 (1987).
Anson J. G., "Complete Nucleotide Sequence of the Rhodosporidium Toroloides Gene Coding for Phenylalanine Ammonia-lyase," *Gene*, 58:189-199 (1987).
Ao et al., "Fluoroimmunoassay for Antigen Based on Fluorescence Quenching Signal of Gold Nanoparticles," *Anal. Chem.*, 78(4):1104-1106 (2006).
Baedeker et al., "Structures of two Histidine Ammonia-Lyase Modifications and Implications for the Catalytic Mechanism," *European Journal of Biochemistry*, 269:1790-1797 (2002).
Becker et al., "Cloning, Sequencing, and Biochemical Characterization of the Nostocyclopeptide Biosynthetic Gene Cluster: Molecular Basis for Imine Macrocyclization," *Gene*, 325:35-42 (2004).
Bezanson et al., "Biosynthesis of Cinnamamide and Detection of Phenylalanine Ammonia-Lyase in *Streptomyces verticillatus*," *Canadian Journal of Microbiology*, 16:147-151 (1970).
Billett et al., "A Specific and Reversible Macromolecular Inhibitor of Phenylalanine Ammonia-Lyase and Cinnamic Acid-4-Hydroxylase in Gherkins," *Biochim. Biophys. Acta.*, 524:219-230 (1978).
Bourget et al., "Artificial Cell-Microencapsulated Phenylalanine Ammonia-Lyase," *Applied Biochemistry and Biotechnology*, 10:57-59 (1984).
Bourget et al., "Phenylalanine Ammonia-Lyase Immobilized in Semipermeable Microcapsules for Enzyme Replacement in Phenylketonuria," *Federation of European Biochemical Societies Letters*, 180(1):5-8 (1985).
Bourget et al., "Phenylalanine Ammonica-Lyase Immobilized in Microcapsules for the Depletion of Phenylalanine in Plasma in Phenylketonuric Rat Model," *Biochimica et Biophysica Acta*, 883:432-438 (1986).
Brannigan et al., "Protein Engineering 20 Years on," *Nature Reviews, Molecular Cell Biology*, 3:964-970 (2002).

(56) References Cited

OTHER PUBLICATIONS

Calabrese et al., "Crystal Structure of Phenylalanine Ammonia-Lyase: Multiple Helix Dipoles Implicated in Catalysis," *Biochemistry*, 43(36):11403-11416 (2004).
Chang et al., "A New Theory of Enterorecirculation of Amino Acids and Its Use for Depleting Unwanted Amino Acids Using Oral Enzyme-Artificial Cells, as in Removing Phenylalanine in Phenylketonuria," *Art. Cells Blood Subs. and Immob. Biotech.*, 23(1):1-21 (1995).
Chang et al., "Procedures for Microencapsulation of Enzymes, Cells and Genetically Engineered Microorganisms," *Molecular Biotechnology*, 17:249-260 (2001).
Chen et al., "Tuning the Activity of an Enzyme for Unusual Environments: Sequential Random Mutagenesis of Subtilisin E for Catalysis in Dimethylformamide," *Proc. Natl. Acad. Sci. U.S.A.*, 90:5618-5622 (1993).
Cheng et al., "Accelerated Clearance of Polyethylene Glycol-Modified Proteins by Anti-Polyethylene Glycol IgM," *Bioconjugate Chemistry*, 10:520-528 (1999).
Cheng et al., "Efficient Clearance of Poly(ethylene glycol)-Modified Immunoenzyme with Anti-PEG Monoclonal Antibody for Prodrug Cancer Therapy," *Bioconjugate Chemistry*, 11:258-266 (2000).
Chi et al., "Physical Stability of Proteins in Aqueous Solution: Mechanism and Driving Forces in Nonnative Protein Aggregation," *Pharmaceutical Research*, 21(6):1325-1336 (2003).
Chirino et al.,"Minimizing the Immunogenicity of Protein Therapeutics," *Drug Discovery Today*, 9(2):82-90 (2004).
Christiansen et al., "The Role of the MoFe protein alpha-125-Phe and beta-125-Phe Residues in *Azotobacter vinelandii* MoFe—Fe Protein Interaction," *Journal of Inorganic Biochemistry*, 80:195-204 (2000).
Cui et al., "Synthesis of $Ag_{core}Au_{shell}$ Bimetallic Nanoparticles for Immunoassay Based on Surface-Enhanced Raman Spectroscopy," *J. Phys. Chem. B*, 110(9):4002-4006 (2006).
D' Agostino, "Tetrahydrobiopterin and Mild Phenylketonuria," *New England Journal of Medicine*, 348:1723-1724 (2003).
Da Cunha, "Purification, Characterization and Induction of L-Phenylalanine Ammonia-Lyase in *Phaseolus vulgaris*," *European Journal of Biochemistry*, 178:243-248 (1988).
Dai et al., "Electrochemical Sensor for Immunoassay of Carcinoembryonic Antigen Based on Thionine Monolayer Modified Gold Electrode," *Cancer Detection and Prevention*, 29:233-240 (2005).
Davis, "Mimicking Posttranslational Modifications of Proteins," *Science*, 303:480-482 (2004).
Delgado et al., "The Uses and Properties of PEG-Linked Proteins," *Critical Reviews in Therapeutic Drug Carrier Systems*, 9(3-4):249-304 (1992).
Dengler, et al., "Development of a Propidium Iodide Fluorescence Assay for Proliferation and Cytotoxicity Assays," *Anti-Cancer Drugs*, 6:522-532 (1995).
Dermer (1994) "Another anniversary for the war on cancer" *Bio/Technology* 12:320.
Egrie et al., "Development and Characterization of Novel Erythropoiesis Stimulating Protein (NESP)," *British Journal of Cancer*, 84(Suppl. 1):3-10 (2001).
Elstad et al., "Modulation of B16-B16 Murine Melanoma Metastatic Phenotype by Tyrosine and Phenylalanine Restriction in the Absence of Host Selection Pressures," *Anticancer Research*, 13:523-528 (1993).
Elstad et al., "Tyrosine and Phenylalanine Restriction Sensitizes Adriamycin-Resistant P388 Leukemia Cells to Adriamycin," *Nutrition and Cancer*, 25:47-60 (1996).
Evans et al., "Bioconversion of Trans-Cinnamic Acid to L-Phenylalanine in an Immobilized Whole Cell Reactor," *Biotech. Bioeng.*, 30:1067-1072 (1987).
Faulkner et al., "High-level Expression of the Phenylalanine Ammonialyase-encoding Gene from Rhodosporidium Toruloides in *Saccharomyces cerevisiae* and *Escherichia coli* using a Bifunctional Expression System," *Gene*, 143:13-20 (1994).
Filpula et al., "Nucleotide Sequence of Gene for Phenylalanine Ammonia-lyase from Rhodotorula Rubra," *Nucl. Acid. Res.*, 16:11381 (1988).
Foehr (2009) "Development and Validation of an Assay to Detect Activity Neutralizing Antibodies (Nab assay) to rAvPAL-PEG" *2009 AAPS National Biotechnology Conference*. Available at : http://abstracts.aapspharmaceutica.com/ExpoNBC09/CC/forms/attendee/index.aspx?content=sessionInfo&sessionId=272 (last visited Jun. 27, 2011).
Freshney Culture of Animal Cells: A Manual of Basic Technique (Alan R. Liss, Inc., New York, NY), pp. 3-4 (1983).
Fritz et al., "Phenylalanine Ammonia-Lyase," *The Journal of Biological Chemistry*, 251(15):4646-4650 (1976).
Fu et al., "Inflence of Tyrosine and Phenylalanine Limitation on Cytotoxicity of Chimeric TGF-α Toxins on B16BL6 Murine Melanoma in Vitro," *Nutrition and Cancer*, 31(1):1-7 (1998).
Fu et al., "Focal Adhesion Kinase-Dependent Apoptosis of Melanoma Induced Tyrosine and Phenylalanine Deficiency," *Cancer Research*, 59:758-765 (1999).
Fu et al., "Specific Amino Acid Dependency Regulates Invasiveness and Viability of Androgen-Independent Prostate Cancer Cells," *Nutrition and Cancer*, 45(1):60-73 (2003).
Fu et al., "Selective Amino Acid Restriction Targets Mitochondria to Induce Apoptosis of Androgen-Independent Prostate Cancer Cell," *Journal of Cellular Physiology*, 208:522-534 (2006).
Gamez et al., "Development of Pegylated Forms of Recombinant Rhodosporidium Toruloides Phenylalanine Ammonia-Lyase for the Treatment of Classical Phenylketonuria," *Molecular Theory*, 11(6):986-989 (2005).
Ghindilis, "Direct Electron Transfer Catalysed by Enzymes: Application for Biosensor Development," *Biochemical Society Transactions*, 28(2):84-89 (2000).
Gilbert et al., "The Effect of Proteinases on Phenylalanine Ammonia-Lyase from the Yeast *Rhodotorula glutinis*," *Biochem. J.*, 199:715-723 (1981).
Gilbert et al., "Protection of Phenylalanine Ammonia-Lyase from Proteolytic Attack," *Biochemical and Biophysical Research Communications*, 131(2)557-563 (1985).
Goodson et al., "Site-Directed Pegylation of Recombinant Interleukin-2 at Its Glycosylation Site," *Biotechnology*, 8:343-346 (1990)
Graham, "Pegaspargase: A Review of Clinical Studies," *Advanced Drug Delivery Reviews*, 55:1293-1302 (2003).
Greenwald et al., "Effective Drug Delivery by PEGylated Drug Conjugates," *Advanced Drug Delivery Reviews*, 55:217-250 (2003).
Gura "Systems for identifying new drugs are often faulty," *Science* 278:1041-1042 (1997).
Harris et al., "Effect of Pegylation on Pharmaceuticals," *Nature Reviews, Drug Discovery*, 2:214-221 (2003).
Hedstrom et al., "Converting Trypsin to Chymotrypsin: The Role of Surface Loops," *Science*, 255(5049):1249-1253 (1992).
Hermeling et al., "Structure-Immunogenicity Relationships of Therapeutic Proteins," *Pharmaceutical Research*, 21(6):897-903 (2004).
Hershfield et al., "Use of Site-Directed Mutagenesis to Enhance the Epitope-Shielding Effect of Covalent Modification of Proteins with Polyethylene Glycol," *Proc. Natl. Acad. Sci. USA*, 88:7185-7189 (1991).
Hershfield, Enzyme Replacement Therapy of Adenosine Deaminase Deficiency with Polyethylene Glycol-Modified Adenosine Deaminase (PEG-ADA), *Immunodeficiency*, 4:93-97 (1993).
Hill et al., "Investigation of the Early Steps in Soraphen A Biosynthesis," *Chemical Communications*, 12:1358-1359 (2003).
Hofmann et al., "Recent Advances in the Application of Expressed Protein Ligation to Protein Engineering," *Current Opinion in Biotechnology*, 13(4):297-303 (2002).
Hoffmann et al .,"Sequence Analysis and Biochemical Characterization of the Nostopeptolide A Biosynthetic Gene Cluster from *Nostoc* sp. GSV224," *Gene*, 311:171-180 (2003).
Holden et al., "Chorismate Lyase: Kinetics and Engineering for Stability," *Biochim. Biphys. Acta*, 1594:160-167 (2002).
Hopfner et al., "New Enzyme Lineages by Subdomain Shuffling," *Proc. Natl. Acad. Sci., USA*, 95:9813-9818 (1998).
Hoskins et al., "Enzymatic Control of Phenylalanine Intake in Phenylketonuria," *The Lancet*, 392-394 (Feb. 23, 1980).

(56) References Cited

OTHER PUBLICATIONS

Hoskins et al., "Phenylalanine Ammonia Lyase in the Management of Phenylketonuria: The Relationship Between Ingested Cinnamate and Urinary Hippurate in Humans," *Research Communications in Chemical Pathology and Pharmacology*, 35(5):275-282 (1982).

Hoskins et al., "The Metabolism of Cinnamic Acid by Healthy and Phenylketonuric Adults: a Kinetic Study," *Biomedical Mass Spectrometry*, 11(6):296-300 (1984).

Ikeda et al., "Phenylalanine Ammmonia-Lyase Modified with Polyethylene Glycol: Potential Therapeutic Agent for Phenylketonuria," *Amino Acids*, 29(3):283-287 (2005).

International Search Report and Written Opinion for PCT/US2005/033895 (WO2006/034373), dated Sep. 5, 2006.

International Search Report and Written Opinion for PCT/US2008/006661 (WO2008/153776) dated Nov. 12, 2008.

International Search Report and Written Opinion for PCT/US2009/004386 (WO2010/014225) dated May 3, 2010.

International Search Report and Written Opinion for PCT/US2011/023534 (WO2011/097335) dated Aug. 10, 2011.

Kalaitzis et al., "Mutasynthesis of Enterocin and Wailupemycin Analogues," *Journal of the American Chemical Society*, 125:9290-9291 (2003).

Kalghatgi et al., "Multitubular Reactors with Immobilized L-Phenylalanine Ammonia-Lyase for Use in Extracorporeal Shunts," *Research Communications in Chemical Pathology and Pharmacology*, 27(3):551-561 (1980).

Kaufman, "A Model of Human Phenylalanine Metabolism in Normal Subjects and in Phenylalanine Patients," *Proc. Natl. Acad. Sci. USA*, 96:3160-3164 (1999).

Kerbel, "Human Tumor Xenografts as Predictive Clinical Models of Anticancer Drug Activity in Humans," *Cancer Biology & Therapy*, 2:(4)S134-S139 (2003).

Kim et al., "Trends in Enzyme Therapy for Phenylketonuria," *Molecular Therapy*, 10(2):220-224 (2004).

Kinstler et al., "Characterization and Stability of N-Terminally PEGylated rhG-CSF," *Pharmaceutical Research*, 13(7):996-1002 (1996).

Koch et al., "Large Neutral Amino Acid Therapy and Phenylketonuria: a Promising Approach to Treatment," *Molecular Genetics and Metabolism*, 79:110-113 (2003).

Koukol et al., "The Metabolism of Aromatic Compounds in Higher Plants," *The Journal of Biological Chemistry*, 236(10):2692-2698 (1961).

Kreitman, "Immunotoxins for Targeted Cancer Therapy," *The AAPS Journal*, 8(3):E532-551 (2006).

Kriwacki et al., "Combined Use of Proteases and Mass Spectrometry in Structural Biology," *Journal of Biomolecular Techniques*, 9(3):5-15 (1998).

Kropf et al., "Immunological Measurements of Transforming Growth Factor-Beta I (TGF-βI) in Blood; Assay Development and Comparison," *Clinical Chemistry*, 43(10):1965-1974 (1997).

Kyndt et al., "Characterization of a Bacterial Tyrosine Ammonia Lyase, a Biosynthetic Enzyme for the Photoactive Yellow Protein," *Federation of European Biochemical Societies Letters*, 512:240-244 (2002).

Langer et al., "Identification of Essential Amino Acids in Phenylalanine Ammonia-Lyase by Site-Directed Mutageneisis," *Biochemistry*, 36:10867-10871 (1997).

Langer et al.,"Methylidene-Imidazole (MIO) from Histidine and Phenylalanine Ammonia-Lyase," *Advances in Protein Chemistry*, 58:175-188 (2001).

Larue et al., "An Extracorporeal Hollow-Fiber Reactor for Pheylketonuria Using Immobilized Phenylalanine Ammonia Lyase," *Dev. Pharmacol. Ther.*, pp. 9:73-81 (1986).

Lazar et al., "Designing Proteins for Therapeutic Applications," *Current Opinion in Structural Biology*, 13:513-518 (2003).

Lee et al., "N-Terminal Site-Specific Mono-PEGylation of Epidermal Growth Factor," *Pharmaceutical Research*, 20(5):818-825 (2003).

Leong et al., Adapting Pharmacokinetic Properties of a Humanized Anti-Interleukin-8 Antibody for Therapeutic Applications using Site-Directed Pegylation, *Cytokine*, 16:(3):106-119 (2001).

Levy, "Phenylketonuria: Old Disease, New Approach to Treatment," *Proc. Natl. Acad. Sci. USA*, 96:1811-1813 (1999).

Liu et al., "Study on a Novel Strategy to Treatment of Phenylketonuria," *Art. Cells Blood Subs. Immob. Biotech.*, 30(4):243-257 (2002).

Liu et al., "Solid-Substrate Room-Temperature Phosphorescence Immunoassay Based on an Antibody Labeled with Nanopartiles Containing Dibromofluorescein Luminescent Molecules and Analytical Application," *Journal of Immunological Methods*, 307:34-40 (2005).

Lu et al., "Pegylation: a Method for Assessing Topological Accessibilities in Kv1.3," *Biochemistry*, 40:13288-13301 (2001).

Lucke et al.,"BH4-Sensitive Hyperphenylalaninemia: New Case and Review of Literature," *Pediatric Neurology*, 28(3):228-230 (2003).

Marconi et al., "Phenylalanine Ammonia-Lyase Entrapped in Fibers," *Biochimie*, 62:575-580 (1980).

Marshall et al., "Rational Design and Engineering of Therapeutic Proteins," *Drug Discovery Today*, 8(5):212-221 (2003).

Matalon et al., "Biopterin Responsive Phenylalanine Hydroxylase Deficiency," *Genetics in Medicine*, 6(1):27-32 (2004).

Maverakis et al., Autoreactive T Cells can be Protected from Tolerance Induction Through Competition by Flanking Determinants for Access to Class II MHC, *Proceedings of the National Academy of Sciences USA*, 100(9):5342-5347 (2003).

Meadows et al., "Dietary Influence of Tyrosine and Phenylalanine on the Response of B16 Melanoma to Carbidopa-Levodopa Methyl Ester Chemotherapy," *Cancer Res.*, 42:3056-3063 (1982).

Mehvar, "Modulation of the Pharmacokinetics and Pharmacodynamics of Proteins by Polyethylene Glycol Conjugation," *J. Pharm. Pharmaceut. Sci.*, 3(1):125-136 (2000).

Meyer et al., "Reduced Antibody Response to Streptavidin Through Site-Directed Mutagenesis," *Protein Science*, 10:491-503 (2001).

Mire-Sluis et al., "Recommendations for the Design and Optimization of Immunoassays Used in the Detection of Host Antibodies Against Biotechnology Products," *Journal of Immunological Methods*, 289:1-6 (2004).

Moffitt et al., "Discovery of Two Cyanobacterial Phenylalanine Ammonia Lyases: Kinetic and Structural Characterization," *Biochemistry*, 46:1004-1012 (2007).

Molineux, "Pegylation: Engineering Improved Pharmaceuticals for Enhanced Therapy," *Cancer Treatment Reviews*, 28(Suppl. A):13-16 (2002).

Moola et al.,"*Erwinia chrysanthemi* L-Aspariginase: Epitope Mapping and Production of Antigenically Modified Enzymes," *Biochemical Journal*, 302:921-927 (1994).

Moore, "Biosynthesis of Marine Natural Products: Microorganisms (Part A)," *Natural Products Reports*, 22:580-593 (2005).

National Institutes of Health, "Phenylketonuria (PKU): Screening and Management," *NIH Consensus Statement*, 17(3):1-33 (2000).

Nunez et al., "PPAR-γ Ligands and Amino Acid Deprivation Promote Apoptosis of Melanoma, Prostate, and Breast Cancer Cells," *Cancer Letters*, 236:133-141 (2006).

Owens et al., "The Genetic Engineering of Monoclonal Antibodies," *Journal of Immunological Methods*, 168:149-165 (1994).

Parkinson et al., "Pegvisomant in the Treatment of Acromegaly," *Advanced Drug Delivery Reviews*, 55:1303-1314 (2003).

Pedersen et al., "Preparation of Immobilized L-Phenylalanine Ammonia-Lyase in Tubular Form in Chemical Pathology and for Depletion of L-Phenylalanine," *Research Communications Pharmacology*, 20(3):559-569 (1978).

Pettit et al., "Structure-Function Studies of Interleukin 15 Using Site-Specific Multigenesis, Polyethylene Glycol Conjugation, and Homology Modeling," *The Journal of Biological Chemistry*, 272(4):2312-2318 (1997).

Pilbak et al., "The Essential Tyrosine-Containing Loop Conformation and the Role of the C-Terminal Multi-Helix Region in Eukaryotic Phenylalanine Ammonia-Lyases," *FEBS Journal*, 273:1004-1019 (2006).

(56) References Cited

OTHER PUBLICATIONS

Poppe et al., "Methylidene-Imidazolone: a Novel Electrophile for Substrate Activation," *Current Opinion in Chemical Biology*, 5:512-524 (2001).
Poppe et al., "Properties and Synthetic Applications of Ammonia-Lyases," *Current Organic Chemistry*, 7:1297-1315 (2003).
Poppe et al., "Friedel-Crafts-Type Mechanism for the Enzymatic Elimination of Ammonia from Histidine and Phenylalanine," *Angewandte Chemie Int. Ed.*, 44:3668-3688 (2005).
Ranby et al., "Immunoreactivity of Tissue Plasminogen Activator and of Its Inhibitor Complexes," *Thrombosis and Haemostasis*, 61(3):409-414 (1989).
Rao et al.,"Degradation of Aromatic Amino Acids by Fungi," *Canadian Journal of Biochemistry*, 45:1863-1872 (1967).
Reddy et al.,"Use of Peginterferon alfa-2a (40 KD) (Pegasys®) for the Treatment of Hepatitis C," *Advanced Drug Delivery Reviews*, 54:571-586 (2002).
Roberts et al., "In Vivo Effects of Phenylalanine Ammonia-Lyase," *Cancer Treatment Reports*, 60(3):261-263 (1976).
Rother et al., "Characterization of the Active Site of Histidine Ammonia-Lyase from *Pseudomonas putida*," *European Journal of Biochemistry*, 268:6011-6019 (2001).
Rother et al., "An Active Site Homology Model of Phenylalanine Ammonia-Lyase from *Petroselinum crispum*," *European Journal of Biochemistry*, 269:3065-3075 (2002).
Russell et al., "Recombinant Proteins for Genetic Disease," *Clin. Genet.*, 55:389-394 (1999).
Sarkissian et al., "A Different Approach to Treatment of Phenylketonuria: Phenylalanine Degradation with Recombinant Phenylalanine Ammonia Lyase," *Proceedings of the National Academy of Sciences USA*, 96:2339-2344 (1999).
Sarkissian et al., "A Heteroallelic Mutant Mouse Model: A New Orthologue for Human Hyperphenylalaninemia," *Molecular Genetics and Metabolism*, 69:188-194 (2000).
Schellekens, "Tactors Influencing the Immunogenicity of Therapeutic Proteins," *Nephrology Dialysis Transplantation*, 20( Suppl. 6):vi3-vi9 (2005).
Schultz et al., "Single-Target Molecule Detection with Nonbleaching Multicolor Optical Immunolabels," *Proceedings of the National Academy of Sciences USA*, 97(3):996-1001 (2000).
Schüpbach et al., "Heat-Mediated Immune Complex Dissociation and Enzyme-Linked Immunosorbent Assay Signal Amplification Render P24 Antigen Detection in Plasma as Sensitive as HIV-1 RNA Detection by Polymerase Chain Reaction," *AIDS*, 10(10):1085-1090 (1996).
Schuster et al., "Serine-202 is the Putative Precursor of the Active Site Dehydroalanine of Phenylalanine Ammonia Lyase. Site-directed Mutagenesis Studies on the Enzyme from Parsley (*Pefroselinum crispum* L.)," *Federation of European Biochemical Societies Letters*, 349:252-254 (1994).
Schuster et al., "The Mechanism of Action of Phenylalanine Ammonia-Lyase: The Role of Prosthetic Dehydroalanine," *Proceedings of the National Academy of Sciences USA*, 92:8433-8437 (1995).
Schwede et al., "Crystal Structure of Histidine Ammonia-Lyase Revealing a Novel Polypeptide Modification as the Catalytic Electrophile," *Biochemistry*, 38:5355-5361 (1999).
Shen et al., "Clearance of Phenylalanine Ammonia-Lyase from Normal and Tumor-Bearing Mice," *Cancer Research*, 37:1051-1056 (1977).
Shen et al., "Total-Body Radiation Suppression of the Clearance of Phenylalanine Ammonia-Lyase from Mouse Plasma," *Journal of the Reticuloendothelial Society*, 23(3):167-175 (1978).
Shen et al., "Biochemical Properties and Immunogenicity of L-Phenylalanine Ammonia-Lyase: Effects on Tumor-Bearing Mice," *Cancer Treatment Reports*, 63(6):1063-1068 (1979).
Sorlie et al. "Mechanistic Features and Structure of the Nitrogenase alpha-Gin-195 MoFe Protein," *Biochemistry*, 40:1540-1549 (2001).
Spaapen et al., Tetrahydrobiopterin-Responsive Phenylalanine Hydroxylase Deficiency, State of the Art, *Molecular Genetics and Metabolism*, 78:93-99 (2003).
Spencer et al., "A Strategy for Mapping and Neutralizing Conformational Immunogenic Sites on Protein Therapeutics," *Proteomics*, 2(3):271-279 (2002).
Stith et al., "Effects of Phenylalanine Ammonia-Lyase and Phenylalanine Deprivation on Murine Leukemic Lymphoblasts in Vitro," *Cancer Research*, 33:966-971 (1973).
Suchi et al., "Molecular Cloning of a cDNA Encoding Human Histidase," *Biochimica et Biophysica Acta*, 1216:293-295 (1993).
Sun et al., "Solid Substrate Phosphorescent Immunoassay Based on Bioconjugated Nanoparticles," *Analytical Letters*, 34(10):1627-1637 (2001).
Tang et al., "New Amperometric and Potentiometric Immunosensors Based on Gold Nanoparticles/Tris (2,2'-Bipyridyl)Cobalt(III) Multilayer Films for Hepatitis B Surface Antigen Determinations," *Biosensors and Bioelectronics*, 21:539-548 (2005).
Tangri et al., "Rationally Engineered Proteins or Antibodies with Absent or Reduced Immunogenicity," *Current Medical Chemistry*, 9:2191-2199 (2002).
Taylor et al., "Cloning and Expression of Rat Histidase," *The Journal of Biological Chemistry*, 265(30):18192-18199 (1990).
Taylor et al., "Site-Directed Mutagenesis of Conserved Serines in Rat Histidase," *Journal of Biological Chemistry*, 269(44):27473-27477 (1994).
Vellard, "The Enzyme as Drug: Application of Enzymes as Pharmaceuticals," *Current Opinion in Biotechnology*, 14:1-7 (2003).
Veronese et al., "Branched and Linear Poly(Ethylene Glycol): Influence of the Polymer Structure on Enzymological, Pharmacokinetic, and Immunological Properties of Protein Conjugates," *Journal of Bioactive and Compatible Polymers*, 12:196-207 (1997).
Veronese et al., "Introduction and Overview of Peptide and Protein Pegylation," *Advanced Drug Delivery Reviews*, 54(4):453-456 (2002).
Wang et al., "New Carbohydrate-Based Materials for the Stabilization of Proteins," *Journal of the American Chemical Society*, 1992, 114:378-380 (1992).
Wang et al., "New Preparation for Oral Administration of Digestive Enzyme. Lactase Complex Microcapsules," *Biomat. Art. Cells Immob. Biotech.*, 21(5):637-646 (1993).
Wang et al., "Structural and Biological Characterization of Pegylated Recombinant Interferon alpha-2b and its Therapeutic Implications," *Advanced Drug Delivery Reviews*, 54:547-570 (2002).
Wang et al., "Structure-Based Chemical Modification Strategy for Enzyme Replacement Treatment of Phenylketonuria," *Molecular Genetics and Metabolism*, 86(1-2):134-140 (2005) Academic Press, San Diego, CA.
Wang et al. Structural and biochemical characterization of the therapeutic *Anabaena variabilis* phenylalanine ammonia lyase,: *J. Mol. Biol.* 380:623-635 (2008).
Watts et al. "Discovery of Substrate Selectivity Switch in Tyrosine Ammonia-Lyase, a Member of the Aromatic Amino Acid Lyase Family," *Chemistry and Biology, Current Biology* (London, GB) vol. 13, No. 12, pp. 1317-1326 (Dec. 26, 2006).
Whittle et al., "Protein Structure-Based Drug Design," *Annual review of Biophysics and Biomolecular Structure*, 23:349-375 (1994)
Wieder et al., "Some Properties of Polyethylene Glycol: Phenylalanine Ammonia-Lyase Adducts," The Journal of Biological Chemistry, 254(24):12579-12587 (1979).
Wilks et al., "Design of a Specific Phenyllactate Dehydrogenase by Peptide Loop Exchange on the Bacillus *Stearothermophilus* Lactate Dehydrogenase Framework," *Biochemistry*, 31:7802-7806 (1992).
Williams et al., "The Gene sltA Encodes a Phenylalanine Ammonia-Lyase that is Involved in the Production of a Stilbene Antibiotic in *Photorhabdus luminescens* TT01," *Microbiology*, 151:2543-2550 (2005).
Woolf et al., "The Dietary Treatment of Phenylketonuria," *Archives of Disease in Childhood*, 33:31-45, vol. 33 (1958).
Xiang et al., "Inactivation, Complementation, and Heterologous Expression of encP, a Novel Bacterial Phenylalanine Ammonia-Lyase Gene," *Journal of Biological Chemistry*, 277(36):32505-32509 (2002).
Xiang et al., "Biochemical Characterization of a Prokaryotic Phenylalanine Ammonia Lyase," *Journal of Bacteriology*, 187(12):4286-4289 (2005) [incl. Author's correction 188(14):5331 2006].

(56) References Cited

OTHER PUBLICATIONS

Yeung et al., "Elimination of an Immunodominant CD4+ T Cell Epitope in Human IFN-β Does Not Result in an In Vivo Response Directed at the Subdominant Epitope," *Journal of Immunology,* 172:6658-6665 (2004).

Yoshioka et al., "Optimal Site-Specific PEGylation of Mutant TNF-α Improves Its Antitumor Potency," *Biochemical and Biophysical Research Communications,* 315:808-814 (2004).

Zhao et al., "Development of an Assay to Determine the Plasma Concentration of a PEGylated Phenylalanine Ammonia Lyase (rAvPAL-PEG), an Enzyme Substitution Therapy for the Treatment of Phenylketonuria (PKU)," *2009 AAPS National Biotechnology Conference.* Available at http://abstracts.aapspharmaceutica.com/ExpoNBC09/CC/forms/attendee/index.aspx?content=sessionInfo&sessionId=289 (last visited Jun. 27, 2011).

Zon et al., "Inhibitors of Phenylalanine Ammonia-Lyase: 1-Aminobenzylphosphonic Acids Substituted in the Benzene Ring," *Phytochemistry,* 59:9-21 (2002).

Tosoh Bioscience LLC. Process Media Products Toyopearl GigaCap Q-650. Nov. 20, 2008 [Retrieved from the Internet on Aug. 2, 2011:<URL: http://web.archive.org/web/20081120025210/http://www.separations.us.tosohbioscience.com/Products/ProcessMedia/ByMode/IEC/ToyopearlGigaCapQ-650.htm>].

Database NCBI, Accession No. X51513, Nov. 28, 1996, the whole sequence.

Database NCBI, Accession No. CAA31209, Mar. 23, 1993.

\* cited by examiner

Gene Sequence of Nostoc punctiforme PAL

```
  1 atgaatataa catctctaca acagaacata acgcgttctt ggcaaatacc tttcactaat
 61 agttcagatt caatcgtaac tgtaggcgat caatcgacga caatcgacga ggttgtaaat
121 gttgtcgtc atggaacaca ggtgcgctta actgataatg cagatgtcat tcggggtgtt
181 caagcatctt gtgattacat taacaatgca gtcgaaacag cacagccaat ttacggggtg
241 acatctggct ttggcggtat ggcagtgtt gtcatctctc gcgaacaagc agcggaactt
301 cagactaatt taatttggtt tctgaaatcc ggcgcaggaa acaaattatc gttagcagac
361 gtgcgtgcag ctatgctctt acgtgcaaat tcacatttgt atggtgcgtc tggtatacga
421 ctcgaactta ttcagcggat tgaaacttc gcgtgacacc ccatgtctat
481 gagtttggct ctatcggtgc tagcggcgat ttggtgccat tatcctacat tactggggca
541 ctaatcggtc tagatcctag ctttacagtt gacttcgacg gtaaagaaat ggatgccgtt
601 acagccttgt ctcgtttggg tttgccaaag ttgcaattgc aaccgaaaga aggtttagca
661 atgatgaatg gcacctcagt catgacaggt attgcagcta actgtgtgta cgatgcgaaa
721 gttttgctcg ctctgacaat gggtacac gccttagcca tcccggtca atacggaacg
781 aatcaatctt tccaccgtt tattcatcag tgcaagccac actatctttag actatggaca
841 gcagatcaaa tgtttctct gctgaaagat tcatctttag ttcgtgaaga gttggatggt
901 aaacacgaat accgtggtaa agatctgata caggatcgtt attctctccg ctgtctggca
961 cagttcatag ggccaatcgt tgatgggta tcagagatta ccaagcaaat cgaggtagaa
```

FIG. 1A

Gene Sequence of Nostoc punctiforme PAL

```
1021 atgaactcag tcaccgataa cccattgatt gatgtcgaga accaagttag ttatcacggc
1081 ggcaattttc tcggacagta tgtgggtgtg acaatggatc gcctacgtta ttacataggg
1141 ctattggcca aacacatcga tgtgcagatt gcacttcttg tctcgccaga gtttagcaac
1201 ggcttaccac cctctttagt tggtaatagc gatcgcaaag ttaatatggg actcaaaggt
1261 ttgcaaatca gtggaaactc gattatgcca ctgttgagct tctatggaaa ttccctagcc
1321 gatcgctttc ctacccacgc cgagcaattt aatcaaaata ttaacagcca aggctatatt
1381 tccgcaaatt tgacacgtcg ttccgtagac atatttcaga attatatggc gatcgcgttg
1441 atgtttggag ttcaagctgt tgacctccgc acatataaga tgaaaggtca ttatgatgca
1501 cgtacatgcc tctcacccaa tactgtgcag ttatacacag cagtctgcga ggtagttgga
1561 aagccactaa cgtctgtgcg tccatacatt tggaacgaca acgagcaatg tttagatgag
1621 catattgccc ggatttcagc tgatatcgct gtggtggtt taattgtgca agcagttgag
1681 catatttttt cgagcttaaa gtcaacgtaa
```

FIG. 1A
(Continued)

Protein Sequence of Nostoc punctiforme PAL

MNITSLQQNITRSWQIPFTNSSDSIVTVGDRNLTIDEVVNVARH

GTQVRLTDNADVIRGVQASCDYINNAVETAQPIYGVTSGFGGMADVVISREQAAELQT

NLIWFLKSGAGNKLSLADVRAAMLLRANSHLYGASGIRLELIQRIETFLNAGVTPHVY

EFGSIGASGDLVPLSYITGALIGLDPSFTVDFDGKEMDAVTALSRLGLPKLQLQPKEG

LAMMNGTSVMTGIAANCVYDAKVLLALTMGVHALAIQGLYGTNQSFHPFIHQCKPHPG

QLWTADQMFSLLKDSSIVREELDGKHEYRGKDLIQDRYSLRCLAQFIGPTVDGVSEIT

KQIEVEMNSVTDNPLIDVENQVSYHGGNFLGQYVGVTMDRLRYYIGLLAKHIDVQIAL

LVSPEFSNGLPPSLVGNSDRKVNMGLKGLQISGNSIMPLLSFYGNSLADRFPTHAEQF

NQNINSQGYISANLTRRSVDIFQNYMAIALMFGVQAVDLRTYKMKGHYDARTCLSPNT

VQLYTAVCEVVGKPLTSVRPYIWNDNEQCLDEHIARISADIAGGGLIVQAVEHIFSSL

KST

FIG. 1B

Gene Sequence of Anabaena variabilis PAL

```
  1  atgagacac tatctcaagc acaaagcaaa acctcatctc aacaatttc ttttactgga
 61  aattcttctg ccaatgtaat tattggtaat cagaaactca caatcaatga tgttgcaagg
121  gtagcgcgta atggcacctt agtgtcttta accaataaca ctgatatttt gcagggtatt
181  caggcatctt gtgattacat taataatgct gttgaatctg gggaaccaat ttatggagtg
241  acatctggtt ttggcgtat ggccaatgtt gccatatccc gtgaacaagc atctgaactc
301  caaaccaact tagttggtt cctgaaaaca ggtgcaggga acaaattacc cttggcggat
361  gtgcgcgcag ctatgctctt gcgtgcaaac tctcatatgc gcggtgcatc tggcatcaga
421  ttagaactta tcaagcgtat ggagatttc cttaacgctg gtgtcacacc atatgtgtat
481  gagtttggtt caattggtgc aagtggtgat ttagtgccac tatcctacat tactggttca
541  ctgatagct tagatcccag tttaggtt gacttcaccg gtaaagaaat ggatgcgcca
601  acagctctac gtcaactgaa tttgtcaccc ttgacattgt tgccgaagga aggcttggcg
661  atgatgaacg gcacttcagt catgacaggt attgcagcaa actgcgtcta cgatactcaa
721  attttaactg cgatcgctat gggcgttcac tatccatata cccaagcttt aaacggaacc
781  aatcaatcat tccatccatt tattccatat gttagccaat cccaaccac atcctggtca attatggca
841  gcagatcaga tgattttt gttagccaat tcccagttag ttcgtgatga gttagatggt
901  aaacacgatt atcgtgatca cgagttgatt caagatcgtt actcactccg atgcctccc
961  cagtatttgg ggccaatcgt tgatggaatt tcccagattg ccaaacaaat tgaaatcgaa
```

FIG. 2A

Gene Sequence of Anabaena variabilis PAL

```
1021 atcaactcag tcaccgataa cccactaatt gatgttgata accaagctag ctatcatgga
1081 ggaaatttcc tcggacagta cgtgggtatg ggaatggatc acctgcgtta ctatattggg
1141 ttattggcta aacacctaga tgtgcagatt gccctcctcg cctcaccaga gtttagcaat
1201 ggactaccac catctttatt aggcaaccga gaacgtaaag tcaatatggg actcaaaggt
1261 ctgcaaatat gcggtaactc aattatgcca ctgttgacct tctatggaaa ttccatcgcc
1321 gatcgctttc ctaccatgc agaacaattt aatcagaaca tcaacagtca aggatacact
1381 tcagcgactc tagccgcg ttctgtggat atcttccaga attatgttggc gatcgctctg
1441 atgttttggag tccaagctgt tgacctccgc acatataaaa agactggtca ttacgatgca
1501 cgcgcctgtc tatcacctgc aactgagcgc ttatattcag cagtccgcca cgtagttgga
1561 caaaaaccaa cttcagatcg cccatatatt tggaatgata atgagcaagg actggatgag
1621 catattgccc ggatttctgc tgatatcgct gctggtggtg tgattgtgca agcagttcaa
1681 gatatcttac cctgcttgca ttaa
```

FIG. 2A
(Continued)

Protein Sequence of Anabaena variabilis PAL

```
  1  mktlsqagsk tssqqfsftg nssanviign qkltindvar varngtlvsl tnntdilqgi
 61  qascdyinna vesgepiygv tsgfggmanv aisreqasel qtnlvwfikt gagnklpiad
121  vraamliran shmrgasgir lelikrmeif inagvtpyvy efgsigasgd lvplsyitgs
181  ligldpsfkv dfngkendap talrqlnlsp ltlipkegla mmngtsvmtg iaancvydtq
241  iltaiamgvh aldigalngt nqsfhpfihn skphpgqlwa adqmisilan sqlvrdeidg
301  khdyrdheli qdryslrclp qylgpivdgi sqiakqieie insvtdnpli dvdnqasyhg
361  gnflgqyvgm gmdhlryyig llakhldvqi allaspefsn glppslignr erkvnmglkg
421  lqicgnsimp lltfygnsia drfpthaeqf nqninsqqgyt satlarrsvd ifqnyvaial
481  mfgvqavdlr tykktghyda racispater lysavrhvvg qkptsdrpyi wndneggide
541  hiarisadia aggvivqavg dilpclh
```

FIG. 2B

Alignment of cyanobacterial protein sequences of N. punctiforme PAL (SEQ ID NO:4) and A. variabilis (SEQ ID NO:2) with EncP PAL (SEQ ID NO:5) and P. putida HAL (SEQ ID NO:6). Active site residues which correspond to PAL or HAL activity are highlighted and underlined.

```
Avar03005300    MKTLSQAQSK TSSQQFSFTG NSSANVIIGN QKLTINDVAR VARNGTLVSL
Npun02008223    MNITSLQQNI TRSWQIPFTN SSDSIVTVGD RNLTIDEVVN VARHGTQVRL
EncP            .......... .......... ..MFEVIELD MNVTLDQLED AARQRTPVEL
PputidaHAL      .......... .......... ..MTELTIKP GTLTLAQLRA IHAAPVRLQL Avar03005300    TNNTDILQGI QASCDYINNA VESGEPIYGV TSGFGGMANV AISREQASEL
Npun02008223    TDNADVIRGV QASCDYINNA VETAQPIYGV TSGFGGMADV VISREQAAEL
EncP            S..APVRSRV RASRDVLVKF VQDERVIYGV NTSMGGFVDH LVPVSQARQL
PputidaHAL      D..ASAAPAI DASVACVEQI IAEDRTAYGI NTGFGLLAST RIASHDLENL Avar03005300    QTNLVWFLKT GAGNKLPLAD VRAAMLLRAN SHMRGASGIR LELIKRMEIF
Npun02008223    QTNLIWFLKS GAGNKLSLAD VRAAMLLRAN SHLYGASGIR LELIQRIETF
EncP            QENLINAVAT NVGAYLDDTT ARTIMLSRIV SLARGNSAIT PANLDKLVAV
PputidaHAL      QRSLVLSHAA GIGAPLDDDL VRLIMVLKIN SLSRGFSGIR RKVIDALIAL
```

FIG. 4

```
Avar03005300    LNAGVTPYVY  EFGSIGASGD  LVPLSYITGS  LIGLDPSFKV  DFNGKEMDAP
Npun02008223    LNAGVTPHVY  EFGSIGASGD  LVPLSYITGA  LIGLDPSFTV  DFDGKEMDAV
EncP            LNAGIVPCIP  EKGSLGTSGD  LGPLAAIALV  CAGQW...KA  RYNGQIMPGR
PputidaHAL      VNAEVYPHIP  LKGSVGASGD  LAPLATMSLV  LLGEG...KA  RYKGQWLSAT Avar03005300    TALRQLNLSP  LTLLPKEGLA  MMNGTSVMTG  IAANCVYDTQ  ILTAIAMGVH
Npun02008223    TALSRLGLPK  LQLQPKEGLA  MMNGTSVMTG  IAANCVYDAK  VLLALTMGVH
EncP            QALSEAGVEP  MELSYKDGLA  LINGTSGMVG  LGTMVLQAAR  RLVDRYLQVS
PputidaHAL      EALAVAGLEP  LTLAAKEGLA  LLNGTQASTA  YALRGLFYAE  DLYAAAIACG Avar03005300    ALDIQALNGT  NQSFHPFIHN  SKPHPGQLWA  ADQMISLLAN  SQLVRDELDG
Npun02008223    ALAIQGLYGT  NQSFHPFIHQ  CKPHPGQLWT  ADQMFSLLKD  SSLVREELDG
EncP            ALSVEGLAGM  TKPFDPRVHG  VKPHRGQRQV  ASRLWEGLAD  SHLAVNELDT
PputidaHAL      GLSVEAVLGS  RSPFDARIHE  ARGQRGQIDT  AACFRDLLGD  SSEVS.....
```

FIG. 4
(Continued)

```
Avar03005300    ..........K  HDYRDHELIQ  DRYSLRCLPQ  YLGPIVDGIS  QIAKQIEIEI
Npun02008223    ..........K  HEYRGKDLIQ  DRYSLRCLAQ  FIGPIVDGVS  EITKQIEVEM
EncP            EQTLAGEMGT   VAKAGSLAIE  DAYSIRCTPQ  ILGPVVDVLD  RIGATLQDEL
PputidaHAL      ...........  LSHKNCDKVQ  DPYSLRCQPQ  VMGACLTQLR  QAAEVLGIEA Avar03005300    NSVTDNPLID   VDNQASYHGG  NFLGQYVGMG  MDHLRYYIGL  LAKHLDVQIA
Npun02008223    NSVTDNPLID   VENQVSYHGG  NFLGQYVGVT  MDRLRYYIGL  LAKHIDVQIA
EncP            NSSNDNPIVL   PEEAEVFHNG  HFHGQYVAMA  MDHLNMALAT  VTNLANRRVD
PputidaHAL      NAVSDNPLVF   AAEGDVISGG  NFHAEPVAMA  ADNLALAIAE  IGSLSERRIS Avar03005300    LLASPEFSNG   LPPSLLGNRE  RKVNMGLKGL  QICGNSIMPL  LTFYGNSIAD
Npun02008223    LLVSPEFSNG   LPPSLVGNSD  RKVNMGLKGL  QISGNSIMPL  LSFYGNSLAD
EncP            RFLDKSNSNG   LPAFLCREDP  .GLRLGLMGG  QFMTASITAE  TRTLTIPMSV
PputidaHAL      LMMDKHMS.Q   LPPFLVENG.  .GVNSGFMIA  QVTAAALASE  NKALSHPHSV Avar03005300    REPTHAEQFN   QNINSQGYTS  ATLARRSVDI  FQNYVAIALM  FGVQAVDLRT
Npun02008223    REPTHAEQFN   QNINSQGYIS  ANLTRRSVDI  FQNYMAIALM  FGVQAVDLRT
EncP            QSLTSTADF.   QDIVSFGFVA  ARRAREVLTN  AAYVVAFELL  CACQAVDIRG
PputidaHAL      DSLPTSANQ.   EDHVSMAPAA  GKRLWEMAEN  TRGVPAIEWL  GACQGLDLRK
```

FIG. 4
(Continued)

```
Avar03005300    YKKTGHYDAR ACLSPATERL YSAVRHVVGQ KPTSDRPYIW NDNEQGLDEH
Npun02008223    YKMKGHYDAR TCLSPNTVQL YTAVCEVVGK PLTSVRPYIW NDNEQCLDEH
EncP            ADKL....... ...SSFTRPL YERTRKIVP. .........F FDRDETITDY
PputidaHAL      GLKT....... ...SAKLEKA RQALRSEVA. .........H YDRDRFFAPD Avar03005300    IARISADIAA GGVIVQAVQD ILPCLH....
Npun02008223    IARISADIAG GGLIVQAVEH IFSSLKST..
EncP            VEKLAADLIA GEPVDAAVAA H.........
PputidaHAL      IEKAVEILLAK GSLTGLLPAG VLPSL.....
```

FIG. 4
(Continued)

Protein Sequence of AvPAL Variants (Cysteine Mutants)

A. AvPAL_C64S (SEQ ID NO:7)

MKTLSQAQSKTSSQQFSFTGNSSANVIIGNQKLTINDVARVARNGTLVSLTNNTDILQGIQASSDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPCLH

FIG. 5A

Protein Sequence of AvPAL Variants (Cysteine Mutants)

B. AvPAL_C318S (SEQ ID NO:8)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRSLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPCLH

FIG. 5B

Protein Sequence of AvPAL Variants (Cysteine Mutants)

C. AvPAL_C503S (SEQ ID NO: 9)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPCLH

FIG. 5C

Protein Sequence of AvPAL Variants (Cysteine Mutants)

D. AvPAL_C565S (SEQ ID NO:10)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPSLH

FIG. 5D

Protein Sequence of AvPAL Variants (Cysteine Mutants)

E. AvPAL_C565SC503S (SEQ ID NO:11)

MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYIGLLAKHLDVQIALLASPEFSNGLPPSLLGNRERKVNMGLKG
LQICGNSIMPLLTFYGNSIADRFPTHAEQFNQNINSQYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPSLH

FIG. 5E

COMPOSITIONS OF PROKARYOTIC PHENYLALANINE AMMONIA-LYASE VARIANTS AND METHODS OF USING COMPOSITIONS THEREOF

CROSS-REFERENCE TO RELATED APPLICATIONS

This application is a continuation of U.S. application Ser. No. 13/576,625, filed Aug. 1, 2012, which is a United States national stage application and claims the benefit of international Application No. PCT/US2011/023534, filed Feb. 3, 2011, which claims the benefit of U.S. provisional Application No. 61/301,478, filed Feb. 4, 2010, each of which is herein incorporated by referenced in its entirety.

SEQUENCE LISTING

The content of the following submission on text file is incorporated herein by reference in its entirety: a computer readable form (CRF) of the Sequence Listing, entitled 11808-264-999_SEQLIST.txt, of size 54,090 bytes, and created on Apr. 15, 2016.

FIELD

Provided herein are compositions related to prokaryotic phenylalanine ammonia-lyase (PAL) variants, including optimization of such compositions to enhance prokaryotic PAL catalytic activity and/or stability, while reducing immunogenicity and/or proteolytic sensitivity of prokaryotic PAL. Also provided herein are uses of such optimal compositions of prokaryotic PAL variants for therapeutic purposes, e.g., treating hyperphenylalaninemia (HPA), including phenylketonuria (PKU), and other disorders, including cancer.

BACKGROUND

Phenylalanine ammonia-lyase (PAL) is a non-mammalian enzyme widely distributed in plants (Koukol, et al., J. Biol. Chem. 236:2692-2698 (1961); Hanson, et al., The Enzymes 7:75-166 (1972); Poppe, et al., Curr. Org. Chem. 7:1297-1315 (2003)), some fungi (Rao, et al., Can. J. Biochem. 4512:1863-1872 (1967); Abell, et al., Methods Enzymol. 142:242-253 (1987)) and bacteria (Bezanson, et al., Can. J. Microbiol. 16:147-151 (1970); Xiang, et al., J. Biol. Chem. 277:32505-32509 (2002); Hill, et al., Chem. Commun. 1358-1359 (2003)) and can be recombinantly produced in *Escherichia coli*.

PAL from two cyanobacteria strains, *Anabaena variabilis* (Av) and *Nostoc punctiforme* (Np), has been cloned and expressed in bacteria (e.g., *Escherichia coli* (*E. coli*), and was shown to display PAL enzyme activity in vitro and in vivo (see, e.g., U.S. Pat. Nos. 7,531,341; 7,534,595; 7,537,923; and 7,560,263). A pegylated recombinant *Anabaena variabilis* PAL (rAvPAL-PEG) has also been produced, wherein the rAvPAL protein was derivatized by covalent attachment of polyethylene glycol (PEG) to increase its half-life and optimize its pharmacokinetic profile and/or reduce its immunogenicity (Id.). rAvPAL-PEG has been shown to metabolize phenylalanine and is being developed as an enzyme substitution therapy (EST) for patients disorders or diseases associated with elevated levels of phenylalanine, such as HPA, including PKU, as well as in cancer therapy (Id.).

Although PAL potentially has various therapeutic applications, the use of PAL can be limited by reduced specific activity and proteolytic instability. Similar to other therapeutic proteins, use of PAL as an enzyme therapy is accompanied by several disadvantages such as immunogenicity and proteolytic sensitivity (see Vellard, Curr. Opin. Biotechnol. 14:1-7 (2003)). Further, a delicate balance is required between substrate affinity and enzyme activity to achieve and maintain control of plasma phenylalanine levels within a normal somewhat narrow range in disorders characterized by hyperphenylalaninemia. As yet, a concerted effort toward improving these parameters has not been made due to a paucity of structural and biochemical knowledge regarding this protein.

Thus, there remains a need for PAL molecules with optimal kinetic characteristics, including potent catalytic activity, greater biological half-life, greater biochemical stability, and/or attenuated immunogenicity, for therapeutic use, including the treatment of HPA, including PKU, and other disorders, including cancer.

SUMMARY

Prokaryotic or bacterial PAL can serve as an effective treatment for HPA, including PKU, and other disorders, including cancer. Provided herein are compositions of prokaryotic PAL and biologically active fragments, mutants, variants or analogs thereof, with enhanced properties, such as more potent catalytic activity, greater biochemical stability and, for therapeutic applications, attenuated immunogenicity and/or greater biological half-life. Also provided herein are pharmaceutical compositions and formulations comprising prokaryotic PAL and biologically active fragments, mutants, variants or analogs thereof and a pharmaceutically acceptable carrier, that can include preservatives and/or stabilizers. Also provided herein are methods of production and purification of prokaryotic PAL and biologically active fragments, mutants, variants or analogs thereof, and methods of using such compositions for therapeutic purposes, including the treatment of HPA, including PKU, and other disorders, including cancer.

As used herein, "bacterial PAL" and "prokaryotic PAL" are used interchangeably to mean (1) wild-type PAL from a prokaryotic organism, including but not limited to PAL from *Streptomyces maritimus* (also known as EncP, SEQ ID NO:5, FIG. 4), *Nostoc punctiforme* (SEQ ID NO:2, FIG. 4), *Anabaena variabilis* (SEQ ID NO:4, FIG. 4), *Anacystis nidulans* (Lofflehardt, Z. Naturforsch. 31(11-12):693-9 (1976), *Photorabdus luminescens* TT01 (Williams, et al., Microbiology 151:2543-2550 (2005), and *Streptomyces verticillatus* (Bezanson, et al., Can. J. Microbiol. 16(3):147-51 (1970); (2) fragments, mutants, variants or analogs of such wild-type PAL enzymes that retain similar (i.e., at least 50%) catalytic activity for phenylalanine, and that can, for example, exhibit increased catalytic activity, greater biochemical stability, increased half-life, and/or decreased immunogenicity, and (3) chemically modified versions of such wild-type PAL enzymes or fragments, mutants, variants or analogs thereof that are linked to other chemical moieties that provide other advantageous effects, such as, for example and not for limitation, enhanced half-life and/or decreased immunogenicity. For example, any references to methods of making or using prokaryotic PAL, and fragments, mutants, variants, analogs or chemically modified versions thereof, and compositions of such enzyme(s), for therapeutic purposes, are meant to refer to methods of making, using or formulating all such wild-type prokaryotic PAL or fragments, mutants, variants, analogs or chemical modifications thereof.

In a first aspect, provided herein are pharmaceutical compositions comprising prokaryotic PAL and biologically active fragments, mutants, variants or analogs thereof, and a pharmaceutically acceptable carrier. One embodiment is a prokaryotic PAL from *Nostoc punctiforme* (SEQ ID NO:2) or biologically active fragment, mutant, variant or analog thereof. Another embodiment is a prokaryotic PAL from *Anabaena variabilis* (SEQ ID NO:4) or biologically active fragment, mutant, variant or analog thereof. Also provided herein are prokaryotic PAL variants that have greater phenylalanine-converting activity and/or reduced immunogenicity as compared to a wild-type PAL.

In specific embodiments, the prokaryotic PAL variants retain the wild-type active site residues at positions corresponding to Ser210, Ala-Ser-Gly triad (211-213), Asp214, Leu215, Asn270, Val269, Leu266, Leu134, His137, Lys468, Glu496, Gln500 in PAL from *Rhodosporidium toruloides* PAL (RtPAL) or conservative substitution(s) of these active site residue(s), of which the Ala-Ser-Gly triad at 211-213 is believed to be the binding site for phenylalanine.

Prokaryotic PAL variants include proteins in which one or more amino acid (e.g., cysteine) residues have been substituted by another amino acid (e.g., serine) residue to reduce protein aggregation that can be associated with decreased enzyme activity, increased immunogenicity, and/or other disadvantageous effects, such as reduced bioavailability, in vivo. Provided herein is a pharmaceutical composition, wherein one or more amino acid residues of the prokaryotic PAL variant have been substituted by another amino acid wherein the substitution increases phenylalanine-converting activity and/or reduces immunogenicity as compared to the wild-type PAL.

In some embodiments, one or more amino acid residues of the prokaryotic PAL variant have been substituted by another amino acid residue. In some embodiments, one or more cysteine residues of the prokaryotic PAL variant have been substituted by a serine residue. In certain embodiments, the prokaryotic PAL variant is an *Anabaena variabilis* PAL (AvPAL). In other embodiments, one or more cysteine residues of the AvPAL variant have been substituted by a serine residue selected from the group consisting of cysteine residues at positions 64, 318, 503 and 565. In specific embodiments, the cysteine residue at position 565 of the AvPAL variant has been substituted by a serine residue. In a certain embodiment, the cysteine residues at positions 503 and 565 of the AvPAL variant have been substituted by serine residues.

Prokaryotic PAL variants can also include fusion proteins in which the PAL enzyme has been fused to another heterologous polypeptide, such as a native or modified constant region of an immunoglobulin or a fragment thereof that retains the salvage epitope, known in the art to increase half-life.

Also provided herein are chemically modified versions of such prokaryotic PAL polypeptides, which have been linked to a chemical moiety that provides other advantageous effects. For example, nonspecific or site-specific (e.g., N-terminal) linkage of water-soluble polymers, e.g., polyethylene glycol, to polypeptides is known in the art to improve half-life, and linkage of chemical moieties can also reduce immunogenicity and/or improve protease resistance.

In some embodiments, the prokaryotic PAL variant comprises a water-soluble polymer. In certain embodiments, the prokaryotic PAL variant comprises polyethylene glycol. In other embodiments, the prokaryotic PAL variant is an AvPAL and the ratio of AvPAL and polyethylene glycol is about 1:3 (1:3 AvPAL:PEG). In a specific embodiment, the prokaryotic PAL variant is an AvPAL variant, the ratio of the AvPAL variant and polyethylene glycol is about 1:3 (1:3 AvPAL:PEG), and the cysteine residues at positions 503 and 565 of the AvPAL variant have been substituted by serine residues.

In some embodiments, one or more amino acid residues of the prokaryotic PAL variant have been substituted by a lysine residue. The pegylation of an additional lysine residue(s) in a prokaryotic PAL variant can result in an enzyme that has reduced immunogenicity, increased catalytic activity, and/or improved biochemical stability. Without being bound to a particular theory, it is hypothesized that a tyrosine residue at/near the active site of prokaryotic PAL (e.g., position 78 in AvPAL) can be a site for pegylation, which reduces enzyme activity. In one embodiment, one or more amino acids at/near the active site of the prokaryotic PAL variant that is not required for enzyme activity is substituted by a lysine residue. Without being bound to a particular theory, it is hypothesized that pegylation of the substituted lysine residue at/near the active site sterically hinders a tyrosine residue (e.g., position 78 in AvPAL) from being pegylated.

Such prokaryotic PAL variants are isolated and purified in accordance with the methods provided herein and is thereby present in amounts which enable using the prokaryotic PAL enzyme therapeutically. In some embodiments, a cDNA encoding for a complete or wild-type prokaryotic PAL is used. However, in other embodiments, a cDNA encoding for a biologically active fragment, mutant, variant or analog thereof can be used. Further, provided herein are compositions of optimized prokaryotic PAL obtained by structure-based molecular engineering approaches and/or chemically-modified (e.g., pegylated) forms of PAL. Specific embodiments contemplate optimal compositions of prokaryotic PAL with improved specific activity, enhanced stability, reduced immunogenicity and/or proteolytic sensitivity appropriate for therapeutic use. In one embodiment, the PAL is a pegylated form of *Nostoc punctiforme* PAL with improved specific activity, enhanced stability, reduced immunogenicity and/or proteolytic sensitivity. In another embodiment, the PAL is a pegylated form of *Anabaena variabilis* PAL with improved specific activity, enhanced stability, reduced immunogenicity and/or proteolytic sensitivity.

In various embodiments, the pegylation of a PAL variant is described in reference to the ratio of PAL:PEG or PEG:PAL. As used herein, and unless otherwise indicated, the ratio of "PAL:PEG" refers to the ratio of lysine residues on the PAL variant to PEG molecules in the pegylation reaction. Similarly, as used herein, and unless otherwise indicated, the ratio of "PEG:PAL" refers to the ratio of PEG molecules to lysine residues on the PAL variant in the pegylation reaction.

In one embodiment, pegylated prokaryotic PAL variants with reduced immunogenicity are provided. Another embodiment is a pegylated form of *Nostoc punctiforme* PAL (NpPAL) variant with reduced immunogenicity. Yet another embodiment is a pegylated form of AvPAL variant with reduced immunogenicity. Specific embodiments contemplate NpPAL or AvPAL variants in which pegylation is achieved by reacting the NpPAL or AvPAL variant with a water-soluble polymer, e.g., PEG. In some embodiments, pegylation is achieved by reacting the NpPAL or AvPAL variant once with PEG at a ratio of at least 1:1, at least 1:1.5, at least 1:2, at least 1:3, or at least 1:4 PAL:PEG. In one embodiment, the prokaryotic PAL variant is an AvPAL variant, and the pegylation is achieved using a PAL:PEG ratio of 1:3.

In some embodiments, the pegylated prokaryotic PAL variant is an AvPAL variant and the cysteine residues at positions 503 and 565 of AvPAL have been substituted with serine residues (SEQ ID NO:11).

In some embodiments, the biologically active sites of wild-type prokaryotic PAL are modified to optimize PAL kinetic characteristics. In one embodiment, a prokaryotic PAL variant has sufficient activity to reduce but also maintain plasma phenylalanine levels within the optimal range of about 120 µM to about 240 µM. In other embodiments, the biologically active prokaryotic PAL variant has a kcat of at least about 0.1 s-1 or greater than about 0.5 s-1. In some embodiments, the biologically active prokaryotic PAL variant has a kcat of at least about 0.2 s-1 or greater than about 1.0 s-1. In other embodiments, the biologically active prokaryotic PAL variant has a Km of between about 10 µM to about 1000 µM. In other embodiments, the biologically active prokaryotic PAL variant has a Km of between about 100 µM to about 1000 µM. In one embodiment, the biologically active prokaryotic PAL variant exhibits enzymatic activity that is from about two-fold to about 1000-fold times greater than that of the wild-type PAL. In other embodiments, the biologically active prokaryotic PAL variant exhibits enzymatic activity that is from about 10% to 100% higher than that of the wild-type PAL. Such biological active prokaryotic PAL variants can be formed using methods well known in the art, such as by site-directed mutagenesis. Also provided herein are uses of a prokaryotic PAL variant or a biologically active fragment, mutant, variant or analog thereof that metabolizes phenylalanine (i.e., converts phenylalanine to another substance) in the preparation of a medicament for the treatment of a deficiency in PAH activity, in mammals, such as humans, as well as a pharmaceutical composition containing a prokaryotic PAL variant for use in treating a deficiency in PAH activity.

In some embodiments, the biologically active sites of wild-type prokaryotic PAL can be modified to optimize PAL kinetic characteristics. In one embodiment, a prokaryotic PAL variant has sufficient activity to reduce plasma phenylalanine levels in a subject to a range from below the level of detection to between about 20 µM to 60 µM, such as less than about 20 µM, or less than about 10 µM, using standard detection methods well known in the art. In other embodiments, the biologically active prokaryotic PAL variant has a kcat of at least about 0.1 s-1, such as greater than about 0.5 s-1, and greater than about 1.0 s-1. In certain embodiments, the biologically active prokaryotic PAL variant has a kcat of at least about 0.4 s-1, such as greater than about 2.0 s-1, or greater than about 4.0 s-1. In other embodiments, the biologically active prokaryotic PAL variant has a Km of between about 10 µM to about 2000 µM. In certain embodiments, the biologically active prokaryotic PAL variant has a Km of between about 10 µM to about 1000 µM. In other embodiments, the biologically active prokaryotic PAL variant has a Km of between about 10 µM to about 500 µM. In yet other embodiments, the biologically active prokaryotic PAL variant exhibits enzymatic activity from about at least 50% of to about 10-fold greater than the wild-type PAL. Such biological active prokaryotic PAL variants can be formed using methods well known in the art, such as by site-directed mutagenesis. Also provided herein are uses of a prokaryotic PAL variant or a biologically active fragment, mutant, variant or analog thereof that metabolizes phenylalanine (i.e., converts phenylalanine to another substance) in preparation of a medicament for preventing or treating cancer in a subject, such as a human subject, as well as a pharmaceutical composition containing a prokaryotic PAL variant or a biologically active fragment, mutant, variant or analog thereof for use in preventing or treating cancer in a subject, such as a human subject. In some embodiments, the medicament is for preventing cancer in a human subject.

In some embodiments, the pharmaceutical composition comprises highly purified prokaryotic PAL variant derived from bacteria, or a biologically active fragment, mutant or analog thereof alone or in combination with a pharmaceutically suitable carrier. In some embodiments, preparations contain prokaryotic PAL variant with a purity greater than 90%, 95%, 96%, 97%, 98%, 99%, 99.2%, 99.5%, 99.6%, 99.7%, 99.8%, or 99.9%. In other embodiments, the relative specific activity of the prokaryotic PAL variant is at least about 50%, or greater than about 110%, of the specific activity of wild-type prokaryotic PAL.

In a second aspect, provided herein are methods of using prokaryotic PAL compositions for therapeutic purposes. In one embodiment, provided herein are methods of treating disorders caused all or in part by a deficiency in PAH activity by administering a therapeutically effective amount of a pharmaceutical composition comprising prokaryotic PAL variant to a subject in need of such treatment. The deficiency in PAH activity can be observed, e.g., as activity levels of 50% or less, 25% or less, or 10% or less or 1% or less, compared to normal levels of PAH activity and can manifest as elevated phenylalanine levels, for example, as in hyperphenylalaninemia, mild phenylketonuria or classic severe phenylketonuria. In some embodiments, the disease is PKU.

In specific embodiments, the subject is one who has been diagnosed as having a mutant phenylalanine hydroxylase (PAH). The mutant PAH may comprise a mutation in the catalytic domain of PAH. Exemplary such mutations include but are not limited to mutations F39L, L48S, I65T, R68S, A104D, S110C, D129G, E178G, V190A, P211T, R241C, R261Q, A300S, L308F, A313T, K320N, A373T, V388M E390G, A395P, P407S, and Y414C.

Also contemplated is a method of treating a subject having above normal concentration of plasma phenylalanine (e.g., greater than 180 µM or 360 µM) comprising administering to the subject a prokaryotic PAL variant composition in an amount effective to produce a decrease in the plasma phenylalanine concentration of the subject. In certain embodiments, the subject has a plasma phenylalanine concentration greater than 180 µM prior to administration of the prokaryotic PAL variant. In some embodiments, the subject has a plasma phenylalanine concentration of between 120 µM and 200 µM. In other embodiments, the subject has a plasma phenylalanine concentration of between 200 µM and 600 µM. In still other embodiments, the subject has a plasma phenylalanine concentration of between 600 µM and 1200 µM. Yet another class of subjects to be treated is those that have an unrestricted plasma phenylalanine concentration greater than 1200 µM.

In specific embodiments, the subject is an infant, such as an infant having a plasma phenylalanine concentration greater than 1200 µM. Provided herein are methods of treating an infant having phenylketonuria, comprising administering a prokaryotic PAL variant composition to the subject in an amount effective to produce a decrease in the plasma phenylalanine concentration of the infant. In certain embodiments, the infant is between 0 and 3 years of age. In one embodiment, the infant has a plasma phenylalanine concentration of between about 360 µM to about 4800 µM. In certain embodiments, prior to the administering of prokaryotic PAL variant, the infant has a phenylalanine concentration of about 1200 and the administering of prokaryotic PAL variant decreases the plasma phenylalanine concentration, for example, to about 1000 µM. In other embodiments, prior to the administering of prokaryotic PAL variant the infant has a phenylalanine concentration of about 800 µM and the administering of PAL decreases the plasma phenylalanine concentration to, for example, about 600 µM. In still further embodiments, prior to the administering of PAL variant the infant has a phenylalanine concentration of about 400 µM and the administering of PAL variant decreases the plasma phenylalanine concentration, for example, to about 300 µM. In some embodiments, the therapeutic methods contemplated herein reduce the plasma phenylalanine concentration of the infant to a range of between about 120 µM to about 360 µM or a range of between about 120 µM to about 240 µM.

Also contemplated herein is a method for the treating a pregnant female having HPA comprising administering to the subject prokaryotic PAL variant alone or in combination with a protein-restricted diet, wherein administration of prokaryotic PAL variant alone or in combination with the protein-restricted diet is effective to lower the phenylalanine concentration in the plasma of the subject as compared to the concentration in the absence of the combined administration. In certain embodiments, the subject has an unrestricted plasma phenylalanine concentration of greater than 180 µM but less than 600 In other embodiments, the subject has an unrestricted plasma phenylalanine concentration of greater than 500 µM but less than 1200 In still other embodiments, the subject has an unrestricted plasma phenylalanine concentration of greater than 1200 Pregnant subjects with a plasma phenylalanine concentration greater than, for example, 1200 µM are particularly attractive candidates for this type of therapy, as are subjects who are females of child-bearing age that are contemplating pregnancy. In embodiments, wherein the subject has a plasma phenylalanine concentration greater than 1200 µM, the method can optionally further comprise administering a protein-restricted diet to the subject.

Also provided herein are methods of treating classic severe PKU in a subject comprising administering to the subject a prokaryotic PAL variant or a biologically active fragment, mutant, variant or analog thereof wherein the administration of prokaryotic PAL variant is effective to lower the phenylalanine concentration in the plasma of the subject as compared to the concentration in the absence of prokaryotic PAL administration. In some embodiments, a subject selected for treatment according to the methods provided herein will have an elevated plasma Phe concentration, such as greater than 1800 µM in the absence of the therapeutic. Other embodiments contemplate a subject that has a plasma phenylalanine concentration of greater than 1000 µM in the absence of a therapeutic regimen. In some embodiments, the combined administration methods provided herein decrease the plasma phenylalanine concentration of the subject to less than 600 µM. In one embodiment, it is decreased to less than 500 µM. In another embodiment, the combined administration decreases the plasma phenylalanine concentration of the subject in the range from about 120 µM to about 360 µM. In another embodiment, the plasma phenylalanine concentration of the subject is reduced in the range from about 120 µM to about 240 µM.

In one embodiment, methods are provided herein for treating a subject having a disorder characterized by a deficiency in PAH activity (e.g., hyperphenylalaninemia, mild phenylketonuria, or classic severe phenylketonuria, a subject having above normal concentration of phenylalanine, an infant having a plasma phenylalanine concentration greater than 1200 µM, or a pregnant female having phenylalaninemia), comprising administering to the subject a therapeutically effective amount of a pharmaceutical composition comprising a prokaryotic PAL variant and a pharmaceutically acceptable carrier, wherein the prokaryotic PAL variant has a greater phenylalanine-converting activity and/or a reduced immunogenicity as compared to a wild-type PAL and is effective in reducing the phenylalanine concentration in the blood, serum or plasma, of the subject to a range as described hereinabove. In some embodiments, one or more amino acid residues of the prokaryotic PAL variant have been substituted by another amino acid residue wherein the substitution increases phenylalanine-converting activity and/or reduces immunogenicity as compared to the wild-type PAL. In certain embodiments, one or more cysteine residues of the prokaryotic PAL variant have been substituted by another amino acid residue. In some embodiments, one or more cysteine residues of the prokaryotic PAL variant have been substituted by a serine residue. In one embodiment, the prokaryotic PAL variant is an AvPAL variant. In certain embodiments, one or more cysteine residues of the AvPAL variant have been substituted by a serine residue that is selected from the group consisting of cysteine residues at positions 64, 318, 503 and 565, by a serine residue at position 565, or by serine residues at positions 503 and 565. In some embodiments, the prokaryotic PAL variant comprises a water-soluble polymer. In some embodiments, the water-soluble polymer is polyethylene glycol. In a specific embodiment, the prokaryotic PAL variant is an AvPAL variant, and the ratio of the AvPAL variant and the polyethylene glycol is about 1:3 (1:3 AvPAL:PEG). In one embodiment, the prokaryotic PAL variant is an AvPAL variant, the ratio of the AvPAL variant and the polyethylene glycol is about 1:3 (1:3 AvPAL:PEG), and the cysteine residues at positions 503 and 565 of the AvPAL variant have been substituted by serine residues.

Certain embodiments include optimizing the dosage to the needs of the organism to be treated, for example, mammals or humans, to effectively ameliorate the disease symptoms. Prokaryotic PAL variant can be administered in a single daily dose, multiple doses on a daily basis, in a single weekly dose or multiple doses on a weekly basis. In some embodiments, the prokaryotic PAL variant therapy is not continuous, but rather prokaryotic PAL variant is administered on a daily basis until the plasma phenylalanine concentration of the subject is decreased, for example, to less than 360 In some embodiments, wherein the plasma phenylalanine concentration of the subject is monitored on a daily basis and the prokaryotic PAL variant is administered when a 10% increase in plasma phenylalanine concentration is observed. In other embodiments, doses are delivered once weekly. Doses of at least 0.001 mg/kg, 0.005 mg/kg, 0.01 mg/kg, or 0.05 mg/kg are contemplated, and can range up to 0.1 mg/kg, 0.5 mg/kg, 1.0 mg/kg, 2.0 mg/kg or higher per week. In some embodiments, the dose is 2 mg/kg/week, 1 mg/kg/week, 0.1 mg/kg/week, or 0.01 mg/kg/week.

A variety of parenteral or nonparenteral routes of administration, including oral, transdermal, transmucosal, intrapulmonary (including aerosolized), intramuscular, subcutaneous, or intravenous that deliver equivalent dosages are contemplated. Administration by bolus injection or infusion directly into the joints or CSF is also specifically contemplated, such as intrathecal, intracerebral, intraventricular, via lumbar puncture, or via the *cisterna magna*. In some embodiments, the doses are delivered subcutaneously or orally.

Other means of increasing prokaryotic PAL variant activity in the human subjects are also contemplated, including gene therapy. Transfer of a prokaryotic PAL variant gene is possible through a variety of means known in the art, including viral vectors, homologous recombination, or direct DNA injection. Within the scope of this aspect are embodiments featuring nucleic acid sequences encoding all or a part of prokaryotic PAL variant or a biologically active mutant or analogs thereof, which can be administered in vivo into cells that are affected with PAH deficiency.

In another embodiment, prokaryotic PAL variant or a biologically active fragment, mutant, variant or analog thereof can also be administered in combination with a protein-restricted diet. The protein-restricted diet administered in the methods herein is one that is a phenylalanine-restricted diet wherein the total phenylalanine (Phe) intake of the subject is restricted to less than 600 mg per day. In other embodiments, the protein-restricted diet is a phenylalanine-restricted diet wherein the total Phe is restricted to less than 300 mg per day. In still other embodiments, the protein-restricted diet is one supplemented with one or more amino acids, such as, for example and not for limitation, tyrosine, valine, isoleucine and/or leucine.

Also contemplated is a pharmaceutical composition comprising a prokaryotic PAL variant or a biologically active fragment, mutant, variant or analog thereof and a pharmaceutically acceptable carrier, diluent or excipient. The pharmaceutical composition can further comprise a medical protein supplement. In other embodiments, the prokaryotic PAL variant composition is part of an infant formula. In still other embodiments, the protein supplement is phenylalanine-free. The protein supplement can be fortified with L-tyrosine, L-glutamine, L-carnitine at a concentration of 20 mg/100 g supplement, L-taurine at a concentration of 40 mg/100 g supplement and selenium. It can further comprise the recommended daily doses of minerals, e.g., calcium, phosphorus and magnesium. The supplement further can comprise the recommended daily dose of one or more amino acids selected from the group consisting of L-leucine, L-proline, L-lysine acetate, L-valine, L-isoleucine, L-arginine, L-alanine, glycine, L-asparagine monohydrate, L-tryptophan, L-serine, L-threonine, L-histidine, L-methionine, L-glutamic acid, and L-aspartic acid. In addition, the supplement can be fortified with the recommended daily dosage of vitamins A, D and E. The supplement can comprise a fat content that provides at least 40% of the energy of the supplement. Such a supplement can be provided in the form of a powder supplement or in the form of a protein bar.

Also provided herein are methods of treating various forms of cancer by administering a therapeutically effective amount of a pharmaceutical composition comprising a prokaryotic PAL variant to a subject. In a broad embodiment, the cancer is a cancer wherein the proliferation and/or survival of cells derived from the cancer is sensitive to phenylalanine restriction or depletion. In some embodiments, the cancer is lung cancer, brain or central nervous system cancer, colon cancer, prostate cancer, renal cancer, liver cancer, or metastatic melanoma. In other embodiments, the cancer is head and neck cancer, ovarian cancer, uterine cancer, leukemia (e.g., acute myeloid leukemia or acute lymphoblastoid leukemia) or myeloma. In yet other embodiments, the cancer is pediatric cancer or a resistant cancer (i.e., a cancer that has been shown to be resistant to cancer therapeutic agents or targeted cancer therapeutic agents).

Also provided herein are methods of treating Parkinson's Disease (PD) by administering a therapeutically effective amount of a pharmaceutical composition comprising prokaryotic PAL variant to a subject.

In a third aspect, provided herein are pharmaceutical compositions or formulations of prokaryotic PAL variants, comprising prokaryotic PAL variant and biologically active fragments, mutants, variants or analogs thereof, and a pharmaceutically acceptable carrier, wherein the pharmaceutically acceptable carrier comprises a stabilizer. In some embodiments, the stabilizer is L-phenylalanine or structural analog thereof. In some embodiments, the stabilizer is selected from the group consisting of L-phenylalanine, trans-cinnamic acid and benzoic acid. In certain embodiments, the stabilizer is L-phenylalanine. In some embodiments the stabilizer is trans-cinnamic acid. In other embodiments, the stabilizer is benzoic acid. Also provided are methods of treating cancer using such pharmaceutical compositions or formulations.

In a specific embodiment, the pharmaceutical composition or formulation comprises a prokaryotic PAL variant and a pharmaceutically acceptable carrier, wherein the prokaryotic PAL variant is an AvPAL variant, the ratio of the AvPAL variant and polyethylene glycol is about 1:3 (1:3 AvPAL:PEG), the cysteine residues at positions 503 and 565 of the AvPAL variant have been substituted by serine residues, and the pharmaceutically acceptable carrier comprises a stabilizer. In some embodiments, the stabilizer is L-phenylalanine or structural analog thereof. In other embodiments, the stabilizer is selected from the group consisting of L-phenylalanine, trans-cinnamic acid and benzoic acid. In some embodiments, the stabilizer is L-phenylalanine. In one embodiment, the stabilizer is trans-cinnamic acid. Also provided are methods of treating hyperphenylalaninemia, including phenylketonuria, using such pharmaceutical compositions or formulations.

In a fourth aspect, provided herein are pharmaceutical compositions or formulations of pegylated AvPAL variants, wherein the ratio of the AvPAL variant and polyethylene glycol is about 1:3 (1:3 AvPAL:PEG), and one or more cysteine residues of the AvPAL variant have been substituted by serine residues, and a pharmaceutically acceptable carrier, wherein the pharmaceutically acceptable carrier comprises one or more (such as at least two) stabilizers and, optionally, a preservative (i.e., anti-microbial agent). The concentration of the pegylated AvPAL variant in the formulation can be from about 1 to 50 mg/mL (about 0.016 to 0.8 mM), such as from about 5 to 20 mg/mL (about 0.08 to 0.33 mM), or from about 5 to 15 mg/mL (about 0.08 to 0.25 mM). In some embodiments, the pharmaceutical composition or formulation comprises Tris-HCl or its equivalent as buffering agent, and/or NaCl or its equivalent as isotonicity-adjusting agent. The concentration of Tris-HCl or its equivalent in the formulation can be from about 5 to 50 mM, such as from about 5 to 20 mM, or from about 5 to 15 mM. The concentration of NaCl or its equivalent in the formulation can be from about 100 to 200 mM, such as from about 120 to 170 mM, or from about 120 to 150 mM. The pH of the formulation can be from about pH 6.0-8.0, such as about pH 6.5-7.5, or about pH 7.0-7.6. In some embodiments, the stabilizers are L-phenylalanine (Phe) or structural analog thereof and glycine (Gly) or structural analog thereof. The concentration of Phe or structural analog thereof in the formulation can be from about 0.1 to 10 mM, such as from about 0.5 to 5 mM, or from about 0.5 to 1.5 mM. The concentration of Gly or structural analog thereof in the formulation can be from about 0.1 to 100 mM, such as from about 1.0 to 100 mM, from about 1.0 to 20 mM, or from about 20 to 100 mM. For example, the concentration of Gly in the formulation can be about 0.1, 0.2, 0.3, 0.4, 0.5, 1.0, 2.0, 3.0, 4.0, 5.0, 10, 15, 20, 25, 30, 40, 50, 60, 70, 80, 90, or 100 mM. In some embodiments, the preservative is m-cresol or structural analog thereof. The concentration of m-cresol or structural analog in the formulation can be from about 0.1% to 1% (w/v), such as from about 0.1% to 0.5% (w/v), or from about 0.3% to 0.5% (w/v). In some embodiments, the stabilizers are Phe and Gly and the preservative is m-cresol. Any combination of AvPAL variants, stabilizers, buffering agents, isotonicity agents, preservatives, and/or other ingredients provided herein, as well as associated pH values and concentrations, are contemplated in the compositions or formulations provided herein. Also provided are methods of treating HPA, e.g., PKU, or cancer using such pharmaceutical compositions or formulations.

In a specific embodiment, the pharmaceutical composition or formulation comprises a pegylated AvPAL variant, wherein the ratio of the AvPAL variant and polyethylene glycol is about 1:3 (1:3 AvPAL:PEG), and the cysteine residues at positions 503 and 565 of the AvPAL variant have been substituted by serine residues, and a pharmaceutically acceptable carrier comprising Tris-HCl as buffering agent, NaCl as isotonicity agent, Phe and Gly as stabilizers and, optionally, m-cresol as preservative (i.e., anti-microbial agent). In one embodiment, the concentration of pegylated AvPAL variant in the formulation is about 10+/−5 mg/mL (about 0.16+/−0.08 mM). In some embodiments, the concentration of Tris-HCl in the formulation is about 10 mM+/−5 mM. In other embodiments, the pH of the formulation is about pH 7.3+−0.3. In another embodiment, the concentration of NaCl in the formulation is about 135 mM+/−15 mM. In some embodiments, the concentration of Phe in the formulation is about 1+/−0.5 mM. In some embodiments, the concentration of Gly in the formulation is about 10.5+/−9.5 mM. In other embodiments, the concentration of Gly in the formulation is about 60+/−40 mM. In other embodiments, the concentration of Gly in the formulation is about 50.5+/−49.5 mM. In some embodiments, the formulation comprises m-cresol as preservative. In another embodiment, the concentration of m-cresol in the formulation is about 0.4%+/−0.1% (w/v). Combinations of the above concentrations and pH values are also contemplated. Also provided are methods of treating HPA, e.g., PKU, or cancer using such pharmaceutical compositions or formulations.

In a fifth aspect, provided herein are methods to produce recombinant prokaryotic PAL or a biologically active fragment, mutant, variant or analog thereof in amounts which enable using the enzyme therapeutically. In certain embodiments, the PAL is derived from bacteria including, but not limited to, *Streptomyces, Sorangium, Pseudomonas*, and cyanobacteria such as *Nostoc* and *Anabaena*. In some embodiments, PAL is derived from the bacterial species *Streptomyces maritimus, S. verticillatus, Soragium cellulosum, Nostoc punctiforme, Nostoc tobacum, Anabaena variabilis*, or *Pseudomonas putida*. In certain embodiments, PAL is derived from cyanobacteria species *Nostoc punctiforme* or *Anabaena variabilis*. In a specific embodiment, PAL is derived from *Anabaena variabilis*. In another embodiment, prokaryotic PAL enzyme activity is generated using cDNA or DNA sequences that are derived from sequences sometimes described as coding for HAL activity or featuring a PAL-HAL motif, but possessing key PAL residues that differ from HAL.

In a broad embodiment, the method comprises the step of transforming a cDNA or DNA encoding for all or a part of a prokaryotic PAL or a biologically active fragment, mutant, variant or analog thereof into a cell suitable for the expression thereof. In one embodiment, an expression vector is used to transfer the DNA into a suitable cell or cell line for expression thereof. In a specific embodiment, the cDNA or DNA is transformed into *E. coli* and recombinant prokaryotic PAL is overexpressed, optionally as a fusion protein. In a further embodiment, the method of producing prokaryotic PAL comprises: (a) growing cells transformed with a cDNA or DNA encoding all or a biologically active fragment, mutant, variant or analog thereof of prokaryotic PAL in a suitable growth medium to an appropriate density to produce a seed culture, (b) introducing the transformed cells into a bioreactor, (c) supplying a suitable growth medium to the bioreactor, and (d) separating the transfected cells containing the enzyme from the media.

In one embodiment, recombinant prokaryotic PAL or a biologically active fragment, mutant, variant or analog thereof is over-expressed, with or without an N-terminal tag (e.g., octahistidyl-tag), in a vector, such as pIBX1 (Su, et al., Appl. Environ. Microbiol. 62:2723-2734 (1996)) or pET28a (Invitrogen) with an inducible promoter such as with IPTG (isopropyl-beta-D-thiogalactopyranoside), in *E. coli* BLR (DE3)/pLysS (Novagen) or *E. coli* BL21(DE3)/pLysS (Invitrogen) cells. In a specific embodiment, the method of producing prokaryotic PAL comprises: (1) growing a seed culture for a bioreactor/fermenter from a glycerol stock in shake flasks; (2) introducing such seed culture into a controlled bioreactor in fed-batch mode; (3) growing said culture in glucose-supplemented media, pH (7.8), >20% dissolved oxygen, agitation up to 1200 rpm, 30° C. until reaching a cell density of OD600 of 70-100 (~22-25 hrs); (4) inducing said culture with 0.4 mM IPTG; (5) growing said culture at a reduced temperature of 22 to 26° C. until activity change is <0.1 IU/mL (approximately 40-48 hrs and an OD600 typically of 200); and (5) harvesting bacteria by continuous centrifugation. In one embodiment, the cell culture media comprises yeast extract protein, peptone-tryptone, glucose, glycerol, casamino acids, trace salts and phosphate buffering salts.

In a specific embodiment, the recombinant prokaryotic PAL or a biologically active fragment, mutant, variant or analog thereof is an AvPAL variant, and the method of producing the AvPAL variant comprises: (1) growing a seed culture for a bioreactor/fermenter from a glycerol stock of bacteria expressing the AvPAL variant in a shake flask at 37° C. until reaching a cell density of 2 to 4 $OD_{600}$; (2) transferring the seed culture into a first controlled bioreactor (e.g., 4 L fermenter); (3) growing the culture at 37° C. until reaching a cell density of 10 to 20 $OD_{600}$; (4) transferring the first bioreactor (e.g., 4 L fermentation) culture into a second controlled bioreactor (e.g., 100 L fermenter); (5) growing the culture at 37° C. until reaching a cell density of at least 200 $OD_{600}$; (6) cooling the culture to about 15° C.; and (7) separating the bacterial cells from the culture medium by centrifugation. In some embodiments, the method further comprises transferring the second bioreactor (e.g., 100 L fermentation) culture into a third controlled bioreactor (e.g., 500 L fermenter or larger) and growing the culture at 37° C. until reaching a cell density of at least 200 $OD_{600}$, prior to cooling the culture and separating the bacterial cells from the culture medium. In one embodiment, the cysteine residues at positions 503 and 565 of the AvPAL variant have been substituted by serine residues (SEQ ID NO:11).

In a sixth aspect, provided herein is a method to purify prokaryotic PAL or a biologically active fragment, mutant, variant or analog thereof. According to a first embodiment, a transformed cell mass is grown and ruptured leaving crude recombinant enzyme. Exogenous materials can be separated from the crude bulk to prevent fouling of the columns.

Chromatographic purification can be conducted using one or several chromatographic resins. Subsequently, the purified protein can be formulated into a buffer designed to provide stable activity over an extended period of time. In another embodiment, the method to purify the prokaryotic PAL comprises: (a) lysis of the bacteria containing recombinant prokaryotic PAL; (b) treatment of lysate with heat to denature and precipitate E. coli proteins; (c) clarification of this lysate using a second continuous centrifugation step and/or depth filtration; (d) passage of clarified lysate through a charcoal filtration step; (e) passage of filtrate in (d) through an intermediate depth filtration step (as with one or more depth filters, e.g., Pall EKSP, Pall KS50P and/or Pall EKMP filters) followed by a final filtration step (as with a Sartorious Sartopore or Pall EDF 0.2 μm filter); (f) passage of final filtrate over a hydrophobic interaction chromatography resin, such as a butyl hydrophobic interaction chromatography; (g) passage of eluate in (f) over an anionic chromatography resin, such as a Q ion exchange column; (h) recovery of final product, optionally by buffer exchange with tangential flow filtration; and (i) sterilization of the final product. Those skilled in the art readily appreciate that one or more of the chromatography steps can be omitted or substituted, or that the order of the chromatography steps can be changed. Finally, appropriate sterilizing steps can be performed as desired. Also provided herein is a purified prokaryotic PAL or a biologically active fragment, mutant, variant or analog thereof (e.g., produced by the purification methods provided herein), as well as pharmaceutical compositions and formulations thereof, and methods of use thereof.

In a specific embodiment, the recombinant prokaryotic PAL or a biologically active fragment, mutant, variant or analog thereof is a pegylated AvPAL variant with minimal aggregation, and the method of purifying the pegylated AvPAL variant comprises: (a) lysing bacterial cells containing the AvPAL variant by homogenization to generate a cell lysate; (b) heating the cell lysate to 65° C. for 30 to 120 minutes; (c) centrifuging the heated cell lysate, wherein a supernatant comprising the AvPAL variant is retained; (d) filtering the supernatant to remove precipitates; (e) separating the AvPAL variant from contaminating proteins by sequential chromatography over an anion exchange (AIEX) column, such as a Toyopearl Giga Cap Q 650M column, followed by a hydrophobic interaction (HIC) column, such as a Toyopearl Butyl 650M column, wherein the eluate from the HIC column comprises the AvPAL variant; (f) ultrafiltering or ultrafiltering/diafiltering the eluate from the HIC column comprising the AvPAL variant; (g) pegylating the AvPAL variant by mixing polyethylene glycol with the AvPAL variant; (h) removing free polyethylene glycol from the pegylated AvPAL variant by ultrafiltration/diafiltration; and (h) formulating the pegylated AvPAL variant. In an embodiment, the cysteine residues at positions 503 and 565 of said AvPAL variant have been substituted by serine residues (SEQ ID NO:11). In an embodiment, the pegylated AvPAL variant comprises polyethylene glycol. In an embodiment, the pegylated AvPAL variant comprises polyethylene glycol, wherein the ratio of AvPAL variant and the polyethylene glycol is about 1:3. In an embodiment, the AIEX column is a Toyopearl Giga Cap Q 650M column. In an embodiment, the HIC column is a Toyopearl Butyl 650M column.

In an embodiment, the method of purifying the pegylated AvPAL variant further comprises freezing and thawing the eluate from the HIC column comprising the AvPAL variant, wherein one or more polyols or sugars, such as about 2.5%, 5%, 7.5%, 10%, 12.5% or 15% glycerol, sucrose, glucose, trehalose, mannitol or sorbitol, or the like is added to the HIC column eluate prior to freezing. In an embodiment, the polyol is glycerol. In an embodiment, the concentration of glycerol is 10% (v/v). In an embodiment, the sugar is sucrose. In an embodiment, the concentration of sucrose is 10% (v/v). In an embodiment, the method of purifying the pegylated AvPAL variant further comprises concentrating the eluate from the HIC column comprising the AvPAL variant by ultrafiltration up to about 16× or more (e.g., about 2×, 3×, 4×, 5×, 6×, 8×, 10×, 12×, 14×, 16×, 18×, 20×, or 25×) prior to freezing. In an embodiment, the eluate from the HIC column comprising the AvPAL variant is frozen using discrete temperature steps. In an embodiment, the eluate from the HIC column comprising the AvPAL variant is thawed using discrete temperature steps. In an embodiment, the eluate from the HIC column comprising the AvPAL variant is frozen and thawed using discrete temperature steps. In an embodiment, the eluate from the HIC column comprising the AvPAL variant is diafiltered in a diafiltration buffer comprising potassium phosphate (KPi) and one or more agents that reduce aggregation and/or preserve enzyme activity upon pegylation, such as trans-cinnamic acid (t-CA) and glycerol. In an embodiment, the diafiltration buffer comprises 50 mM KPi, 10 mM t-CA, 5% glycerol, pH 8.5. In an embodiment, a non-ionic detergent, such as polysorbate 80 (PS80), is added to the ultrafiltered/diafiltered eluate from the HIC column comprising the AvPAL variant. In an embodiment, the non-ionic detergent is PS80. In an embodiment, the concentration of PS80 is 0.02% (v/v). Also provided herein are pegylated AvPAL variants with minimal aggregation, (e.g., produced by the purification methods provided herein), as well as pharmaceutical compositions and formulations thereof, and methods of use thereof.

In a specific embodiment, the recombinant prokaryotic PAL or a biologically active fragment, mutant, variant or analog thereof is an AvPAL variant with minimal aggregation, and the method of purifying the AvPAL variant comprises: (a) lysing bacterial cells containing the AvPAL variant by homogenization to generate a cell lysate; (b) heating the cell lysate to 65° C. for 30 to 120 minutes; (c) centrifuging the heated cell lysate, wherein a supernatant comprising the AvPAL variant is retained; (d) filtering the supernatant to remove precipitates; and (e) separating the AvPAL variant from contaminating proteins by sequential chromatography over an AIEX column, such as Toyopearl Giga Cap Q 650M, followed by a hydrophobic interaction HIC column, such as Toyopearl Butyl 650M, wherein the eluate from the HIC column comprises the AvPAL variant. In an embodiment, the cysteine residues at positions 503 and 565 of said AvPAL variant have been substituted by serine residues (SEQ ID NO:11) In an embodiment, the AIEX column is a Toyopearl Giga Cap Q 650M column. In an embodiment, the HIC column is a Toyopearl Butyl 650M column. Also provided herein are AvPAL variants with minimal aggregation, (e.g., produced by the purification methods provided herein), as well as pharmaceutical compositions and formulations thereof, and methods of use thereof.

In a seventh aspect, provided herein are screening assays and methods thereof for identifying prokaryotic PAL or a biologically active fragment, mutant, variant or analog thereof that can prevent, ameliorate, or treat enhanced levels of phenylalanine by contacting a cell containing elevated levels of phenylalanine with the bacterial PAL and determining whether the bacterial PAL reduces such elevated levels of phenylalanine. Such screening assays can also include the steps of creating variants that include conservative or non-conservative substitutions in the active sites, e.g., Gly142, Thr-Ser-Gly triad (143-145), Asp146, Leu147, Asn196, Ile195, Leu192, Leu76, Asn79, Met400, Thr428, Gln432 in EncP from *Streptomyces maritimus*, or their equivalents in other prokaryotic PAL, such as *Nostoc punctiforme* or *Anabaena variabilis*, which are equivalent to residues Ser210, Ala-Ser-Gly triad (211-213), Asp214, Leu215, Asn270, Val269, Leu266, Leu134, His137, Lys468, Glu496, Gln500 in PAL from *Rhodosporidium toruloides* (RtPAL), in regions adjacent to the active sites, or throughout the polypeptide sequence, followed by testing the variants for in vitro phenylalanine converting activity. In certain embodiments, the method is a high throughput assay. In one embodiment, complete genomes of the bacterial species are sequenced and screened for the presence of prokaryotic PAL homologs using a bioinformatics approach. In another embodiment, PAL catalytic activity of the protein product of such homologs is confirmed, such as by testing ability to convert phenylalanine to trans-cinnamate in vitro.

In an eighth aspect, provided herein are methods of using prokaryotic PAL compositions for the diagnosis of diseases, including but not limited to disorders caused all or in part by a deficiency in PAH activity. In one embodiment, prokaryotic PAL is used to measure levels of Phe in blood, plasma or serum samples. Also provided herein is a diagnostic kit comprising prokaryotic PAL for use in monitoring blood, plasma or serum samples of subjects for levels of Phe.

Other features and advantages of the compositions and methods provided herein will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

DESCRIPTION OF THE FIGURES

FIGS. 1A-1B show the gene sequence and the protein sequence of *Nostoc punctiforme* PAL. (A) Gene sequence of *Nostoc punctiforme* PAL (SEQ ID NO:1); (B) Protein sequence of *Nostoc punctiforme* PAL (SEQ ID NO:2).

FIGS. 2A-2B show the gene sequence and the protein sequence of *Anabaena variabilis* PAL. (A) Gene sequence of *Anabaena variabilis* PAL (SEQ ID NO:3); (B) Protein sequence of *Anabaena variabilis* PAL (SEQ ID NO:4).

FIG. 4 Alignment of cyanobacterial protein sequences of *N. punctiforme* PAL (SEQ ID NO:2) and *A. variabilis* PAL (SEQ ID NO:4) with EncP PAL (SEQ ID. No. 5) and *P. putida* HAL (SEQ ID NO:6). Active site residues, which correspond to PAL or HAL activity, are highlighted.

FIGS. 5A-5E show the protein sequence of *Anabaena variabilis* phenylalanine ammonia-lyase (PAL) with a cysteine to serine substitution at various positions. (A) Protein sequence of *Anabaena variabilis* phenylalanine ammonia-lyase (PAL) with a cysteine to serine substitution at position 64 (AvPAL_C64S, SEQ ID NO:7); (B) Protein sequence of *Anabaena variabilis* PAL with a cysteine to serine substitution at position 318 (AvPAL_C318S, SEQ ID NO:8); (C) Protein sequence of *Anabaena variabilis* PAL with a cysteine to serine substitution at position 503 (AvPAL_C503S, SEQ ID NO:9); (D) Protein sequence of *Anabaena variabilis* PAL with a cysteine to serine substitution at position 565 (AvPAL_C565S, SEQ ID NO:10); (E) Protein sequence of *Anabaena variabilis* PAL with cysteine to serine substitutions at positions 503 and 565 (AvPAL_C565SC503S, SEQ ID NO:11). Cysteine to serine substitutions are underlined in bold.

Figure 15A:
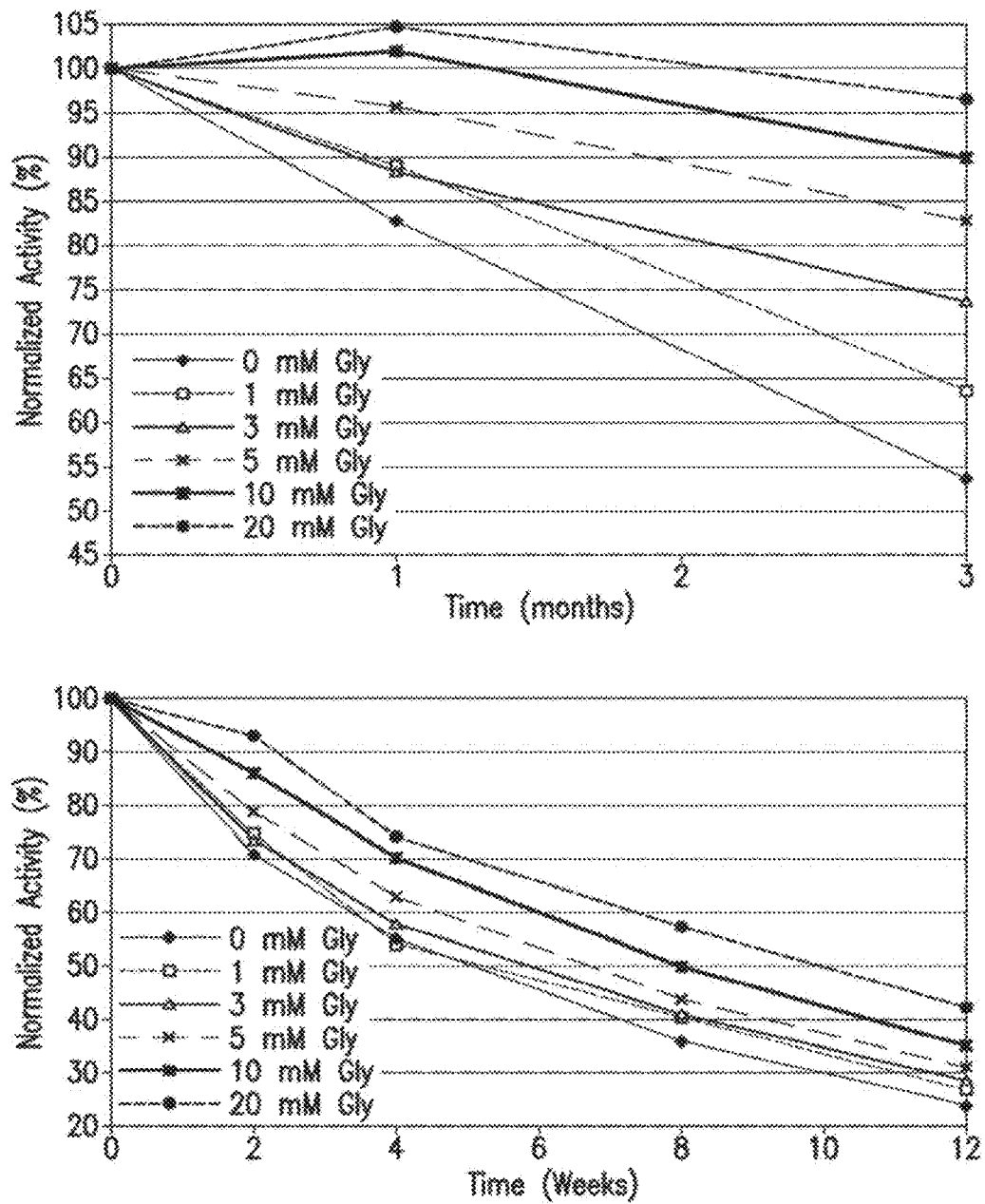
Figure 15B:
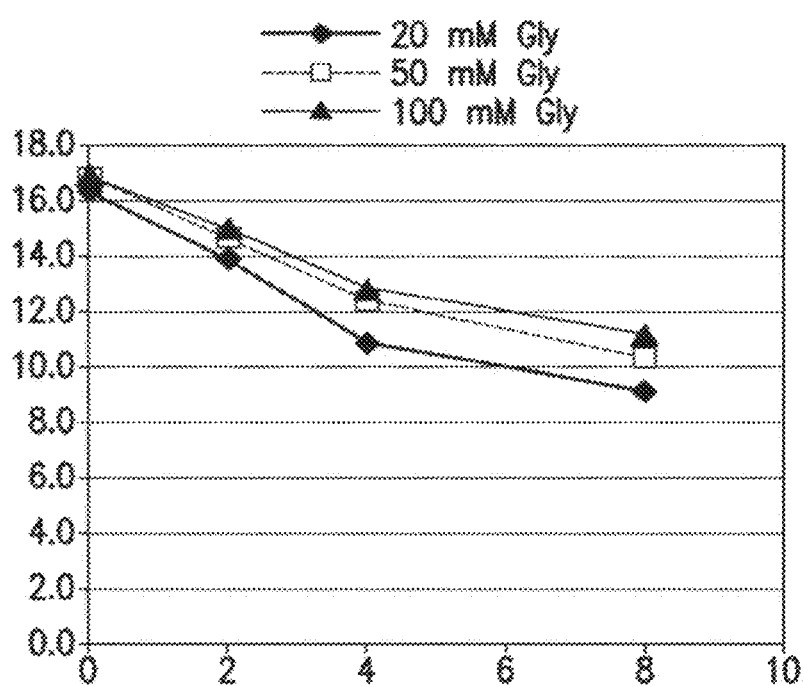

FIGS. 15A-15B show effect of glycine (Gly) at different concentrations on the enzyme activity of a pegylated AvPAL variant. (A) Effect of glycine (Gly) at 1 to 20 mM as indicated on the normalized activity (%) of a pegylated AvPAL with cysteine to serine substitutions at positions 565 and 503 (AvPAL_C565SC503S) stored for various times (weeks or months as indicated) at 25° C. (top panel) and at 40° C. (bottom panel). (B) Effect of glycine (Gly) at 20, 50 or 100 mM as indicated on the enzyme activity (U/mL) of a pegylated AvPAL with cysteine to serine substitutions at positions 565 and 503 (AvPAL_C565SC503S) stored for various times (weeks as indicated) at 40° C.

Figure 16:
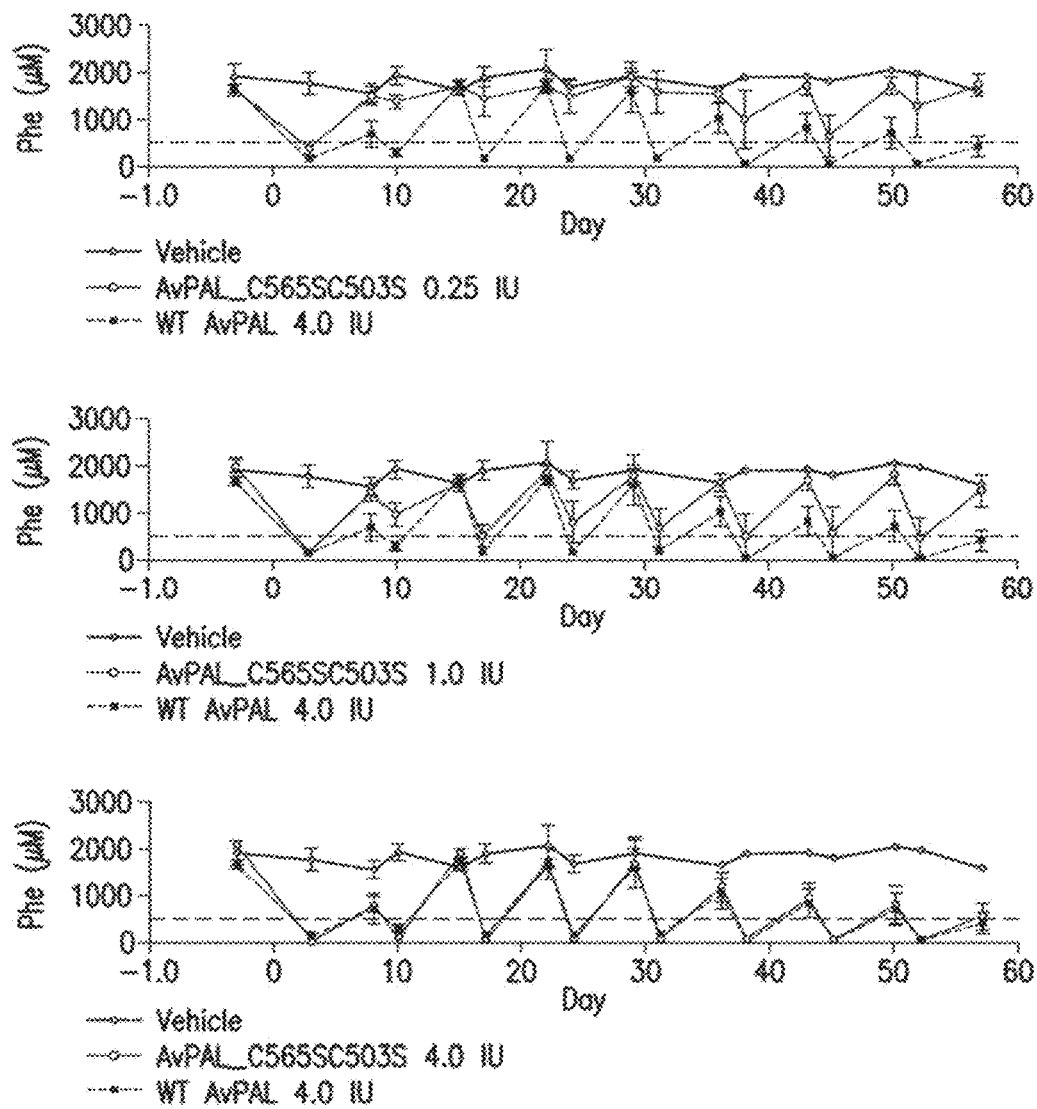

FIG. 16 Effect of cysteine to serine substitutions at positions 565 and 503 (AvPAL_C565SC503S) in pegylated AvPAL on in vivo Phe levels in ENU2 mice dosed with 0.25 IU (top panel), 1.0 IU (middle panel) or 4.0 IU (bottom panel) enzyme as compared to ENU2 mice dosed with vehicle or 4.0 IU wild-type pegylated AvPAL.

Figure 17:
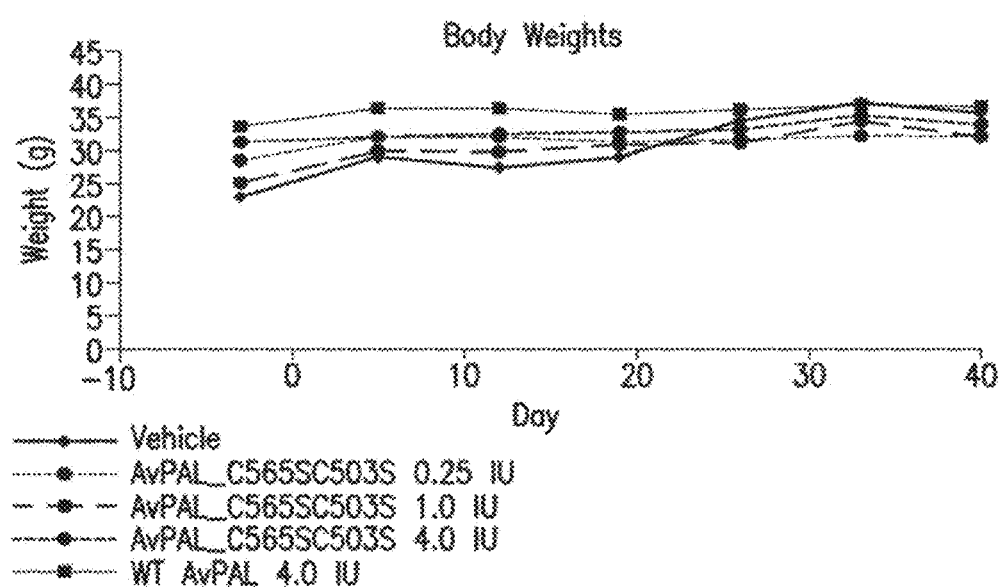
Figure 18:
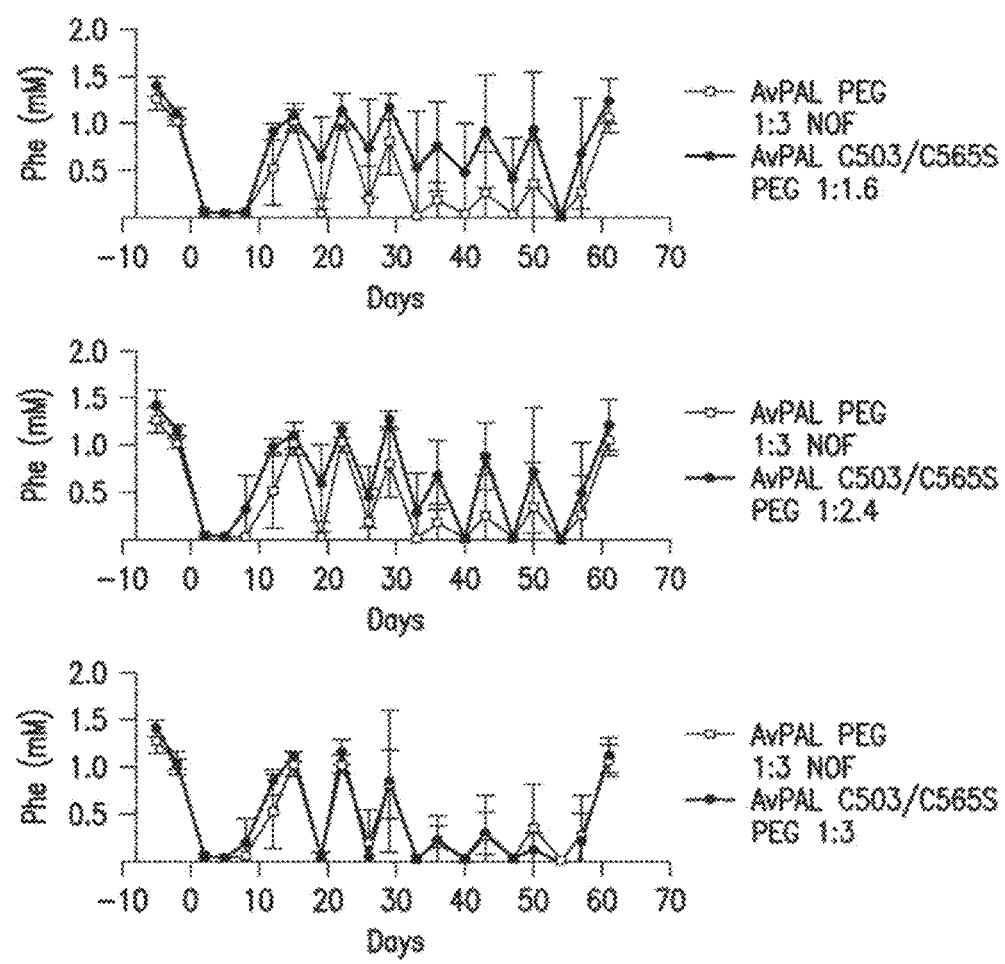

FIG. 17 Effect of cysteine to serine substitutions at positions 565 and 503 (AvPAL_C565SC503S) in pegylated AvPAL on body weights of ENU2 mice dosed with 0.25 IU, 1.0 IU or 4.0 IU enzyme as compared to ENU2 mice dosed with vehicle or 4.0 IU wild-type pegylated AvPAL FIG. 18 Effect of cysteine to serine substitutions at positions 565 and 503 (AvPAL C503S/565S) in pegylated AvPAL on in vivo Phe levels in ENU2 mice dosed with 4 IU enzyme at various AvPAL:PEG ratios: 1:1.6 (top panel), 1:2.4 (middle panel) or 1:3 (bottom panel), as compared to ENU2 mice dosed with vehicle or 4.0 IU wild-type pegylated AvPAL at an AvPAL:PEG ratio of 1:3.

Figure 19:
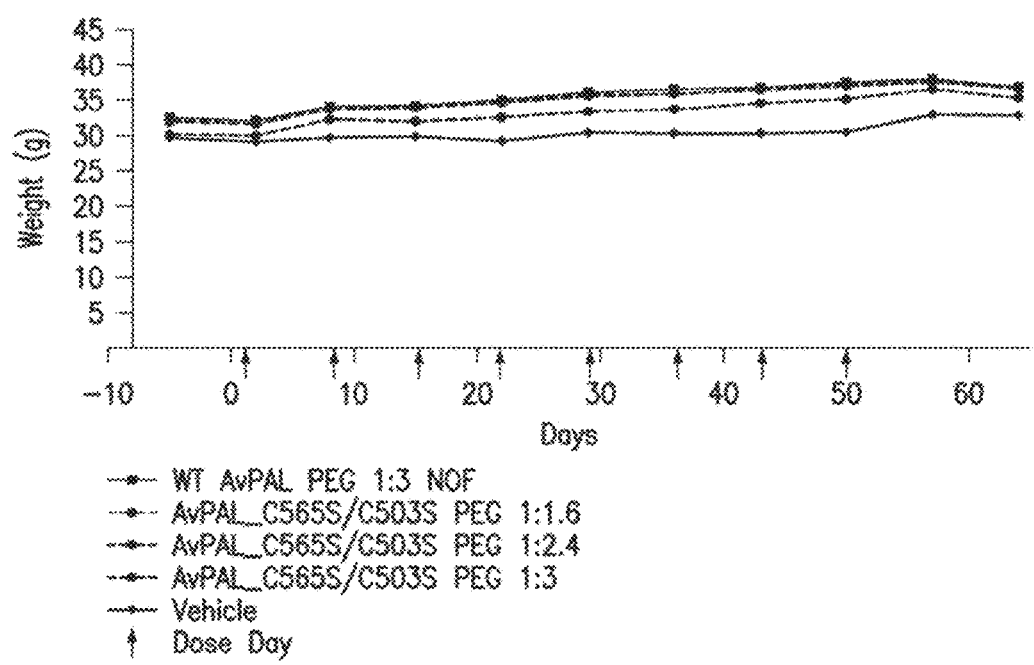

FIG. 19 Effect of cysteine to serine substitutions at positions 565 and 503 (AvPAL_C565SC503S) in pegylated AvPAL on body weights of ENU2 mice dosed with 4 IU enzyme at various AvPAL:PEG ratios: 1:1.6, 1:2.4 or 1:3, as compared to ENU2 mice dosed with vehicle or 4.0 IU wild-type pegylated AvPAL at an AvPAL:PEG ratio of 1:3.

Figure 20A:
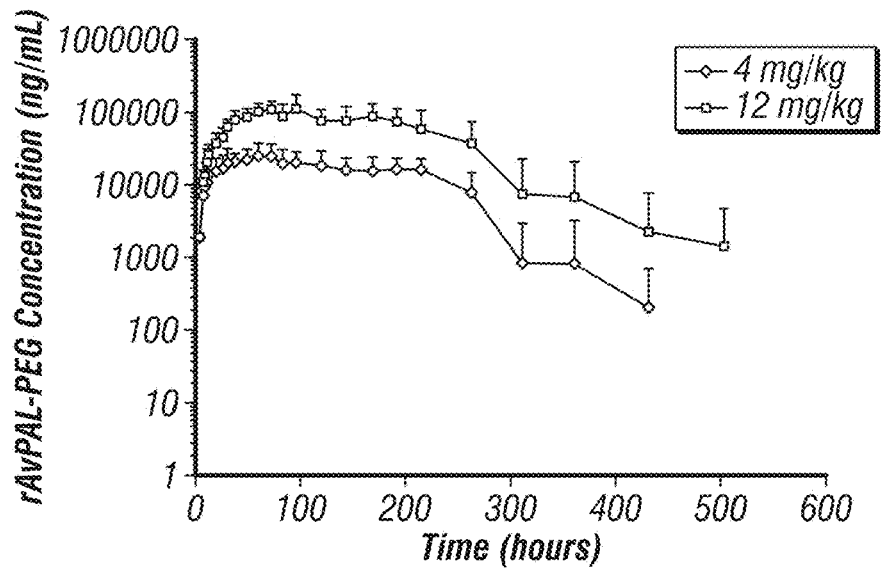
Figure 20B:
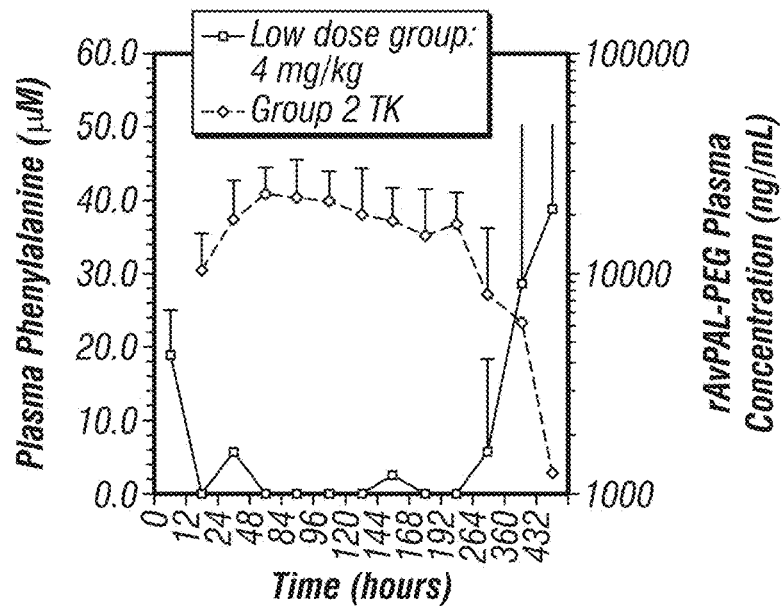

FIGS. 20A-20B show the pharmacokinetic effect of a single subcutaneous injection of a pegylated AvPAL variant at different dosages into Cynomolgus monkeys. (A) Effect of a single subcutaneous injection of a pegylated AvPAL with cysteine to serine substitutions at positions 565 and 503 (AvPAL_C565SC503S) at 4 mg/kg (diamonds) and at 12 mg/kg (squares) into Cynomolgus monkeys on the plasma AvPAL_C565SC503S levels over time (hours). (B) Effect of a single subcutaneous injection of AvPAL_C565SC503S at 4 mg/kg into Cynomolgus monkeys on the plasma AvPAL_C565SC503S (diamonds) and phenylalanine (squares) levels over time (hours).

Figure 21A:
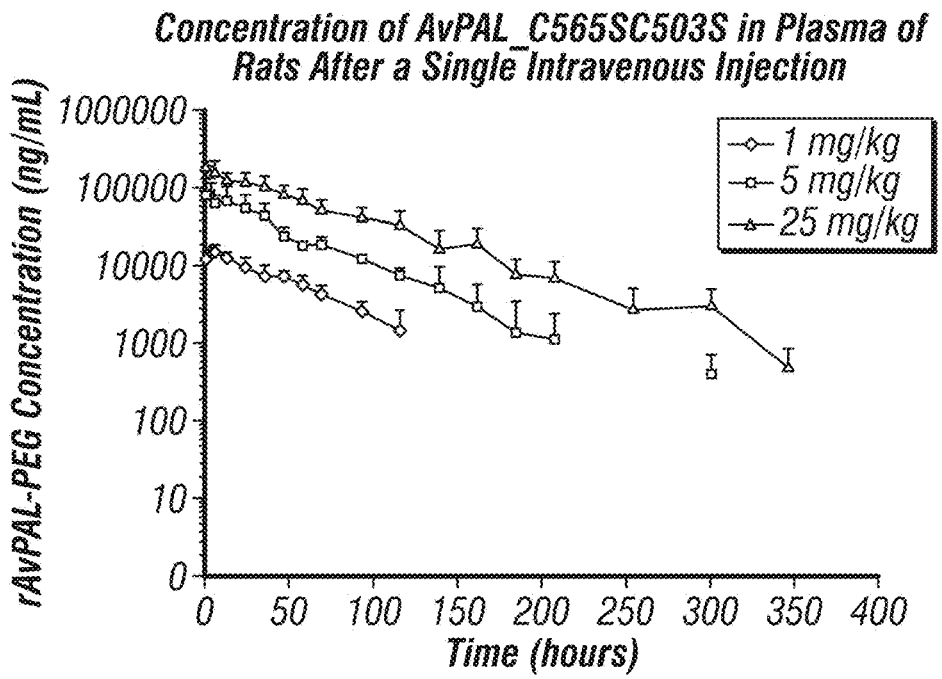
Figure 21B:
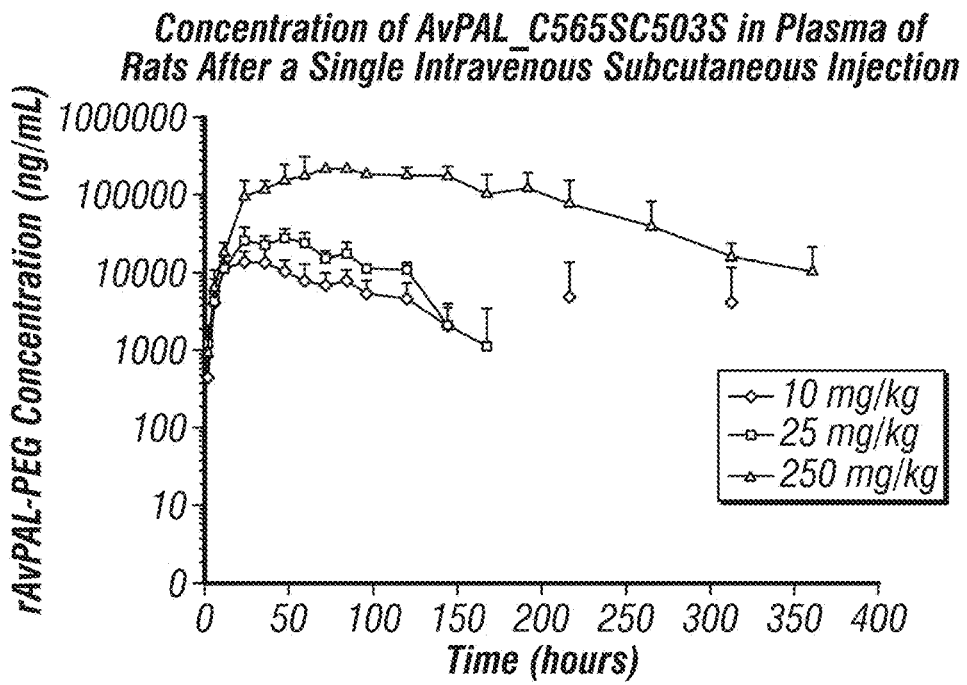

FIGS. 21A-21B show the pharmacokinetic effect of a single intravenous or subcutaneous injection of a pegylated AvPAL variant at different dosages into rats. (A) Effect of a single intravenous injection of a pegylated AvPAL with cysteine to serine substitutions at positions 565 and 503— ( AvPAL_C565SC503S) at 1 mg/kg (diamonds), at 5 mg/kg (squares) and at 25 mg/kg (triangles) into rats on the plasma AvPAL_C565SC503S levels over time (hours). (B) Effect of a single subcutaneous injection of AvPAL_C565SC503S at 10 mg/kg (diamonds), at 25 mg/kg (squares) and at 250 mg/kg (triangles) into rats on the plasma AvPAL_C565SC503S levels over time (hours).

Figure 22:
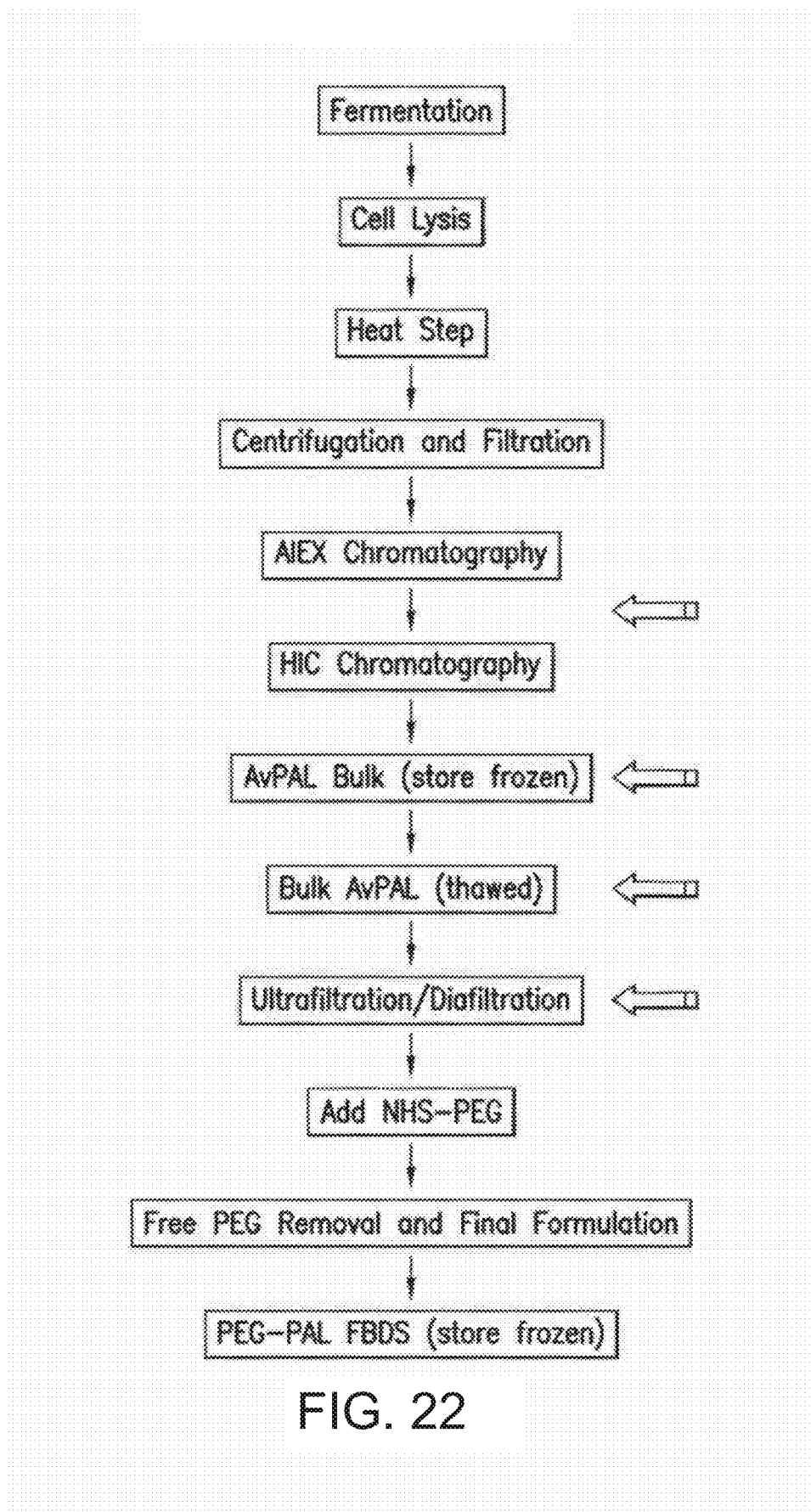

FIG. 22 Flow diagram of production process for large scale manufacturing of a pegylated AvPAL variant polypeptide with minimal aggregation. Leftward pointing arrows indicate process steps that are targets for reducing aggregation.

DETAILED DESCRIPTION

Provided herein are compositions of prokaryotic PAL and biologically active fragments, mutants, variants or analogs thereof and their use for therapeutic purposes, including the treatment of hyperphenylalaninemia, including phenylketonuria, and other disorders, including cancer.

A. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms can be found in reference works, including Carey and Sundberg, Advanced Organic Chemistry, $3^{rd}$ Edition, Vols. A and B (Plenum Press, New York 1992). The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., $4^{th}$ Edition, 2004); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide-binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

"Recombinant polynucleotide" refers to a polynucleotide having sequences that are not naturally joined together. An amplified or assembled recombinant polynucleotide can be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide can serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but can be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Amino acids can also be grouped as follows:
(1) hydrophobic: Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using a sequence comparison algorithm described in prior co-pending U.S. patent application Ser. No. 11/230,374 filed on Sep. 19, 2005, which is herein incorporated by reference in its entirety, or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. The substantial identity can exist over a region of the sequences that is at least about 50 residues in length, such as over a region of at least about 100 residues, or over a region of at least about 150 residues. In certain embodiments, the sequences are substantially identical over the entire length of either or both comparison biopolymers.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the prokaryotic PAL variant compositions are substantially pure or isolated. In some embodiments, the prokaryotic PAL variant compositions are substantially pure or isolated with respect to the macromolecular starting materials used in their synthesis. In some embodiments, the pharmaceutical compositions comprise a substantially purified or isolated prokaryotic PAL variant admixed with one or more pharmaceutically acceptable excipient.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally occurring.

"Wild-type" (wt) is a term referring to the natural genetic form of an organism. A wild-type is distinguished from a mutant form (an organism with a genetic mutation).

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, "polypeptide" as used herein refers to a protein, which includes modifications, such as deletions, additions and substitutions (generally conservative in nature), to the native sequence, so long as the protein maintains the desired activity. Such polypeptides may be referred to as "mutants" herein. These modifications can be deliberate, as through site-directed mutagenesis, or can be accidental, such as through mutations arising with hosts that produce the proteins or errors due to PCR amplification.

As used herein, "variant," "analog," or "derivative" is a compound, e.g., a peptide, having more than about 70% sequence but less than 100% sequence similarity with a given compound, e.g., a peptide. Such variants, analogs or derivatives can be comprised of non-naturally occurring amino acid residues, including by way of example and not limitation, homoarginine, ornithine, penicillamine, and norvaline, as well as naturally occurring amino acid residues. Such variants, analogs or derivatives can also be composed of one or a plurality of D-amino acid residues, and can contain non-peptide interlinkages between two or more amino acid residues.

As used herein, the "ratio" of a PAL polypeptide (e.g., AvPAL) and a water-soluble polymer (e.g., polyethylene glycol or PEG) refers to the reaction condition molar ratio between the PAL polypeptide and the water-soluble polymer. For example, a ratio of about 1:3 for AvPAL and polyethylene glycol (1:3 AvPAL:PEG) means that the chemically modified PAL was produced in a reaction condition with about 1 mol lysine residue on the AvPAL per 3 mol of polyethylene glycol. Because an AvPAL monomer has 18 lysine residues, a ratio of about 1:3 AvPAL:PEG corresponds to 1 mol AvPAL per 54 mol PEG in the pegylation reaction. Under the reaction conditions described in EXAMPLE 6, infra, a ratio of about 1:3 AvPAL:PEG results in about 10-12 mol PEG per mol AvPAL monomer.

"Treatment" or "treating" as used herein refers to prophylactic treatment or therapeutic treatment or diagnostic treatment.

A "prophylactic" treatment is a treatment administered to a subject who does not exhibit signs of disease or pathology, i.e., a cancer, or exhibits only early signs for the purpose of decreasing the risk of developing pathology. The prokaryotic PAL compositions, including formulations, provided herein can be given as a prophylactic treatment to reduce the likelihood of developing a pathology, i.e., a cancer, or to minimize the severity of the pathology, if developed.

A "therapeutic" treatment is a treatment administered to a subject who exhibits signs or symptoms of pathology, i.e., a cancer, for the purpose of diminishing or eliminating those signs or symptoms. The signs or symptoms can be biochemical, cellular, histological, functional, subjective or objective.

The prokaryotic PAL compositions can be given as a therapeutic treatment or for diagnosis.

"Diagnostic" means identifying the presence or nature of a pathologic condition, i.e., a cancer. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a prokaryotic PAL polypeptide and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions encompass any composition made by admixing a prokaryotic PAL polypeptide provided herein and a pharmaceutically acceptable carrier.

"Pharmaceutically acceptable carrier" refers to any of the standard pharmaceutical excipients, vehicles, diluents, stabilizers, preservatives, solubilizers, emulsifiers, adjuvants and/or carriers, such as, for example and not for limitation, a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Pharmaceutical carriers to be used can depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a prokaryotic PAL variant composition for pharmaceutical use including, e.g., metal salts (sodium, potassium, magnesium, calcium, etc.) and salts of ammonia or organic amines.

By "pharmaceutically acceptable" or "pharmacologically acceptable" is meant a material which is not biologically or otherwise undesirable, i.e., the material can be administered to an individual without causing any undesirable biological effects or interacting in a deleterious manner with any of the components of the composition in which it is contained.

The term "unit dosage form," as used herein, refers to physically discrete units suitable as unitary dosages for human and animal subjects, each unit containing a predetermined quantity of prokaryotic PAL variant calculated in an amount sufficient to produce the desired effect in association with a pharmaceutically acceptable diluent, carrier or vehicle. The specifications for the novel unit dosage forms can depend on the particular prokaryotic PAL variant employed and the effect to be achieved, and the pharmacodynamics associated with each prokaryotic PAL variant in the host.

By "physiological pH" or a "pH in the physiological range" is meant a pH in the range of approximately 7.2 to 8.0 inclusive, more typically in the range of approximately 7.2 to 7.6 inclusive.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

B. Prokaryotic PAL Variants

The elucidation of a reliable three-dimensional structure or structural model for a specific macromolecule permits rational design to become a productive method for optimization of specific structure and/or function of said macromolecule. Methods of using a three-dimensional structure or structural model for optimizing PAL enzymes are described in prior co-pending U.S. patent application Ser. No. 11/230,374 filed on Sep. 19, 2005, which is herein incorporated by reference in its entirety. A high-resolution three-dimensional protein crystal structure of a prokaryotic PAL can be used in methods involving protein engineering to improve the biochemical and biophysical properties of a prokaryotic PAL, and to increase the in vivo therapeutic effectiveness of a prokaryotic PAL. Provided herein are prokaryotic PAL variants with greater phenylalanine-converting activity and/or reduced immunogenicity as compared to a wild-type prokaryotic PAL. Also provided herein are prokaryotic PAL variants with greater biochemical stability and/or biochemical half-life as compared to a wild-type prokaryotic PAL.

Previous experiments have described modified forms of PAL, such as PAL mutants (Schuster, et al., FEBS Lett. 349(2):252-254 (1994); Schuster, et al., Proc Natl Acad Sci USA 92(18):8433-8437 (1995); Langer, et al., Biochemistry 36:10867-10871 (1997); El-Batal, et al., Acta Microbiol Pol. 49(1):51-61 (2000); Rother, et al., Eur. J. Biochem. 269:3065-3075 (2002)) and HAL mutants (Taylor, et al., J. Biol. Chem. 269(44):27473-27477 (1994); Baedeker, et al., Eur. J. Biochem. 269(6):1790-1797 (2002)).

Prokaryotic PAL Variants with Enhanced Catalytic Activity

The biologically active sites of wild-type PAL provided herein can be modified to optimize PAL kinetic characteristics. $K_m$, the concentration of substrate that gives half-maximal activity, is intimately associated with the therapeutic efficacy of PAL in maintaining Phe levels within an acceptable range, i.e., 120 μM to 240 μM. $K_m$ is the affinity of the enzyme for the substrate. By controlling affinity, one can limit or control the efficacy of any enzyme against substrate at different concentrations. For example, if $K_m$ is 1000 μM (e.g., PAL from *Rhodosporidium toruloides*), the activity of the enzyme will be reduced to about 12.5% at blood Phe levels of 240 μM and to about 3% at blood Phe levels of 60 μM. If $K_m$ is 240 μM, the activity of the enzyme will be reduced to about 50% at blood Phe levels of 240 μM and to about 12% at blood Phe levels of 60 μM. If $K_m$ is 120 μM, the activity of the enzyme will be reduced to about 70% at blood Phe levels of 240 μM and to about 35% at blood Phe levels of 60 μM. Optimally, a therapeutic objective would be to have an enzyme with sufficient activity to reduce but also maintain Phe within the optimal range of about 120 μM to about 240 μM. An enzyme with a high $K_m$ (i.e., 1000 μM) will lose activity rapidly as Phe levels drop to within normal range and will also require the impractical administration of highly concentrated or large volumes of doses. On the other hand, an enzyme with a very low $K_m$ can rapidly deplete Phe levels, which may be fatal for hyperphenylaninemias, but can be useful in the management of cancer.

In some embodiments, the biologically active modified PAL has a kcat of at least about 0.1 s-1 or greater than about 0.5 s-1. In other embodiments, the biologically active modified PAL has a kcat of at least about 0.2 s-1 or greater than about 1.0 s-1. In other embodiments, the biologically active modified PAL has a Km of between about 10 µM to about 1000 µM. In other embodiments, the biologically active modified PAL has a Km of between about 100 µM to about 1000 µM. In other embodiments, the biologically active modified PAL exhibits enzymatic activity that is from about two-fold to about 1000-fold times greater that that of the wild-type. In other embodiments, the biologically active modified PAL exhibits enzymatic activity that is from about 10% to about 100% higher than that of the wild-type. Such biological active modified PAL proteins can be formed using methods well known in the art, such as by site-directed mutagenesis.

All active site residues in HAL were shown to be present in EncP except for H83 and E414, which are replaced with valine and glutamine residues, respectively (Xiang, L., et al., J. Biol. Chem. 277:32505-32509 (2002)). The role of H83 in HAL in binding and orientating the imidazole moiety of L-histidine at the active site and in stabilizing an enzyme-bound cationic intermediate was investigated (Xiang, et al., J. Bacteriology 187(12):4286-4289 (2005); Xiang, et al., J. Bacteriology 188(14):5331 (2006)). It was proposed that the carboxylate group of E414 may act as a base in catalysis. In the study, EncP mutants were generated by site-directed mutagenesis to assess the contribution of V83 to cinnamic acid formation by EncP. Replacement of valine with histidine generated a mutant, V83H, which was characterized by a loss in PAL activity. Replacement of the valine with alanine resulted in a mutant, V83A, which was more active than the wild-type EncP V83A, had a slightly lower affinity to L-phenylalanine with a Km of 120 µM versus 23 µM for the wild-type enzyme. However, in comparison with wild-type EncP, V83A had a higher kcat higher and was more active than the wild-type enzyme.

Prokaryotic PAL Variants Having Reduced Immunogenicity

A number of strategies are currently used to reduce protein immunogenicity. In certain embodiments, modifications that are introduced to minimize the immune response do not destroy the structure, function, or stability of the macromolecule. Effective strategies used include increasing human sequence content (chimeras and/or other 'humanization' approaches), improving solution properties, removing antibody epitopes, introducing chemical derivatization (such as pegylation), and/or identifying and removing MHC agretopes. For an injected therapeutic, in vivo immunoreactivity can be addressed by performing epitope mapping followed by rational mutagenesis to modify and/or otherwise mutate these sites of immunogenicity, alone and in combination with site-specific pegylation (Hershfield, et al., Proc. Natl. Acad. Sci. USA 88:7185-7189 (1991); Leong, et al., Cytokine 16(3):106-119 (2001); Lee, et al., Pharm. Res. 20(5):818-825 (2003)) or other chemical derivatization methods to reduce protein immunoreactivity to an acceptable level. Modification of antigenic surface protein regions reduces immunogenicity (Chirino, et al., Drug Discov. Today 9(2):82-90 (2004)). One method of improvement involves the construction of smaller sized proteins that retain catalytic activity (e.g., an absorbance assay is used for activity measurement). Protein engineering coupled to ELISA screening, can also be used to identify mutants with reduced immunoreactivity. Another method introduces point mutations for additional surface Lys sites for pegylation derivatization, a method shown to reduce immunogenicity with the test enzyme purine nucleoside phosphorylase (Hershfield, et al. (1991), ibid.). An alternative pathway uses mutation of residues located in protein epitope regions to remove immunogenic sites (Yeung, et al., J. Immunol. 172(11):6658-6665 (2004)). In an approach that is analogous to antibody humanization, homologous loop regions and/or residues from human antibodies are substituted into the corresponding loop regions of a homologous protein.

Improving solution properties of proteins can increase specific enzyme activity and/or reduce immunogenicity. One solution property typical of bacterially expressed recombinant proteins is the formation of protein aggregates due, for example, to inter-chain disulfide bind formation, hydrophobic interactions and/or divalent cations (Chi, et al., Pharm. Res. 20(9):1325-1336 (2003)). Aggregation of recombinantly expressed proteins can enhance the immune response (Hermeling, et al., Pharm. Res. 21(6):897-903 (2994); Schellekens, Nephrol. Dial. Transplant. 20(suppl 6):vi3-9 (2005)). One method of improvement involves substituting surface cysteine residues with other amino acid residues (e.g., serine) to minimize the possibility of formation of inter-chain disulfide bonds. For example, substitution of two surface cysteine residues with serine residues reduced the aggregation of chorismate lyase with minor effects on enzyme activity (Holden, et al., Biochim. Biophys. Acta 1594(1):160-167 (2002)).

Provided herein are prokaryotic PAL variants having one or more cysteine residues substituted by another amino acid residue, such as a serine residue. In some embodiments, one or more cysteine residues of the prokaryotic PAL are substituted by another amino acid residue. In certain embodiments, the prokaryotic PAL is AvPAL. In specific embodiments, one or more cysteine residues of AvPAL are substituted by a cysteine residue.

C. Chemically Modified Prokaryotic PAL Variants

Macromolecule chemical modification can be performed in a non-specific fashion (leading to mixtures of derivatized species) or in a site-specific fashion (based on wild-type macromolecule reactivity-directed derivatization and/or site-selective modification using a combination of site-directed mutagenesis and chemical modification) or, alternatively, using expressed protein ligation methods (Hofmann, et al., Curr. Opin. Biotechnol. 13(4):297-303 (2002)). In certain embodiments, chemical modification is used to reduce immunogenicity. Pegylation is a demonstrated method to reduce immunogenicity of proteins (Bhadra, et al., Pharmazie 57(1):5-29 (2002)), but glycosylation and other chemical derivatization procedures, using modification with phosphorylation, amidation, carboxylation, acetylation, methylation, creation of acid-addition salts, amides, esters, and N-acyl derivatives are also possible (Davis, Science 303:480-482 (2004)).

Pegylated Proteins

A series of different pegylation reactions on PAL, using a range of PEG chemical reagent to PAL protein ratios, will provide PEG-PAL derivatives for each modification method. The optimal degree of pegylation can be determined based upon the residual activity obtained for each derivatized PAL species using the absorbance assay in combination with PAGE and native gel analysis, or by using SE-HPLC with multiangle light scattering (MALS), to determine the extent of PEG derivatization. After initial ranges of optimal modification are determined, comparative kinetic analysis (including Vmax and Km determinations, binding constants of substrates, proteolytic stability, pH dependence of activity, temperature-dependence of activity) and immunoreactivity of optimal PEG-PAL species can be determined by ELISA, immunoprecipitation, and Western blot. Protein engineering can also be used to generate the most favorable PAL mutant for pegylation using the optimal derivatization conditions; by minimizing the size of the PAL protein and only modifying the most antigenic regions of the PAL surface, cost of PEG modification will be reduced while at the same time retaining the maximum amount of enzymatic activity and minimum amount of immunogenicity. Similarly, site-specific pegylation can be used to provide enzyme derivatives.

Other chemical modifications such as phosphorylation or other chemical modification of Lys, Arg, and Cys residues can be used to mask immunogenic regions and/or proteolytic sensitive regions. Such chemical modifications include the polymer addition method of Bednarsaki and the Altus Corporation cross-linking method for improving PAL stability, reducing immunogenicity, and improving protease resistance are representative examples. Bednarsaki demonstrated that polymer addition improves protein temperature stability (Wang, et al., J. Am. Chem. Soc. 114(1):378-380 (1992)), and Altus Corporation has found that glutaraldehyde cross-linking improves enzyme stability.

To discover if the in vivo therapeutic half-life of a protein such as PAL would benefit from pegylation, a variety of different PEG:PAL conjugates are synthesized, characterized in vitro and tested in vivo for L-Phe reduction. In order to both optimize the potential effects of pegylation and to identify one or more sites of PEG attachment, a design strategy is employed wherein polymer length, conformation, and the degree of PEG attachment is varied. In some embodiments, methods for preparing the pegylated PAL generally comprise: (a) reacting PAL with polyethylene glycol under conditions whereby PAL becomes attached to one or more PEG groups, and (b) obtaining the reaction product(s). Because the specific sites of PAL modification might significantly alter the intrinsic activity of the conjugate, different types and amounts of PEG were explored. The chemistry used for pegylation of PAL was the acylation of the primary amines of PAL using the NHS-ester of methoxy-PEG (O-[(N-Succinimidyloxycarbonyl)-methyl]-O'-methyl-polyethylene glycol). Acylation with methoxy-PEG-NHS or methoxy-PEG-SPA results in an amide linkage that eliminates the charge from the original primary amine.

The present methods provide for a substantially homogenous mixture of polymer:protein conjugate. "Substantially homogenous" as used herein means that only polymer: protein conjugate molecules are observed. The polymer: protein conjugate has biological activity and the present "substantially homogenous" pegylated PAL preparations provided herein are those which are homogenous enough to display the advantages of a homogenous preparation, e.g., ease in clinical application in predictability of lot to lot pharmacokinetics.

The polymer molecules contemplated for use in the pegylation approaches described herein can be selected from among water-soluble polymers or a mixture thereof. The water-soluble polymer can be selected from the group consisting of, for example, polyethylene glycol, monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), HPMA, Fleximer™, and polyvinyl alcohol, mono-(C1-C10)alkoxy-PEG, aryloxy-PEG, tresyl monomethoxy PEG, PEG propionaldehyde, bis-succinimidyl carbonate PEG, cellulose, or other carbohydrate-based polymers. The polymer selected should be water-soluble so that the protein to which it is attached does not precipitate in an aqueous environment, such as a physiological environment. The polymer can be branched or unbranched. In some embodiments, for therapeutic use of the end-product preparation, the polymer will be pharmaceutically acceptable.

In some embodiments, a water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

The proportion of polyethylene glycol molecules to protein molecules will vary, as will their concentrations in the reaction mixture. In general, the optimum ratio (in terms of efficiency of reaction in that there is no excess unreacted protein or polymer) will be determined by the molecular weight of the polyethylene glycol selected and on the number of available reactive groups (typically ε amino groups) present. In general, the higher the molecular weight of the polymer used, the fewer number of polymer molecules which can be attached to the protein. Similarly, branching of the polymer can be taken into account when optimizing these parameters. Generally, the higher the molecular weight (or the more branches) the higher the polymer:protein ratio. Several different linear PEG polymer lengths are contemplated, including but not limited to, 5 kDa and 20 kDa, conjugates of two-armed branched PEG polymers, including but not limited to 10 kDa and 40 kDa. In some embodiments, for the PEGylation reactions contemplated herein, the average molecular weight is about 2 kDa to about 100 kDa (the term "about" indicating +/−1 kDa). In other embodiments, the average molecular weight is about 5 kDa to about 40 kDa. The ratio of water-soluble polymer to PAL will generally range from 1:1 for monoPEG, 2:1 for diPEG, etc.

Pegylated Prokaryotic PAL Variants

Examples 7 through 9 of co-owned U.S. Pat. No. 7,531, 341, which is herein incorporated by reference in its entirety, describe the effects of pegylated and nonpegylated forms of lysine mutant R91K PAL from *Rhodosporidium toruloides* (RtPAL), NpPAL and AvPAL on Phe levels in the ENU2 or BTBR$^{enu2}$ mouse. This animal model is a homozygous mutant at the PAH locus resulting in an animal with severe hyperphenylalaninemia. The high plasma Phe levels make this animal the appropriate model for evaluating the ability of PAL to reduce plasma Phe. Administration of pegylated forms of NpPAL and AvPAL resulted in greater reduction in Phe in the ENU2 mice as compared to unpegylated NpPAL and AvPAL, respectively. Such effects were maintained for NpPAL upon weekly injections over a ten-week period. These results show that pegylation of PAL from the cyanobacteria, *Nostoc punctiforme* and *Anabaena variabilis*, is essential in reducing Phe levels in PKU affected mice.

Example 14 herein describes the effect of serine substitution of the cysteine residues (e.g., at positions 503 and 565) in the AvPAL polypeptide on Phe levels in ENU2 mice. The administration of the pegylated AvPAL double cysteine mutant AvPAL_C565SC503S results in a reduction in plasma Phe that is comparable to that achieved with pegylated wild-type AvPAL. In addition, the anti-PAL antibody titers are lower in animals injected with pegylated AvPAL variant as compared to pegylated wild-type AvPAL. These results show that a pegylated AvPAL variant has (1) in vivo PAL enzyme activity that is comparable to the pegylated wild-type AvPAL, and (2) has reduced immunogenicity compared to the pegylated wild-type AvPAL.

Pegylated PAL variants with reduced immunogenicity are provided herein. One embodiment is a pegylated form of NpPAL variant with reduced immunogenicity. Another embodiment is a pegylated form of AvPAL variant with reduced immunogenicity. Specific embodiments contemplate NpPAL or AvPAL variants in which pegylation is achieved by reacting the NpPAL or AvPAL variant with a water-soluble polymer, e.g., polyethylene glycol (PEG). In some embodiments, pegylation is achieved by reacting the NpPAL or AvPAL variant once with PEG at a ratio of at least 1:1, at least 1:1.5, at least 1:2, at least 1:3, or at least 1:4 PAL:PEG. In one embodiment, the PAL variant is an AvPAL variant, and the pegylation is achieved using a PAL:PEG ratio of 1:3. Methods for preparing the pegylated PAL variants are also provided herein.

In certain embodiments, one or more lysine residues are introduced at and/or near the active site of a prokaryotic PAL variant to enhance catalytic activity, reduce immunogenicity and/or improve biochemical stability, in part by blocking potential pegylation of other amino acid residues (e.g., tyrosine) at and/or near the active site of the enzyme or by blocking potential pegylation of a lysine residue important for enzyme activity. Without being bound to a particular theory, it is hypothesized that a tyrosine residue at and/or near the active site of a prokaryotic PAL (i.e., position 78 or 314 in AvPAL) can be a site for pegylation, which reduces enzyme activity. In some embodiments, one or more amino acid residues at and/or near the active site of the prokaryotic PAL, which are not required for enzyme activity, are substituted by a lysine residue. In a certain embodiment, the prokaryotic PAL is AvPAL. In one embodiment, the AvPAL tyrosine residue at position 78 or 314 is not accessible for pegylation. Again without being bound to a particular theory, it is hypothesized that a lysine residue of a prokaryotic PAL (i.e., position 419 in AvPAL), which is normally blocked from pegylation due to pegylation of a neighboring lysine residue PAL (i.e., position 413 in AvPAL), can be a site for pegylation, which reduces substrate binding and/or catalytic activity. In some embodiments, one or more amino acid residues of the prokaryotic PAL are substituted by a lysine residue, such that a lysine residue important for the enzyme's substrate binding and/or catalytic activity is not accessible for pegylation. In a specific embodiment, the prokaryotic PAL is AvPAL. In one embodiment, the AvPAL lysine residue at position 419 is not accessible for pegylation.

D. Therapeutic Uses and Administration of Prokaryotic Pal Variants

1. Various Forms of Hyperphenylalaninemia (HPA)

Provided herein are methods of treating a variety of HPA patient populations comprising the use of prokaryotic PAL variant compositions, either alone or in combination with other therapeutic regimens, for managing HPA and/or PKU. In particular, it is contemplated that prokaryotic PAL variant compositions can be used to treat that patient population with phenylalanine concentrations that are low enough that dietary intervention is not normally used (i.e., patients with mild HPA), patients with moderate PKU, patients with classic or severe PKU, and any subpopulations thereof. Such patients that are amenable to treatment with prokaryotic PAL variant compositions to ameliorate the effects of mild HPA include pregnant women and infants with serum concentrations of less than 200 The various patient populations, and their different therapeutic needs, are discussed in further detail in the present section.

Certain embodiments are directed to treating classic severe PKU by administering to the subject a protein-restricted diet in combination with a composition comprising prokaryotic PAL variant or a biologically active variant, mutant, or fragment thereof, wherein the combined administration of the protein-restricted diet and prokaryotic PAL variant is effective to lower the phenylalanine concentration in the plasma of said subject as compared to said concentration in the absence of said combined administration. In addition, provided are methods of treating a pregnant female that has HPA comprising administering to the female a protein-restricted diet in combination with prokaryotic PAL variant or a biologically active derivative thereof, such that the combined administration of the protein-restricted diet and prokaryotic PAL variant is effective to lower the phenylalanine concentration in the plasma of the pregnant woman as compared to such a concentration in the absence of said combined administration. In specific embodiments, therapy is contemplated for a patient who manifests Phe levels greater than 420 µM.

Other embodiments entail administering a prokaryotic PAL variant composition to any individual that has HPA, characterized by a plasma Phe concentration greater than 180 µM prior to the administration of prokaryotic PAL variant, in an amount effective to produce a decrease in such a plasma Phe concentration of the patient. The methods provided herein can also be useful in treating an infant having PKU characterized by an elevated Phe concentrations of between greater than 300 µM with prokaryotic PAL variant compositions described herein. By "infant," it is meant a patient that is between the ages of 0 to about 36 months.

Characteristics of Severe Classical PKU and Methods of Treatment Thereof

Severe PKU manifests in a plasma Phe concentration greater than 1200 µM and can be found to be as high as 4800 µM. Patients that have this disorder must be treated with a Phe-free diet in order to bring their plasma Phe concentrations down to a level that is clinically acceptable (typically, less than 600 µM or less than 300 µM). These patients are only able to tolerate a maximum of between 250-350 mg dietary Phe per day (Spaapen et al., Mol. Genet Metab. 78:93-99 (2003)). As such, these patients are started on a Phe-restricted formula diet between 7-10 days after birth and are burdened with this dietary restriction for the remainder their lifespan. Any alleviation of the strict dietary restrictions that these individuals are encumbered with would be beneficial.

The tests used for the diagnosis of individuals with classical Phe are described in further detail below. These tests have revealed that patients with classical severe PKU require a low phenylalanine diet (Lucke et al., Pediatr. Neurol. 28:228-230 (2003)). Thus, it is contemplated that certain methods provided herein will entail determining that the patient is suffering from classical PKU by monitoring the plasma Phe concentration of the individual. The patient can then be treated by administering prokaryotic PAL variant compositions alone or a combined regimen of a low protein diet and PAL variant such that there is produced at least a 25% decrease in the plasma Phe concentrations of the patient. In some embodiments, the method will produce a 30% decrease in the plasma Phe concentration. In other embodiments, the method will produce a 40%, 50%, 60%, 70%, 80%, 90% or greater decrease in the plasma Phe concentration of the individual (for example, where a patient with severe classical PKU has a Phe concentration of 4800 µM a 90% decrease in the Phe concentration will produce a plasma Phe concentration of 480 µM, a concentration that is sufficiently low to require little dietary restriction). Of course, it should be understood that the treatment methods provided herein, whether for treating severe classical PKU or any other HPA described herein, should attempt to lower the plasma Phe concentrations of the patient to levels as close to a range of about 120 µM to about 360 µM±15 µM as possible, or to an optimal range of about 120 µM to about 240 µM.

In some embodiments, the plasma Phe concentrations of the classical PKU patient being treated is reduced from any amount of unrestricted plasma Phe concentration that is greater than 1000 µM to any plasma Phe level that is less than 600 µM. Of course, even if the combined treatment with prokaryotic PAL variant and the protein-restricted diet produces a lesser decrease in plasma Phe concentration, e.g., to a level of between 800 µM to about 1200 µM, this will be viewed as a clinically useful outcome of the therapy because patients that have a plasma Phe concentration in this range can manage the disease by simply restricting the amount of protein in the diet as opposed to eating a Phe-restricted formula, thereby resulting in a marked improvement in the quality of life of the individual, as well as leading to greater patient compliance with the dietary restriction.

Any increase in the amount of dietary Phe levels that can be tolerated by the patient as a result of the treatment will be considered to be a therapeutically effective outcome. For example, it is contemplated that as a result of administering the prokaryotic PAL variant therapy, the patient will be able to increase his/her intake of dietary Phe from 250-350 mg/day to 350-400 mg/day (i.e., the Phe tolerance phenotype of the patient is altered from that of a classic PKU patient to a moderate PKU patient). Of course, it would be desirable that the therapeutic intervention taught herein would allow the patient to increase his/her intake of dietary Phe from 250-350 mg/day to 400-600 mg/day (i.e., the Phe tolerance phenotype of the patient is altered from that of a classic PKU patient to a mild PKU patient), or in some cases, to allow the patient to have an intake of greater than 600 mg Phe/day (i.e., normal dietary intake).

Characteristics of BH4-Non-Responsive PKU Patients and Methods of Treatment Thereof A second group of patients that can be treated with the compositions and methods provided herein are those individuals that have been determined to have an elevated plasma Phe concentrations i.e., any concentration that is greater than 200 µM, but have been diagnosed to be non-responsive to BH4 therapy (as determined by the BH4 loading test described below). Such patients can include those individuals that have mild PKU (i.e., plasma Phe concentrations of up to 600 µM), individuals that have moderate PKU (i.e., plasma Phe concentrations of between 600 µM to about 1200 µM), as well as patients that have classic severe PKU (i.e., plasma Phe concentrations that are greater than 1200 µM).

In some embodiments, patients that are non-responsive to BH4 therapy are given PAL variant in combination with a reduced amount of protein in their diet in order to decrease the plasma Phe concentrations of the patient. The administration of prokaryotic PAL variant can produce a greater decrease in the plasma Phe concentrations of the patient as compared to the decrease that is produced with the same dietary protocol administered in the absence of prokaryotic PAL variant therapy. The dietary restrictions can be a diet that restricts the Phe intake by providing a synthetic medical protein formula that has a diminished amount of Phe or alternatively, the dietary restriction can be one which simply requires that the patient limit his/her overall protein intake but nevertheless allows the patient to eat normal foodstuffs in limited quantities.

The therapeutic outcomes discussed for classical PKU patients are incorporated into the present section by reference. For example, the therapeutic outcomes for patients with moderate PKU (i.e., patients that has an unrestricted plasma Phe concentration of 600 µM to 1200 µM) can include at least a 25% decrease in the plasma Phe concentrations of the patient. In some embodiments, the method will produce a 30% decrease in the plasma Phe concentration. In other embodiments, the method will produce a 40%, 50%, 60%, 70%, 80%, 90% or greater decrease in the plasma Phe concentration of the individual (for example, where a patient with moderate classical PKU has a Phe concentration of 1000 µM, a 90% decrease in the Phe concentration will produce a plasma Phe concentration of 100 µM, a concentration that is sufficiently low to require little or no dietary restriction).

In some embodiments, the plasma Phe concentrations of the moderate PKU patient being treated is reduced from any amount of unrestricted plasma Phe concentration that is between 600 µM to 1200 µM to any plasma Phe level that is less than 300 µM. In one embodiment, treatment with prokaryotic PAL variant (either alone or in combination with a dietary restriction) produces a decrease in plasma Phe concentration, e.g., to a level of between 200 µM to about 400 which will be viewed as a clinically useful outcome of the therapy because patients that have a plasma Phe concentration in this range can manage the disease by simply restricting the amount of protein in the diet as opposed to eating a Phe-restricted formula. Indeed, in many studies, it is taught that such patients can even eat a normal diet.

Any increase in the amount of dietary Phe levels that can be tolerated by the patient as a result of the treatment will be considered to be a therapeutically effective outcome. For example, it is contemplated that as a result of administering the prokaryotic PAL variant therapy (either alone or in combination with other therapeutic intervention), the patient will be able to increase his/her intake of dietary Phe from 350-400 mg/day to 400-600 mg/day (i.e., the Phe tolerance phenotype of the patient is altered from that of a moderate PKU patient to a mild PKU patient). Of course, it would be desirable that the therapeutic intervention taught herein would allow the patient to increase his/her intake of dietary Phe from 350-400 mg/day to have an intake of greater than 600 mg Phe/day (i.e., normal dietary intake).

A patient manifesting only mild PKU, i.e., has a dietary allowance of 400-600 mg Phe intake/day, can be treated using the compositions and methods provided herein and can benefit from the prokaryotic PAL variant-based therapies because it is desirable to produce a normalized plasma Phe concentration that is as close to 360 µM±15 µM as possible. For such patients, an advantageous therapeutic outcome will include at least a 25% decrease in the plasma Phe concentrations of the patient. In one embodiment, the method will produce a 30% decrease in the plasma Phe concentration. In another embodiment, the method will produce a 40%, 50%, 60%, or greater decrease in the plasma Phe concentration of the individual (for example, where a patient with mild PKU has a Phe concentration of 600 µM, a 60% decrease in the Phe concentration will produce a plasma Phe concentration of 360 µM, i.e., an acceptable, normal concentration of plasma Phe).

In some embodiments, the plasma Phe concentrations of the mild PKU patient being treated is reduced from any amount of non-restricted plasma Phe concentration that is between 400 μM to 600 μM to any plasma Phe level that is less than 100 μM. Of course, even if the treatment with prokaryotic PAL variant (either alone or in combination with a dietary restriction) produces a lesser decrease in plasma Phe concentration, e.g., to a level of between 200 μM to about 400 μM, this will be viewed as a clinically useful outcome of the therapy.

Any increase the amount of dietary Phe levels that can be tolerated by the patient as a result of the treatment will be considered to be a therapeutically effective outcome. For example, it is contemplated that as a result of administering prokaryotic PAL variant therapy (either alone or in combination with other therapeutic intervention), the patient will be able to increase his/her intake of dietary Phe from 400-600 mg/day (i.e., the Phe tolerance phenotype of the patient is altered from that of a mild PKU patient to a mild HPA patient) to allow the patient to have an intake of greater than 600 mg Phe/day (i.e., normal dietary intake).

Furthermore, even if the patient is one who only manifests the symptoms of non PKU HPA, i.e., has an elevated plasma Phe concentration of up to 600 but is otherwise allowed to eat a normal protein diet will benefit from prokaryotic PAL variant therapy because it has been shown that elevated Phe concentrations have significant effects on the IQ of such individuals. Moreover, as discussed below, prokaryotic PAL variant therapeutic intervention of subjects with special needs, e.g., pregnant women and infants, is particularly important even if that patient's plasma Phe levels are within the perceived "safe" level of less than 200 μM.

Maternal PKU and Methods of Treatment Thereof

Metabolic control of plasma Phe levels in PKU women planning conception and those who are pregnant is important because of the serious consequences to the fetus exposed to even moderately elevated Phe levels in utero, regardless of the PAH status of the fetus. Therapeutic control of plasma Phe concentration is especially important in the first trimester of pregnancy, as failure to achieve adequate control will result in disorders including microcephaly, mental deficiency and congenital heart disease.

For example, the NIH Consensus Statement (vol 17 #3, October 2000) on phenylketonuria reported that exposure of a fetus to maternal Phe levels of 3-10 mg/dL produced a 24% incidence of microcephaly, whilst those exposed to greater than 20 mg/dL (i.e., greater than 1200 μM) had a 73% incidence of microcephaly. Likewise congenital heart disease was found in over 10% of children exposed to maternal Phe levels that were greater than 20 mg/dL. Importantly, it has been noted that levels of Phe greater than 6 mg/dL significantly decrease the IQ of the child. Thus, it is imperative to ensure that the plasma Phe concentration of women with all forms of phenylketonuria, even those manifesting the mildest HPA, must be tightly controlled in order to avoid the risk of maternal PKU syndrome. However, the acceptable target levels for the plasma Phe concentrations of PKU women that have been used in U.S. clinics have ranged between 10 mg/dL and 15 mg/dL, which are much higher than the 2-6 mg/dL levels recommended for pregnant women or the 1-4 mg/dL that are used in British and German clinics to diminish the risks of developing maternal PKU syndrome.

Another important consideration for pregnant women is their overall protein intake. During pregnancy, it is important that women eat sufficient protein because it has been suggested that a low protein diet during pregnancy will result in retarded renal development and subsequent reduction in the number of nephrons and potentially leads to hypertension in adulthood. (D'Agostino, N. Engl. J. Med. 348(17)1723-1724, (2003)). The following table provides exemplary guidelines for the recommended total dietary protein intake for various individuals.

| United States Guidelines for Dietary Protein Requirements | | |
|---|---|---|
| | Age | Recommended Total Protein Intake (g) |
| Infant | 6 months or less | 13 |
| | 6 months-1 year | 14 |
| | 1-3 years | 16 |
| Children | 4-6 years | 24 |
| | 7-10 years | 28 |
| Males | 11-14 years | 45 |
| | 15-18 years | 59 |
| | 19-24 | 58 |
| | 25-50 | 63 |
| | 51+ | 63 |
| Females | 11-14 years | 46 |
| | 15-18 years | 44 |
| | 19-24 | 46 |
| | 25-50 | 50 |
| | 51+ | 50 |
| Pregnant | | 60 |
| Lactating | | 65 |

As can be seen from the above exemplary guidelines, in the United States, the recommended protein intake for women of child-bearing age (e.g., less than 51) is from about 44 to 50 g/day, whereas pregnant women require are recommended an intake of about 60 g/day. In Canada and the United Kingdom, the recommended protein intake for pregnant women is in the order of about 70 g/day and 52 g/day. Thus, the need to ensure that the plasma Phe concentration levels of pregnant women are tightly controlled is further complicated by the fact that this group of PKU patient requires more protein than non-pregnant PKU females of comparable age.

In view of the above, it is contemplated that PAL variant therapies provided herein will be particularly useful in pregnant women. It is contemplated that a woman suffering from any form of HPA who is pregnant or is contemplating pregnancy can be placed on a course of prokaryotic PAL variant therapy to ensure that her plasma Phe concentration levels are maintained as close to 180 μM to about 360 μM as possible. Such a course of therapy would allow that woman to increase her level of normal protein intake.

The discussion of levels of plasma Phe concentrations and the degrees to which such Phe concentrations should be decreased discussed herein above are incorporated into the present section for pregnant women.

Managing PKU in Infants and Methods of Treatment Thereof

As discussed herein throughout, it has been determined that an elevation in the plasma Phe concentration in infants (ages zero to 3 years old) results in significant drop in IQ of the child. However, as has been discussed elsewhere in the specification, patients that have elevated plasma Phe concentrations of anywhere up to 400 μM do not normally receive any dietary intervention. Thus, infants at the age of zero to 3 years in age suffer from significant deleterious effects from the present therapies. The instant application contemplates treating any infant having an unrestricted plasma Phe concentration that is greater than 360 μM±15 μM with a therapeutic composition that comprises prokaryotic PAL variant in order to produce a beneficial decrease the plasma Phe concentration of that subject.

In some embodiments, the infant is aged between zero and 3 years of age and has an unrestricted plasma Phe concentration of about 1200 µM prior to the administration of prokaryotic PAL variant and said administration decreases the plasma Phe concentration. In one embodiment, the plasma Phe concentration is decreased to from greater than 1800 to about 1500 µM, about 1200 µM, about 1100 µM, about 1000 µM, about 900 µM, about 800 µM, about 700 µM, about 600 µM, about 550 µM, about 500 µM, about 450 µM, about 400 µM, about 350 µM, about 300 µM, about 275 µM, about 250 µM upon administration. In other embodiments, the infant is aged between zero and 3 years of age and has an unrestricted plasma Phe concentration of greater than 1200 µM and, this plasma Phe concentration is decreased to about 800 µM, to about 500 µM, or to about 360 µM, upon administration of prokaryotic PAL variant, either alone or in combination with diet. Those of skill in the art would understand that treating infants with unrestricted plasma Phe concentrations of greater than 360 µM with prokaryotic PAL variant to produce decreases in such plasma Phe concentrations is contemplated. The discussion of therapeutic reductions of plasma Phe concentrations above is incorporated herein by reference. Further, any decrease over 10% of the initial unrestricted plasma Phe concentration will be considered a therapeutic outcome for the therapeutic regimens for the infants. It should be understood that the prokaryotic PAL variant therapies can be combined with dietary restrictions to effect the therapeutic decrease in plasma Phe concentrations in such infants.

2. Other Therapeutic Uses

Various Forms of Cancer and Methods of Treatment Thereof

Also provided herein are methods of treating various forms of cancer comprising administering a therapeutically effective amount of a pharmaceutical composition comprising prokaryotic PAL variant to a subject. In a broad embodiment, the cancer is a cancer wherein the proliferation and/or survival of cells derived from the cancer is sensitive to phenylalanine restriction or depletion. In some embodiments, the cancer is lung cancer, brain or central nervous system cancer, colon cancer, prostate cancer, renal cancer, liver cancer, or metastatic melanoma. In other embodiments, the cancer is head and neck cancer, ovarian cancer, uterine cancer, leukemia (e.g., acute myeloid leukemia or acute lymphoblastoid leukemia) or myeloma. In yet other embodiments, the cancer is pediatric cancer or a resistant cancer (i.e., a cancer that has been shown to be resistant to cancer therapeutic agents or targeted cancer therapeutic agents).

In certain embodiments, provided is a method for treating cancer comprising administering to a subject in need of such treatment a therapeutically effective amount of a pharmaceutical composition comprising a prokaryotic PAL variant and a pharmaceutically acceptable carrier, wherein the prokaryotic PAL variant has a greater phenylalanine-converting activity and/or a reduced immunogenicity as compared to a wild-type PAL, and is effective in reducing the phenylalanine concentration in the blood, serum or plasma of the subject to a range from below the level of detection to between about 20 µM to 60 µM, such as less than about 20 µM, or less than about 10 µM, and optionally further comprising administering to the subject a protein-restricted (i.e., phenylalanine-free) diet.

Parkinson's Disease and Methods of Treatment Thereof

A detailed neuropathologic evaluation of the brains of Pah$^{enu2}$ mice, a model for PKU, revealed increased numbers of activated microglia or macrophages (CD11b$^+$ cells), as well as increased immunoreactivity of inducible nitric oxide synthase (iNOS) in two dopaminergic regions of the brain, the substantia nigra (SN) and hypothalamus (see Embury et al., Pediatr. Res. 58:283-287, 2005). This presence of infiltrating CD11+ cells and iNOS up-regulation in the SN is also observed in Parkinson's Disease (PD). Another common feature of PD and HPA/PKU is the reduction in dopamine in the brain, the latter occurring as the result of Phe not being converted to tyrosine (Tyr), which is a precursor of L-Dopa, which in turn is a precursor of dopamine. In addition, both PD and PKU are associated with loss of or damage to dopaminergic neurons, and both PD and at least Pah$^{enu2}$ mice clinically display a disturbance in motor function.

Provided herein are methods of treating PD comprising administering a therapeutically effective amount of a pharmaceutical composition comprising prokaryotic PAL variant to a subject. Prokaryotic PAL variant therapy can be in combination with other therapies to treat PD, including, e.g., neurotransmitters like the dopamine precursor, L-Dopa, which is known to be able to cross the blood-brain barrier.

Disease indications wherein administration of therapeutically effective amounts of prokaryotic PAL variant would be beneficial include, but are not limited to, HPA, PKU, tyrosinemia, cancer and PD. Parenteral, oral, or other standard routes of administration and dosage can be determined using standard methods.

2. Compositions for Use in the Treatment

Also provided herein are therapeutic interventions of PKU/HPA. Such intervention is based initially on the use of prokaryotic PAL variant, which can be used alone or in combination with dietary restrictions. Further prokaryotic PAL variant and/or dietary restrictions can further be combined with other therapeutic compositions that are designed, for example, to combat other manifestations of PKU, such as for example, large neutral amino acids to prevent Phe accumulation in the brain (see Koch, et al., Mol. Genet. Metabol. 79:110-113 (2003)) or tyrosine supplementation. The present section provides a discussion of the compositions that can be used in the treatments contemplated herein.

Prokaryotic PAL Variant Compositions, Pharmaceutical Compositions and Formulations Pharmaceutical compositions are provided herein, comprising therapeutically effective amounts of a prokaryotic PAL variant together with one or more pharmaceutically acceptable excipients, vehicles diluents, stabilizers, preservatives, solubilizers, emulsifiers, adjuvants and/or carriers. Such pharmaceutical compositions include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., Remington's Pharmaceutical Sciences, 18$^{th}$ Edition (1990, Mack Publishing Co., Easton, Pa.) pages 1435:1712, which are herein incorporated by reference. An effective amount of active ingredient is a therapeutically, prophylactically, or diagnostically effective amount, which can be readily determined by a person skilled in the art by taking into consideration such factors as body weight, age, and therapeutic goal.

In some embodiments, the prokaryotic PAL variant pharmaceutical composition includes a buffering agent to maintain the pH of the solution within a desired range. Such buffering agents include Tris-HCl, sodium acetate, sodium phosphate, and sodium citrate. Mixtures of these buffering agents can also be used. The amount of buffering agent useful in the composition depends largely on the particular buffer used and the pH of the solution. For example, acetate is a more efficient buffer at pH 5 than pH 6 so less acetate can be used in a solution at pH 5 than at pH 6. In some embodiments, the buffering agent is Tris-HCl. In certain embodiments, the pH range for the pharmaceutical compositions is about pH 6.0-8.0, such as about pH 6.5-7.5 or about pH 7.0-7.6.

The pharmaceutical compositions provided herein can further include an isotonicity-adjusting agent to render the solution isotonic and more compatible for injection. In some embodiments, the isotonicity-adjusting agent is sodium chloride within a concentration range of 100-200 mM, such as 120-170 mM or 120-150 mM.

Pharmaceutically acceptable carriers or excipients can include stabilizers, which are molecules that stabilize the prokaryotic PAL variant composition provided herein. The term "stabilize" as used herein, is meant to include, for example and not for limitation, increasing the shelf-life of a prokaryotic PAL enzyme, protecting the prokaryotic PAL enzyme from proteolytic digestion, maintaining the prokaryotic PAL enzyme in an active conformation, and/or preserving the prokaryotic PAL enzyme activity upon storage at elevated temperatures. For example, a stabilizer can increase by at least about 10%, 20%, 30%, 40%, 50%, 60%, 70%, 80%, 90%, 100%, 150%, 200%, 300%, 400%, 500%, 600%, 700%, 800%, 900%, 1000% or more (e.g., about 1.5-fold, 2-fold, 3-fold, 4-fold, 5-fold, 6-fold, 7-fold, 8-fold, 9-fold or 10-fold, or within any range thereof) the shelf-life ($T_{90}$) of a pegylated prokaryotic PAL variant (e.g., as compared to a pegylated prokaryotic PAL variant without the presence of stabilizer), i.e., the time in which the specific in vitro enzyme activity, determined using the assay described in Example 3, has dropped by ≥10% at a given temperature, e.g., 4° C., 25° C., 37° C., 40° C. or 42° C. In certain embodiments, the $T_{90}$ is between 6-fold to 7-fold greater at 4° C.; between 4-fold to 5-fold greater at 25° C., between 2-fold to 3-fold greater at 37° C., between 2-fold to 3-fold greater at 42° C., or a combination thereof. In some embodiments, the pegylated prokaryotic PAL variant is a pegylated double-cysteine mutant AvPAL_C565SC503S and the stabilizer is Phe. Alternatively, a stabilizer can preserve the enzyme activity of a pegylated prokaryotic PAL variant upon storage at elevated temperatures, i.e., the variant retains at least about 40%, 50%, 60%, 70%, 80%, 85%, 90%, 95%, 99% or more, or within any range thereof, of its specific in vitro enzyme activity, determined using the assay as described in Example 3, upon storage at 25° C., 37° C. or 40° C. for a given period of time, e.g., 1 week, 2 weeks, 3 weeks, 4 weeks, 5 weeks, 6 weeks, 7 weeks, 8 weeks, 9 weeks, 10 weeks, 11 weeks, 3 months, 4 months, 6 months, 9 months, 1 year, 2 years, 5 years or more, or any range thereof (e.g., as compared to a pegylated prokaryotic PAL variant without the presence of stabilizer).

Stabilizers include L-phenylalanine (Phe) and structural analogs thereof, such as trans-cinnamic acid (t-CA), benzoic acid, tyrosine (Tyr), and the like. Loss of activity of a plant PAL from *Phaseolus vulgaris* (PvPAL) has been shown upon removal of its substrate L-phenylalanine after affinity purification (Da Cunha, Eur. J. Biochem. 178:243-248 (1988)), and a yeast PAL from *Rhodosporidium toruloides* (RtPAL) has been shown to be protected from protease inactivation by tyrosine (Wang, et al., Mol. Genet. Metab. 86:134-140 (2005); Pilbak, et al., FEBS J. 273:1004-1019 (2006)). As shown herein below, Phe and certain of its structural analogs have the ability to stabilize PEG:PAL conjugates of a prokaryotic PAL from AvPAL (see EXAMPLE 11). Without being bound to a particular theory, it is hypothesized that the prokaryotic PAL enzyme is more stable as an enzyme-substrate complex, wherein the bound substrate Phe is converted to the product t-CA or to a transition state analog of t-CA. The t-CA remains bound to the otherwise highly reactive active site center (MIO group), thereby stabilizing the prokaryotic PAL enzyme. Accordingly, the prokaryotic PAL enzyme substrate, Phe, product, t-CA, or structural analogs thereof can be used as stabilizers.

Also provided are pharmaceutical compositions comprising a prokaryotic PAL variant and a pharmaceutically acceptable carrier, wherein the pharmaceutically acceptable carrier comprises a stabilizer. The stabilizer can be Phe or structural analog thereof. The stabilizer can be selected from the group consisting of L-phenylalanine, trans-cinnamic acid and benzoic acid. An exemplary range for the stabilizers is from about 0.1 to 20 moles of stabilizer per mole active site of prokaryotic PAL, such as from about 0.5 to 10 moles of stabilizer per mole active site of prokaryotic PAL, or from about 1 to 10 moles of stabilizer per mole active site of prokaryotic PAL.

In some embodiments, the pharmaceutical composition comprises a prokaryotic PAL variant and a pharmaceutically acceptable carrier, wherein the prokaryotic PAL variant has a greater phenylalanine-converting activity and/or a reduced immunogenicity as compared to a wild-type PAL, and wherein the pharmaceutically acceptable carrier comprises a stabilizer. In some embodiments, the stabilizer is Phe or structural analog thereof. In some embodiments, the stabilizer is selected from the group consisting of L-phenylalanine, trans-cinnamic acid and benzoic acid.

In certain embodiments, the pharmaceutical composition comprises a prokaryotic PAL variant and a pharmaceutically acceptable carrier, wherein the prokaryotic PAL variant is an AvPAL variant, wherein the cysteine residues at positions 503 and 565 of the AvPAL variant have been substituted by serine residues, the AvPAL variant further comprises a water-soluble polymer of polyethylene glycol, wherein the ratio of AvPAL variant and the polyethylene glycol is about 1:3, and wherein the pharmaceutically acceptable carrier comprises a stabilizer. In some embodiments, the stabilizer is Phe or structural analog thereof. In some embodiments, the stabilizer is selected from the group consisting of L-phenylalanine, trans-cinnamic acid and benzoic acid.

Pharmaceutically acceptable carriers or excipients can include preservatives, e.g., anti-microbial agents, which are substances that terminate or prevent the growth of microorganisms such as bacteria, fungi, or protozoans, as well as destroy viruses. Anti-microbial agents can either kill microbes (microbicidal) or prevent their growth (microbistatic). Preservatives are useful, for example and not for limitation, protecting the prokaryotic PAL enzyme from microbial contamination, increasing the shelf-life of a prokaryotic PAL enzyme, maintaining the prokaryotic PAL enzyme in an active conformation, and preserving the prokaryotic PAL enzyme activity upon storage at elevated temperatures.

Preservatives provided herein can include phenol and structural analogs thereof, such as m-cresol, and the like. An exemplary range of concentrations for the preservatives, e.g., m-cresol, is from about 0.1% to 1% (w/v). IN certain embodiments, the range for m-cresol is from about 0.1% to 0.5% (w/v). In other embodiments, the range for m-cresol is from about 0.3% to 0.5% (w/v).

Stabilizers provided herein, when used alone or in combination with a preservative, include Phe and structural analogs thereof and Gly and structural analogs thereof. An exemplary range of the concentrations for stabilizers, e.g., Phe, is from about 0.1 to 10 mM. In some embodiments, the range for Phe is from about 0.5 to 5 mM. In other embodiments, the range for Phe is from about 0.5 to 1.5 mM. An exemplary range of the concentrations for stabilizers, e.g., Gly, is from about 0.1 to 100 mM. In some embodiments, the range for Gly is from about 1 to 100 mM. In other embodiments, the range for Gly is from about 1 to 20 mM. In other embodiments, the range for Gly is from about 20 to 100 mM.

In some embodiments, the pharmaceutical composition comprises a prokaryotic PAL variant and a pharmaceutically acceptable carrier, wherein the prokaryotic PAL variant has a greater phenylalanine-converting activity and/or a reduced immunogenicity as compared to a wild-type PAL, and wherein the pharmaceutically acceptable carrier comprises at least two stabilizers and, optionally, a preservative (i.e., anti-microbial agent). In some embodiments, the at least two stabilizers are Phe or structural analog thereof and Gly or structural analog thereof, or any combination thereof. In some embodiments, the stabilizers are Phe and Gly. In some embodiments, the preservative is m-cresol or structural analog thereof. In specific embodiments, the stabilizers are Phe and Gly and the preservative is m-cresol.

In certain embodiments, the pharmaceutical composition or formulation comprises a pegylated AvPAL variant and a pharmaceutically acceptable carrier, wherein the ratio of the AvPAL variant and polyethylene glycol is about 1:3 (1:3 AvPAL:PEG), and the cysteine residues at positions 503 and 565 of the AvPAL variant have been substituted by serine residues, and wherein the pharmaceutically acceptable carrier comprises at least two stabilizers and, optionally, a preservative (i.e., anti-microbial agent). In some embodiments, the at least two stabilizers are Phe or structural analog thereof and Gly or structural analog thereof, or any combination thereof. In some embodiments, the stabilizers are Phe and Gly. In some embodiments, the preservative is m-cresol or structural analog thereof. In specific embodiments, the stabilizers are Phe and Gly and the preservative is m-cresol.

As used herein, and when contemplating prokaryotic PAL variants, the term "therapeutically effective amount" refers to an amount, which gives a decrease in blood, plasma or serum L-phenylalanine that provides benefit to a patient. The amount will vary from one individual to another and will depend upon a number of factors, including the overall physical condition of the patient, diet and disease state. The amount of prokaryotic PAL variant used for therapy gives an acceptable decrease in blood, plasma or serum L-phenylalanine levels, and maintains this value during prokaryotic PAL variant treatment at a beneficial level (usually at least about 30% and typically in a range of 10% to 50%). A therapeutically effective amount of the present compositions can be readily ascertained by one skilled in the art using publicly available materials and procedures.

In certain embodiments, prokaryotic PAL variants, or pharmaceutical compositions thereof, are administered less frequently than native PAL. The dosing frequency will vary depending upon the condition being treated, but in general will be about one time per week. It is understood that the dosing frequencies actually used may vary somewhat from the frequencies disclosed herein due to variations in responses by different individuals to the prokaryotic PAL variants; the term "about" is intended to reflect such variations. It is contemplated that the prokaryotic PAL variants are administered about two times per week, about one time per week, about one time every two weeks, about one time per month, or longer than about one time per month.

The compositions and methods provided herein can be used to reduce blood, plasma or serum L-phenylalanine levels. As discussed above, most commonly, serum L-phenylalanine levels are increased due to HPA. Among the conditions treatable by the compositions and methods provided herein include HPA associated with PKU. Also treatable are conditions that can lead to increased serum L-tyrosine levels such as found in tyrosinemia. Numerous cancer-related conditions, where depletion of blood, plasma or serum L-phenylalanine levels would be beneficial, can be treated with the prokaryotic PAL variant pharmaceutical compositions and methods provided herein.

The prokaryotic PAL variant pharmaceutical compositions provided herein are, in certain embodiments, administered by parenteral injection, either intravenously, intraperitoneally, subcutaneously, intramuscularly, intraarterially or intrathecally. However, it would be clear to one skilled in the art that other routes of delivery could also be effectively utilized.

The methods described herein use prokaryotic PAL variant pharmaceutical compositions comprising the molecules described above, together with one or more pharmaceutically acceptable excipients, vehicles, diluents, stabilizers, preservatives (e.g., anti-microbial agents), solubilizers, emulsifiers, adjuvants and/or carriers, and optionally other therapeutic and/or prophylactic ingredients. Such excipients include liquids such as water, saline, glycerol, polyethylene glycol, hyaluronic acid, ethanol, cyclodextrins, modified cyclodextrins (i.e., sufobutyl ether cyclodextrins), etc. Suitable excipients for non-liquid formulations are also known to those of skill in the art.

Pharmaceutically acceptable salts can be used in the compositions include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in Remington's Pharmaceutical Sciences, 18$^{th}$ Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, such as in unit dosage form suitable for single administration of a precise dosage. The compositions can include a therapeutically effective amount of the prokaryotic PAL variant in combination with a pharmaceutically acceptable carrier and, in addition, can optionally include other pharmaceutical agents, adjuvants, diluents, buffers, etc.

In general, the prokaryotic PAL variant pharmaceutical compositions provided herein will be administered as pharmaceutical formulations, including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. In certain embodiments, the compositions are administered, e.g., intravenously, using a convenient daily dosage regimen, which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., a prokaryotic PAL variant composition as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, or softgel capsule, or can be an aqueous or nonaqueous solution, suspension or syrup. Tablets and capsules can be used as oral administration forms. Tablets and capsules for oral use will generally include one or more commonly used carriers such as lactose and corn starch. Lubricating agents, such as magnesium stearate, are also typically added. When liquid suspensions are used, the active agent can be combined with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid or lyophilized forms suitable for reconstitution, solubilization or suspension in liquid prior to injection, or as emulsions. In certain embodiments, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

The prokaryotic PAL variant compositions described herein can be administered to a patient at therapeutically effective doses to treat a variety of diseases, including hyperphenylalaninemia, including phenylketonuria, and other disorders, including cancer. The toxicity and therapeutic efficacy of such prokaryotic PAL variant compositions can be determined by standard pharmaceutical procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prokaryotic PAL variant compositions exhibiting large therapeutic indices can be used.

The data obtained from the cell culture assays and animal studies can be used in formulating a range of dosage for use in humans. The dosage can lie within a range of circulating concentrations that include the $ED_{50}$ with little or minimal toxicity. The dosage can vary within this range depending upon the dosage form employed and the route of administration utilized. The therapeutically effective dose or amount can be determined from cell culture assays, and from animal models.

Dietary Protein

In addition to administering prokaryotic PAL variant compositions to HPA/PKU patients, it is contemplated that, in certain embodiments, the dietary protein of the patients also can be restricted or modified. Those of skill in the art are aware of various commercially available protein formulas for use in the treatment of PKU. Such formulas include MAXIMAID, PHENEX 1, PHENEX 2 (Ross Laboratories, Liverpool, UK), LOFENALAC, PHENYL-FREE (Mead-Johnson), and the like.

Those of skill in the art can use the referenced protein formulas, which are generally free of Phe concentrations. The protein formulas often are supplemented with amino acids that are deficient in PKU patients. Such amino acids include, for example, L-tyrosine, and L-glutamine. It has been suggested that it may be desirable to supplement the diet of PKU patients with valine, isoleucine and leucine (see U.S. Pat. No. 4,252,822). In certain clinical manifestations, the toxic effects of PKU are caused by Phe blocking the brain uptake of other amino acids such as tyrosine and tryptophan. It has been found that supplementing the diet of a PKU patient with excess of such large neutral amino acids blocks Phe uptake into the brain and lowers brain Phe levels. Thus, it is contemplated that for the methods provided herein, the dietary regimen can further be supplemented with compositions that comprise one or more of these amino acids (Koch, et al., Mol. Genet. Metabol. 79:110-113 (2003)).

Further, as it is known that L-carnitine and taurine, which are normally found in human milk and other foodstuffs of animal origin, also should be supplied in addition to the protein restriction. In certain embodiments, the L-carnitine can be supplied as 20 mg/100 g of protein supplement, and the taurine can be supplied as 40 mg/100 g protein supplement in order to help supply amounts of these factors normally found in human milk and foods of animal origin.

In addition, those of skill in the art are referred to the 2000 National Academy of Sciences-National Research Council Dietary Reference Intakes for a further listing of other components, such as essential vitamins and minerals that should be supplied to the patient to ensure that other supplements are being provided despite the dietary protein restriction.

Referring to the discussion above regarding total protein amounts and desirable plasma Phe concentrations, one of skill in the art will be able to determine the amount of dietary protein restriction that is required and thus adjust the diet of the patient accordingly. Taking for example, a male of about 11-14 years of age, that individual should receive 45 g protein/day. In the event that the individual is one that has severe classic PKU, his unrestricted plasma Phe concentration will likely be greater than 1200 µM, and most, if not all of the dietary protein source for that individual is likely to be from a powdered protein supplement, which can lower his plasma Phe concentrations to less than 600 By administering prokaryotic PAL variant to that subject, a therapeutic outcome would be one which produces greater decrease in the plasma Phe concentrations of patient or alternatively, the therapeutic outcome is one in which the individual's plasma Phe concentrations is lowered to a similar degree, but that individual is able to tolerate protein from a normal diet rather than from a dietary formula.

Similarly, for a male of about 11-14 years of age who has moderate PKU, it may be possible using the methods provided herein to give him the allotted 45 g protein/day through a normal protein intake rather than a restricted formula. Determining whether the methods provided herein are effective will entail determining the plasma Phe concentrations of the patient on a regular basis to ensure that the plasma Phe concentrations remain below at least 400 Tests for determining such concentrations are described below. In some embodiments, concentrations of less than or about 360 µM are achieved.

3. Identifying and Monitoring Patient Populations

As discussed herein, it can be necessary to determine whether a given patient is responsive to prokaryotic PAL variant therapy, and to determine the phenylalanine concentrations of the patient both initially to identify the class of PKU patient being treated and during an ongoing therapeutic regimen to monitor the efficacy of the regimen. Such exemplary methods are described below.

BH4 Loading Test

The BH4 loading test allows discrimination between patients that have HPA due to a deficit in BH4 or through a deficiency in PAH.

The simplest BH4 loading test is one in which exogenous BH4 is administered and the effects of the administration on lowering of plasma Phe concentrations is determined. Intravenous loading of 2 mg/kg BH4 was initially proposed by Danks, et al., Lancet 1:1236 (1976), as BH4 of greater purity has become available it has become possible to perform the test using an oral administration of BH4 in amounts of about 2.5 mg/kg body weight. Ultimately, a standardized approach was proposed by Niederwieser et al. in which a 7.5 mg/kg single oral dose of BH4 is administered (Niederwieser, et al., Eur. J. Pediatr. 138:441 (1982)), although some laboratories do still use upwards of 20 mg BH4/kg body weight.

In order for the simple BH4 loading test to produce reliable results, the blood Phe levels of the patient need to be higher than 400 µM. Therefore, it is often customary for the patient to be removed from the PKU diet for 2 days prior to performing the loading test. A BH4 test kit is available and distributed by Dr. Schircks Laboratories (Jona, Switzerland). This kit recommends a dosage of 20 mg BH4/kg body weight about 30 minutes after intake of a normal meal.

Determination of Phe Concentrations

There are numerous methods for determining the presence of Phe in blood (see, e.g., Shaw et al., Analytical Methods in Phenylketonuria-Clinical Biochemistry, In Bickett et al. Eds., Phenylketonuria and Some Other Inborn Errors of Amino Acid Metabolism, Stuttgart, Georg Thiem Verlag, 47-56 (1971)). Typically, phenylalanine and tyrosine concentrations are determined from the serum of a patient using a fluorometric assay. This assay relies on the formation of fluorescent substance when phenylalanine is heated with ninhydrin in the presence of leucylalanine (McCaman, et al., J. Lab. Clin. Med. 59:885-890 (1962)).

The most popular method for determining Phe concentrations is the Guthrie test in which discs are punctured from filter paper that has been saturated with a blood sample from the patient. The uniform discs are incubated in a tray of agar that has been seeded with *Bacillus subtilis* and contains a specific inhibitor of *Bacillus subtilis* growth. As the phenylalanine transfers from the uniform discs onto the agar, the Phe reverse the inhibition of bacterial growth thereby yielding an area of bacterial growth that can be correlated to phenylalanine concentration by comparison to similar assays performed using discs containing known amounts of Phe.

Other methods of quantifying Phe concentration include HPLC, mass spectrometry, thin layer chromatography and the like. Such methods can be used to determine the plasma Phe concentration of a patient before the therapy and to monitor the Phe concentration during the therapeutic regimen to determine the efficacy thereof.

It is contemplated that the plasma Phe levels of the patients will be monitored at convenient intervals (e.g., daily, every other day or weekly) throughout the time course of the therapeutic regimen. By monitoring the plasma Phe levels with such regularity, the clinician will be able to assess the efficacy of the treatment and adjust the prokaryotic PAL variant and/or dietary protein requirements accordingly.

4. Combination Therapy

In certain embodiments of the methods provided herein, prokaryotic PAL variant and dietary protein restriction are used in combination to effect a therapeutic outcome in patients with various forms of HPA. To achieve the appropriate therapeutic outcome in the combination therapies contemplated herein, one would generally administer to the subject the prokaryotic PAL variant composition and the dietary restriction in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process can involve administering the prokaryotic PAL variant composition and the dietary protein therapeutic composition at the same time. This can be achieved by administering a single composition or pharmacological protein formulation that includes all of the dietary protein requirements and also includes the prokaryotic PAL variant within said protein formulation. Alternatively, the dietary protein (supplement or normal protein meal) is taken at about the same time as a pharmacological formulation (tablet, injection or drink) of prokaryotic PAL variant. Prokaryotic PAL variant also can be formulated into a protein bar or other foodstuff such as brownies, pancakes, cake, suitable for ingestion.

In other alternatives, prokaryotic PAL variant treatment can precede or follow the dietary protein therapy by intervals ranging from minutes to hours. In embodiments where the protein and the prokaryotic PAL variant compositions are administered separately, one would generally ensure that a significant period of time did not expire between the time of each delivery, such that prokaryotic PAL variant will still be able to exert an advantageously effect on the patient. In such instances, it is contemplated that one would administer the prokaryotic PAL variant within about 2-6 hours (before or after) of the dietary protein intake, with a delay time of only about 1 hour in some embodiments. In certain embodiments, it is contemplated that prokaryotic PAL variant therapy will be a continuous therapy where a daily dose of prokaryotic PAL variant is administered to the patient indefinitely. In other situations, e.g., in pregnant women having only the milder forms of PKU and HPA, it may be that prokaryotic PAL variant therapy is only continued for as long as the woman is pregnant and/or breast feeding.

Further, in addition to therapies based solely on the delivery of prokaryotic PAL variant and dietary protein regulation, the methods provided herein also contemplate combination therapy with a third composition that specifically targets one or more of the symptoms of HPA. For example, it is known that the deficit in tyrosine caused by HPA results in a deficiency in neurotransmitters dopamine and serotonin. Thus, it is contemplated that prokaryotic PAL variant and dietary protein based methods could be further combined with administration of L-dopa, carbidopa and 5-hydroxytryptophan neurotransmitters to correct the defects that result from decreased amounts of tyrosine in the diet.

As the administration of prokaryotic PAL variant would not generate tyrosine (unlike administration of PAH), such treatment will still result in tyrosine being an essential amino acid for such patients. Therefore dietary supplementation with tyrosine can be desirable for patients receiving prokaryotic PAL variant in combination with the BH4 therapy.

E. Production of Prokaryotic PAL Variants

Also provided herein is a method of producing prokaryotic PAL or biologically active fragment, mutant variant or analog thereof. In one exemplary embodiment, recombinant prokaryotic PAL or a biologically active fragment, mutant, variant or analog thereof is over-expressed, with or without an N-terminal tag (e.g., octahistidyl-tag), in a vector, such as pIBX1 (Su, et al., Appl. Environ. Microbiol. 62:2723-2734 (1996)) or pET28a (Invitrogen) with an inducible promoter such as with IPTG (isopropyl-beta-D-thiogalactopyranoside), in $E.$ $coli$ BLR(DE3)/pLysS (Novagen) or $E.$ $coli$ BL21(DE3)/pLysS (Invitrogen) cells. Seed culture for a bioreactor/fermenter is grown from a glycerol stock in shake flasks. Such seed culture is then used to spike into a controlled bioreactor in fed-batch mode. Glucose is supplemented and pH is controlled with base (NH4OH) and agitation is up to 1200 rpm. $O_2$ feed keeps dissolved oxygen to greater than 20%. The cells are grown at a temperature of 37° C. until reaching an $OD_{600}$ of 70-100 (~22-25 hrs) and then induced with 0.4 mM IPTG. The temperature is reduced to 30° C. and grown until activity change is <0.1 IU/mL (approximately 40-48 hrs and an $OD_{600}$ typically of 200). Cell culture media is typically defined and composed of yeast extract protein, peptone-tryptone, glucose, glycerol, casamino acids, trace salts and phosphate buffering salts. The recombinant prokaryotic PAL product or biologically active fragment, mutant, variant or analog thereof is produced intra-cellularly and not secreted. The bacteria are harvested by continuous centrifugation (Alfa-Laval, Carr, Cepa, or equivalent). Other variations of this exemplary protocol will be apparent to one skilled in the art.

F. Purification of Prokaryotic PAL Variants

Also provided herein is a method to purify prokaryotic PAL or a biologically active fragment, mutant, variant or analog thereof. According to an exemplary first embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another embodiment, the method to purify the prokaryotic PAL or biologically active fragment, mutant, variant or analog thereof comprises: (a) lysis of the bacteria containing recombinant prokaryotic PAL or biologically active fragment, mutant, or analog thereof using a pressure homogenizer (but potentially by other physical means such as glass bead lysis); (b) heat treatment; (c) clarification of this lysate using a second continuous centrifugation step and/or depth filtration (as with Cuono Zeta Plus or Maximizer, Pall Filtron, or Millipore Millistak or Opticao filters); (d) passage through a charcoal filtration step (as with Millipore Millistak 40AC); (e) passage through an intermediate depth filtration step (as with one or more depth filters, e.g., Pall EKSP, Pall KS50P and/or Pall EKMP filters) followed by a final filtration step (as with a Sartorious Sartopore or Pall EDF 0.2 µm filter); (f) passage over a butyl hydrophobic interaction chromatography (as in Toyopearl Butyl 650M from Tosoh Biosciences); (g) passage over a Q ion exchange column (as in a Macroprep High Q from BioRad); and (h) recovery of final product, optionally by buffer exchange with tangential flow filtration (as with a Sartorious Hydrosart or PES 30 kDa membrane). Those skilled in the art readily appreciate that one or more of the chromatography steps or filtration steps can be omitted or substituted, or that the order of the chromatography steps or filtration steps can be changed. Finally, appropriate sterilizing steps can be performed as desired.

Having now generally described the invention, the same can be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example 1

Cloning of *Nostoc punctiforme* and *Anabaena variabilis* PAL DNA Manipulations

*N. punctiforme* genomic DNA was purchased from ATCC (29133D) and the PAL gene (ZP_00105927) was PCR-amplified from primers 5'-CACTGTCATAT-GAATATAACATCTCTACAACAGAACAT-3' (SEQ ID NO:12) and 5'-GACAGTGGCGGCCGCTCACGTT-GACTTTAAGCTCGAAAAAATATG-3' (SEQ ID NO:13). The resulting PCR product was digested with NdeI and NotI and the 1.7 kb fragment was ligated into pET-28a(+) and pET-30a(+) (Novagen) for N-His tagged and untagged, respectively.

*A. variabilis* cells were purchased from ATCC (29413). Genomic DNA was extracted (Qiagen) and the PAL gene (YP_324488) was amplified by SOE-PCR to remove an NheI site. Primer 1 (5'-CACTGTGCTAGCATGAAGA-CACTATCTCAAGCACAAAG-3') (SEQ ID NO:14) and primer 2 (5'-GGAAATTTCCTCCATGATAGCTGGCTTG-GTTATCAACATCAATTAGTGG-3') (SEQ ID NO:15) were used to amplify nucleotides 1-1190 and primer 3 (5'-CCACTAATTGATGTTGATAACCAAGCCAGCTAT-CATGGAGGAAATTTCC-3') (SEQ ID NO:16) and primer 4 (5'-CACTGTGCGGCCGCTTAATGCAAGCAGGG-TAAGATATCTTG-3') (SEQ ID NO:17) were used to amplify nucleotides 1142-1771. These two PCR products were combined to amplify the full-length gene with primers 1 and 4. The resulting PCR product was digested with NheI, blunted with Klenow (NEB), then digested with NotI. The 1.7 kb fragment was ligated into pET-28a(+) and pET-30a(+) (Novagen). This plasmid was named 3p86-23.

The AvPAL gene was also cloned into the vector pIBX7 (Tkalec, et al., Appl. Environ. Microbiol. 66:29-35 (2000)), which was derived from pIBX1 (Su, et al., Appl. Environ. Microbiol. 62:2723-2734 (1996)) (see EXAMPLE 7).

Bacterial Strains and Culture Conditions

For *N. punctiforme* PAL (NpPAL), *E. coli* BL21(DE3) cells (Stratagene) were transformed with pGro7 (TaKaRa) and competent BL21(DE3)pGro7 cells were prepared by the Inoue Method (Sambrook and Russell, Molecular Cloning: A Laboratory Manual, 3$^{rd}$ Edition (Cold Spring Harbor Laboratory Press, Cold Spring Harbor, 2001)). These cells were transformed with pET-28-NpPAL and cultured in 25 mL LB with 50 mg/L kanamycin and 20 mg/L chloramphenicol overnight at 37° C. Twenty milliliters of this culture was seeded into 1 L of LB medium with kanamycin, chloramphenicol, and 500 mg/L L-arabinose and grown at 37° C. At an $OD_{600}$ of 0.6, the culture was chilled on ice. After 5 minutes, the culture was induced with 0.3 mM IPTG and grown for 16 hours at 20° C. Cells were harvested by centrifugation.

BL21(DE3)pLysS cells (Stratagene) were transformed with AvPAL and cultured identically to NpPAL without the arabinose induction.

AvPAL cloned in the pIBX7 vector (see EXAMPLE 7) was introduced by transformation into BLR(DE3)/pLysS (Novagen) cells and cultured in 25 mL LB with 50 mg/L kanamycin overnight at 37° C. Twenty milliliters of this culture was seeded into 1 L of LB medium with kanamycin, and grown at 37° C. At an $OD_{600}$ of 0.6, the culture was chilled on ice. After 5 minutes, the culture was induced with 0.3 mM IPTG and grown for 16 hours at 30° C. Cells were harvested by centrifugation.

Example 2

Purification of NpPAL and AvPAL

The cultures were centrifuged in a bench-top centrifuge at 5,000 g for 20 minutes and the supernatant discarded. The cell pellets were typically frozen at −70° C. prior to further processing. Upon thawing, the cell pellets were suspended to approximately 80 optical density units (600 nm) in TBS (25 mM Tris, 150 mM NaCl, pH 7.8). The cells were lysed by two passes through an APV pressure homogenizer at 12-14,000 psi. The crude lysate was then heat-treated at 55° C. for 2 hours. The lysate is centrifuged at 10,000 g for 30 minutes and the supernatant retained and filtered with a 0.2 µm vacuum filter (Corning).

The PAL was purified from the clarified lysate by passage sequentially over a butyl 650M column (Tosoh BioSciences) and a MacroPrep High Q column (BioRad). The eluted product showed a high level of purity by both SDS PAGE and reverse phase HPLC.

Example 3

Generation of Pegylated PAL Variants

A method for pegylation of PAL from *Rhodosporidium toruloides* (RtPAL) is described below. Similar methods are used for pegylation of prokaryotic PAL (e.g., NpPAL or AvPAL) are described in EXAMPLE 6.

Protein Pegylation

Pegylation uses modifications of literature methods (Hershfield, et al., (1991), ibid.; U.S. Pat. No. 6,057,292; Lu, et al., Biochemistry 40(44):13288-13301 (2001); Nektar Therapeutics, 2003 catalog). Activated PEGs include both the linear PEG succinimidyl succinates (mPEG-SPA, MW 5 kDa or MW 20 kDa) and the branched PEG hydrosuccinimides (mPEG$_2$-NHS ester, MW 10 kDa or MW 40 kDa), which are both capped on one end with a methoxy group and available from Nektar Therapeutics; experimental determination of optimal pegylated proteins is normally required (Veronese, et al., J. Bioactive Compatible Polymers 12:196-207 (1997)). Optimal pegylation conditions are determined using different ratios of PAL:PEG (taking into account the molar ratio of protein along with the number of lysines per protein monomer), different pHs, different buffers, various temperatures and incubation times. High PAL protein:PEG derivatization ratios are necessary since native PAL has a large number of lysines (29 and 18 per *Rhodosporidium toruloides* (Rt) and *Anabaena variabilis* monomer, respectively) and because un-modified PAL displays immunoreactivity upon repeated injection in mice and since naked (wild-type) PAL is quickly inactivated upon exposure to proteases. Pegylation reactions are stopped by freezing at −20° C., and the samples will be analyzed by SDS-PAGE, MALDI-TOF mass spectroscopy, activity assessment, proteolytic sensitivity, and immunoreactivity.

Prior to activity, proteolysis, and immune assessment, and in order to remove excess unreacted PEG, reactions are dialyzed against pH 8.5, 0.05 M potassium phosphate buffer overnight at 4° C. with stirring using Tube-O-Dialyzers (GenoTechnology). After protein concentration is determined using the NI protein assay kit (GenoTechnology), PAL activity measurements will be performed on underivatized and PEG derivatized PAL samples using standard reaction conditions, as previously described. Following in vitro characterization, in vivo trials will be conducted with the most promising pegylated therapeutic candidates using the PKU mouse model.

Characterization

Protein concentration is determined using the PAL extinction coefficient (0.5 and 0.75 mg mL$^{-1}$ cm$^{-1}$ for RtPAL and AvPAL, respectively) at 280 nm for non-modified protein samples and for pegylated protein samples the concentration is calculated using the NI Protein Assay (GenoTechnology) that includes sample processing to remove non-protein contaminants that might interfere with accurate protein concentration determination.

PEG-PAL products are characterized with MALDI-TOF MS to determine the number of PEG molecules attached to each PAL monomer, as well as characterized using activity assessment and SDS-PAGE and native gel analysis, to assure retention of activity, complete derivatization, and no loss of tetrameric PAL formation, respectively. For PAL and PEG-PAL samples, MALDI-TOF mass spectroscopic analysis requires the use of 0.5 M urea or 0.025 M guanidine-HCl to improve subunit dissociation and the reproducibility of species detection.

PEG-PAL products are characterized by peptide mapping techniques to determine site-specific pegylation (LC/ESI-MSD), and trinitrobenzene sulfonate (TNBS) to determine the free amine titration before and after pegylation. Peptide mapping determines the relative occupancy of pegylation at a majority of the tryptic peptides that terminate with lysine, however, due to size and multiple adjacent lysine tryptic peptides, not all sites are visible using this technique. The TNBS assay more accurately defines the average number of PEG molecules per mol of enzyme, but gives no information about which sites get pegylated. For this reason, both assays are used and are complementary to each other. Rough estimates of percent derivatization of PAL products by PEG can be determined by SDS-PAGE and native gel analyses. Enzymatic assays are used to assess specific activity before and after pegylation and to provide evidence that there is no loss of the tetrameric PAL structure.

PAL Activity Assay

The PAL activity assay is conducted using a Cary UV spectrophotometer (Cary 50) in the kinetics mode. The activity of PAL with L-phenylalanine substrate is assayed at room temperature (25° C.) by measuring the production of trans-cinnamate monitored by the absorbance increase at 290 nm (Hodgins, (1968), ibid.). The molar extinction coefficient of trans-cinnamic acid at 290 nm is 10,238 liter $M^{-1}$ $cm^{-1}$. Reaction mixtures contain 22.5 mM phenylalanine in 100 mM Tris-HCl buffer, pH 8.5. For standard measurements the final enzyme concentration is 0.0035 mg/mL, but for kinetic studies the enzyme concentration in the assay is adjusted so that the slope at 290 nm per min is in the range of 0.005 to 0.02. Activity data is expressed as specific activity ($\mu mol \times min^{-1}$ $mg^{-1}$). One unit of PAL is defined as that amount of enzyme that produces 1 μmol of trans-cinnamic acid per minute at room temperature.

Example 4

Test of In Vitro Half-Life and Immunogenicity

After biochemical characterization, the most promising PEG-PAL candidates are screened for immunoreactivity against antibodies raised by PKU mice injected with native PAL (non-pegylated) using three different and complementary techniques (Western blot, ELISA, and immunoprecipitation (IP)).

For Western blot analysis, PAL anti-serum (from mice injected with native PAL) is used in a dilution 1:10,000. As a negative control the serum from buffer treated-mice is also used in the same dilution. The secondary antibody, alkaline phosphatase-conjugated goat anti-mouse IgG (Promega), is diluted to 1:5,000 and color is developed using the AP substrate Western Blue (Promega). The ELISA test is performed using Nunc/Immuno Maxisorp plates (Nalge Nunc International) following standard procedures using 1 mg/mL of PAL in PBS and blocking with PBS, 0.05% Tween-20, 2% BSA. The mouse antisera (from native PAL exposed mice) is diluted 1:10,000 in EB block solution (PBS, 0.05% Tween-20, 2% BSA), and a HRP-goat anti-mouse IgG is used as secondary antibody with TMB used for detection at 450 nm.

Immunoprecipitation is used to test for PAL antibody binding. Protein samples (PAL or pegylated PAL) are incubated in TTBS buffer (Tris buffered saline with 0.1% Tween) and PAL activity is measured before adding the antibody sample. Each sample is incubated with 8-fold excess of positive control anti-PAL serum and a duplicate negative control reaction using non-immune mouse serum. After incubation, protein G Sepharose 4 (50%, v/v) is added in excess, taking into account the mouse IgG binding capacity of the beads, and the samples are incubated again at 4° C. overnight with rotation. Supernatants are recovered by centrifugation and the PAL activity of each sample is assayed on the supernatants. The bead pellets are not discarded, so that further analysis by Western blot can be performed. To confirm that antibody-bead binding has occurred, Western blot is used to detect the PAL antigen on the beads. Beads that have been recovered by centrifugation after the PAL binding step are washed several times with TTBS and TBS buffers. Following these rinses, SDS-PAGE loading buffer is added to the beads and the samples are heated at 95° C. for 5 minutes. Samples are then analyzed by Western blot using PAL anti-serum. Enzyme variants showing poor antibody binding have corresponding little PAL in the pelleted bead fractions as detected by Western blot and show higher activities remaining in the supernatant as compared to native un-modified PAL which displays high antibody binding.

Example 5

Test of Protease Sensitivity

Protease mapping studies on native PAL from *R. toruloides* have indicated primary sites of proteolytic sensitivity. Removal of such sites can reduce or eliminate proteolytic sensitivity and contribute to the development of an effective PKU enzyme substitute. However, elimination of such sites for proteolytic sensitivity can result in the reduction or loss of enzyme activity.

After protein engineering has created improved PAL (and PEG-PAL) mutants that retain activity, screening for protease resistance using incubation with a trypsin/chymotrypsin protease cocktail, followed by monitoring for retention of activity (via $OD_{290}$ measurement) and reduced protein cleavage (via PAGE gel analysis) allows for the identification of mutants with appropriate in vitro properties to be used for in vivo testing.

Proteolytic stability will be assessed using incubation with a protease cocktail that approximates the intestinal environment and contains 2.3 mM trypsin, 3.5 mM chymotrypsin, 3.05 mM carboxypeptidase A, and 3.65 mM carboxypeptidase B. Proteolysis testing will involve enzymatic incubations, adding proteases to the PAL solutions, to determine the degree of protease sensitivity for the different protein variants being examined (native or mutant protein with or without pegylation or other chemical modification), including time courses of activity retention and stability retention after protease exposure. SDS-PAGE and MALDI-TOF mass spectrometric mapping experiments will be used to determine the location of any protease sensitive sites (Kriwacki, R. W., et al., J. Biomol. Tech. 9(3):5-15 (1980)). These mapping results will be important to determine primary sites of protease susceptibility (such as the two primary sites already identified), so that all major sensitivity sites can be removed using pegylation protection and/or mutation to remove and/or protect susceptible regions from the PAL architecture.

Example 6

Generation of PEGylated NpPAL and AvPAL

In general, PEGylation for both NpPAL and AvPAL involves mixing the protein with SUNBRIGHT ME-200HS 20 kDa NHS-activated PEG (NOF).

Protocol for PEGylation, standard "HC" method using NETS-activated 20 kDa linear PEG:

1) The protein was evaluated for the presence of endotoxin. A protein solution (0.1 mL) was diluted in 0.9 mL fresh MQ water and tested with a hand-held Charles River apparatus (EndoPTS) for endotoxin at the 0.5 EU/mL sensitivity level. If endotoxin was greater than 0.5 EU/mL, then endotoxin was reduced initially by Mustang E filtration, followed by Sterogene Etox resin, or by further chromatographic purification. Reduction was limited but sufficiently useful by passage over DEAE FF (Amersham) at pH 7.8.

2) Concentration and buffer exchange of protein. The protein was concentrated to greater than 25 mg/mL but less than or equal to 75 mg/mL and buffer exchanged to 50 mM $KPO_4$, pH 8.5. If a spin filter was used to prepare this concentration, the filter was first tested for endotoxin by spinning at reduced speed and time (3000 rpm, 3 minutes) with buffer alone, then testing the retained buffer for endotoxin in the same way as the protein in step 1. The buffer batch record/recipe for 50 mM KPO4, pH 8.5 consisted of water (QS to 1 L), potassium phosphate dibasic (8.4913 g/L of 48.75 mM), and potassium phosphate monobasic (0.17011 g/L of 1.25 mM). The solution was filtered through a 0.2 µm filter and stored at room temperature. The concentrated product was slowly filtered (1-2 mL/min) through a Mustang E filter acrodisc. A sample diluted and blanked with sterile TBS, pH 7.5 was measured at A280 to determine protein concentration. The extinction coefficient was 0.83 for NpPAL and 0.75 for AvPAL.

3) PEGylation of NpPAL and AvPAL. PEG normally stored at −80° C. was warmed to room temperature. KPO4 buffer was added to PEG to resuspend by vortexing at maximum speed, and shaking tube hard in hand to ensure all large chunks were suspended. Alternatively, the PEG was resuspended in water at pH~5). The protein was added to the well-suspended PEG solution within one minute of having first wetted the PEG and mixed by very gentle inversion. Tubes wrapped in aluminum foil were placed on the axis of a rocker and rocked very gently at room temperature for 3 hours. The tubes were filled with TBS (pH 7.5) and sterile filtered. The suspensions were either formulated immediately or stored at 4° C. until ready for formulation.

4) Formulation. The formulation buffer recipe/batch record consisted of water (QS to 1 L), Tris-Base (3.2 mM), Tris-HCl (16.8 mM), and sodium chloride; the buffer solution was filtered through a 0.2 µm filter and stored at room temperature. The buffer solution was subjected to tangential flow filtration using a Vivaflow 50 (smaller lots) or Vivaflow 200 (larger lots) with a 100 MWCO regenerated cellulose membrane. The solution was flushed with MQ water, 0.1 N NaOH, and 200 mL water again. The solution was equilibrated with TBS, pH 7.5 at 50 mL/min cross-flow. The pH of the permeate was determined to ensure a pH of 7.5.

The solution was buffer exchanged by first diluting with TBS approximately 3-fold and returning to original volume at least four times. Cross-flow was typically 180-200 mL/min for both Vivaflow 50 and 200.

The final product was filtered through Mustang E. The presence of endotoxin was evaluated after diluting 0.1 mL with 1.9 mL sterile fresh water. If endotoxin was greater than 1 EU/mL, reduction was conducted with Sterogene Etox gel. Formulated, sterile PEGylated NpPAL or AvPAL were sealed in vials and placed at −70° C. until ready for in vivo studies.

Example 7

Generation of AvPAL Variants (Cysteine Mutants)

Amino acid substitutions were made in the AvPAL polypeptide to reduce aggregation that occurs in bacterially expressed, recombinant proteins. Protein aggregation can reduce enzyme activity and/or increase immunogenicity in vivo. One such form of aggregation occurs as a result of formation of inter-chain disulfide bonds. To minimize this possibility, various AvPAL cysteine residues, alone or in combination, were replaced with serine residues.

The AvPAL polypeptide has 6 cysteine residues, at positions 64, 235, 318, 424, 503 and 565 (SEQ ID NO:4). The following AvPAL single cysteine mutants were generated: AvPAL_C64S (SEQ ID NO:7), AvPAL_C318S (SEQ ID NO:8), AvPAL_C503S (SEQ ID NO:9), and AvPAL_C565S (SEQ ID NO:10). An AvPAL double cysteine mutant, AvPAL 55655C503S (SEQ ID NO:11), was also generated. FIG. 5A-5E shows the amino acid sequences of these AvPAL cysteine mutants.

Cloning

The AvPAL gene was amplified from *Anabaena variabilis* genomic DNA (ATCC 29413-U, Qiagen DNeasy Kit) with forward primer AvarPALfor (5'-CACTGTCATATGAAGA-CACTATCTCAAGCACAAAG-3') (SEQ ID NO:18) and reverse primer AvarPALrev (5'-CACTGTCTCGAGATG-CAAGCAGGGTAAGATATCTTG-3') (SEQ ID NO:19). The resulting PCR product was treated with Taq and then ligated into pCR2.1 TOPO TA (Invitrogen). The resulting plasmid was named 1p40.

A 5' NheI site was added and an internal NheI site was removed by SOE-PCR. The upstream AvPAL fragment was amplified from 1p40 with forward primer N-Nhe-AvPAL (5'-CACTGTGCTAGCATGAAGACACTATCTCAAGCA-CAAAG-3') (SEQ ID NO:20) and reverse primer Nhe-AvPALrev (5'-GGAAATTTCCTCCATGATAGCTGGCT-TGGTTATCAACATCAATTAGTGG-3') (SEQ ID NO:21), and the downstream AvPAL fragment was amplified from 1p40 with forward primer Nhe-AvPALfor (5'-CCACTAAT-TGATGTTGATAACCAAGCCAGCTATCATGGAG-GAAATTTCC-3') (SEQ ID NO:22) and reverse primer AvPALrev-r (5'-ACAGTGGCGGCCGCTTAATG-CAAGCAGGGTAAGATATCTTG-3') (SEQ ID NO:23). In a single PCR reaction, the two PCR products were annealed and extended with DNA polymerase to produce the full-length AvPAL gene, and then amplified with primers N-Nhe-AvPAL and AvPALrev-r. The resulting PCR product was digested with NheI, blunted with Klenow, digested with NotI, and ligated into the pET28a+ vector (prepared by digestion with NdeI, blunting with Klenow, and digestion with NotI). The resulting plasmid was named 3p86-23.

New restriction sites were added by PCR. AvPAL was amplified from plasmid 3p86-23 with forward primer AvEcoRIfor (5'-CACTGTGAATTCATGAAGACAC-TATCTCAAGCACAAAG-3') (SEQ ID NO:24) and reverse primer AvSmaIrev (5'-CACTGTCCCGGGTTAATG-CAAGCAGGGTAAGATATCT-3') (SEQ ID NO:25). The resulting PCR product was digested with EcoRI and SmaI and ligated into EcoRI- and SmaI-digested pIBX7 vector. The resulting plasmid was named 7p56 Av3.

Cysteine Mutants

Two cysteine codons in the AvPAL gene, corresponding to positions 503 and 565 of the AvPAL polypeptide, were substituted with serine codons by site-directed mutagenesis (QuickChange XL II, Stratagene). The cysteine codon at position 503 was changed to a serine codon in plasmid 7p56 Av3 by PCR with forward primer Av_C503S (5'-GTCAT-TACGATGCACGCGCC TCTCTATCACCTGCAACTGAG-3') (SEQ ID NO:26) and reverse primer Av_C503Srev (5'-CTCAGTTGCAGGTGA-TAGAGAGGCGCGTGCATCGTAATGAC-3') (SEQ ID NO:27). The serine codon is underlined and the G to C mutation in the coding strand (C to G mutation in the non-coding strand) is indicated in bold. The resulting plasmid was named j282. The cysteine codon at position 565 was changed to a serine codon in plasmid j282 with forward primer Av_C565S (5'-CAGTTCAAGATATCTTACCC TCCTTGCATTAACCCGGGCTGC-3') (SEQ ID NO:28) and reverse primer Av_C565Srev (5'-GCAGCCCGGGT-TAATGCAAGGAGGGTAAGATATCTTGAACTG-3') (SEQ ID NO:29). The serine codon is underlined and the G to C mutation in the coding strand (C to G mutation in the non-coding strand) is indicated in bold. The resulting plasmid was named j298a.

Cysteine codons in the AvPAL gene at positions 64, 318 and 565 of the AvPAL polypeptide were similarly substituted with serine codons using the following primer pairs: C64S, forward primer Av_C64S (5'-GCAGGGTATTCAG-GCATCTTCTGATTACATTAATAATGCTGTTG-3') (SEQ ID NO:30) and reverse primer Av_C64Srev (5'-CAACAG-CATTATTAATGTAATCAGAAGATGCCTGAATACC CTGC-3') (SEQ ID NO:31); C318S, forward primer Av_C318S (5'-CAAGATCGTTACTCACTCCGA TCCCTTCCCCAGTATTTGGGGC-3') (SEQ ID NO:32) and reverse primer Av_C318Srev (5'-GC-CCCAAATACTGGGGAAGGGATCGGAGTGAGTAAC GATCTTG-3') (SEQ ID NO:33); and C565S, forward primer Av_C565S (SEQ ID NO:28) and reverse primer Av_C565Srev (SEQ ID NO:29). The serine codons are underlined, and the G to C mutations in the coding strands and the C to G mutations in the non-coding strands are indicated in bold.

Example 8

In Vitro Enzyme Activity of AvPAL Variants (Cysteine Mutants)

The purpose of this study was to determine the effect of serine substitution of the various cysteine residues in the AvPAL polypeptide on in vitro phenylalanine ammonia-lyase (PAL) enzyme activity.

AvPAL variants (i.e., cysteine mutants) were cloned as described in EXAMPLE 7. The AvPAL cysteine mutant expression plasmids were transformed into bacteria and the AvPAL cysteine mutant polypeptides were expressed as described in EXAMPLE 1 and purified as described in EXAMPLE 2.

The wild-type (WT) AvPAL and AvPAL cysteine mutants were tested for in vitro PAL enzyme activity as described in EXAMPLE 3. Table 1 shows that compared to unpegylated WT AvPAL, the in vitro PAL specific activity of the purified, unpegylated AvPAL cysteine mutant proteins was reduced by serine substitution of the cysteine residue at position 64 (AvPAL_C64S), but was not adversely affected by serine substitution of the cysteine residues at either of positions 503 or 565, or at both positions 503 and 565 (AvPAL_C503S, AvPAL_C565S, and AvPAL_C565SC503S, respectively).

TABLE 1

Specific Activity of AvPAL Cysteine Mutants

| AvPAL Protein | PEGylation | Specific Activity (U/mg) |
| --- | --- | --- |
| WT AvPAL | − | 1.7 |
| AvPAL_C503S | − | 1.9 |
| AvPAL_C64S | − | 1.3 |
| AvPAL_C565S E1 | − | 2.0 |
| AvPAL_C565S E2 | − | 2.1 |
| AvPAL_C565SC503S | − | 2.2 |
| WT AvPAL | + | 1.1 |
| AvPAL_C565SC503S | + | 1.1 |

To determine whether the introduction of the serine residues had any effect on enzymatic activity of pegylated AvPAL proteins, the WT AvPAL and double cysteine mutant, AvPAL_C565SC503S, were pegylated as described in EXAMPLE 6. Table 1 shows that the in vitro PAL specific activity of the pegylated AvPAL protein was not adversely affected by serine substitution of the cysteine residues at both positions 503 and 565.

Example 9

In Vitro Biochemical Characterization of AvPAL Variants (Cysteine Mutants)

The purpose of this study was to determine the effect of serine substitution of the various cysteine residues in the AvPAL polypeptide on: (1) accelerated stability; (2) aggregate formation; and (3) site-specific pegylation.
Accelerated Stability The effect of serine substitution of cysteine residues in AvPAL on in vitro stability was determined by storing the purified AvPAL cysteine mutants, either pegylated or unpegylated, for various time periods at 37° C., and then measuring the in vitro PAL specific activity of these proteins as described in EXAMPLE 3.

Wild-type AvPAL and AvPAL cysteine mutants, either upegylated or pegylated, were prepared as described in EXAMPLE 8.

Figure 3:
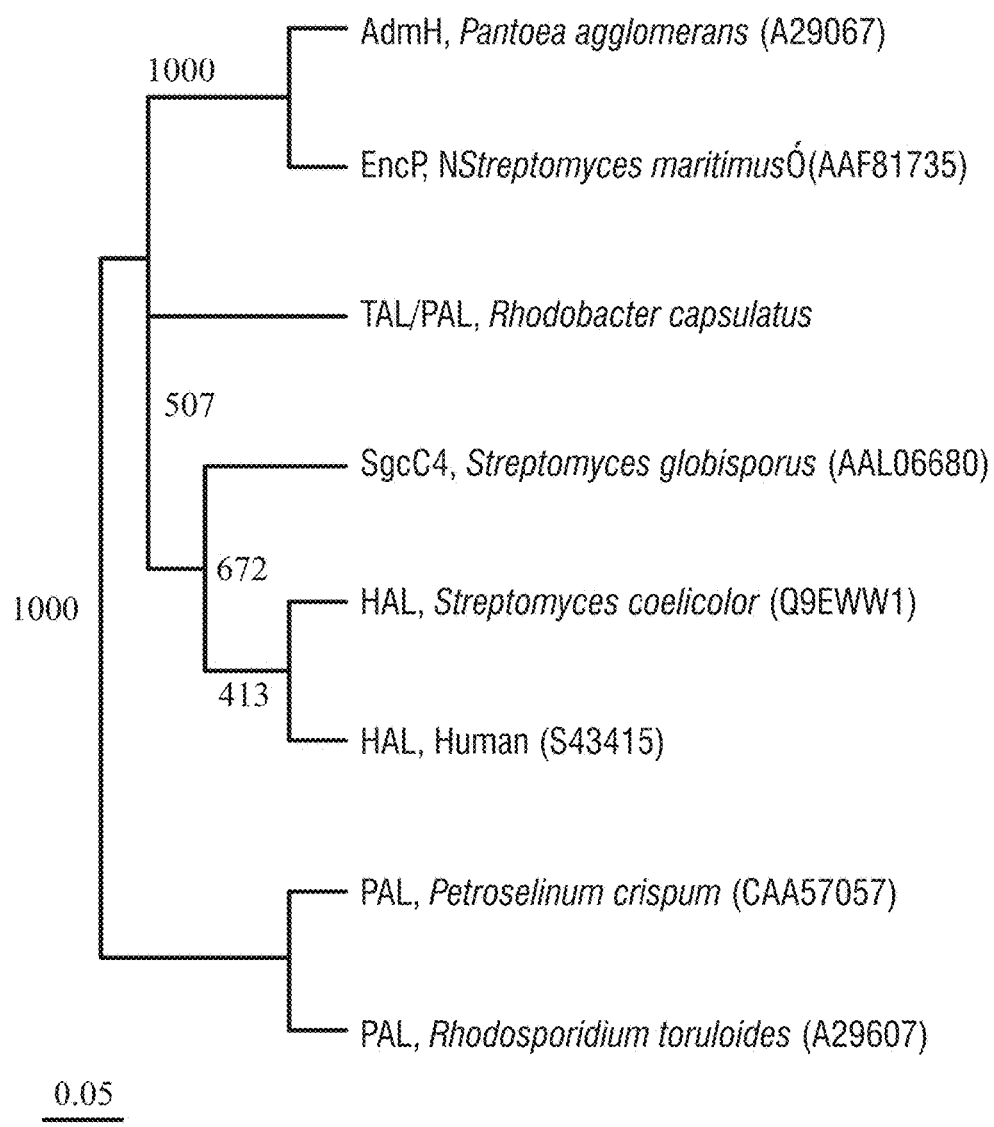
FIG. 3 Relatedness tree of aromatic amino acid ammonia-lyases from prokaryotes and eukaryotes. Sequences were retrieved from GenBank (accession numbers are given in parentheses) and aligned with ClustalX (1.83) using the Neighbor Joining Method.
Figure 6A:
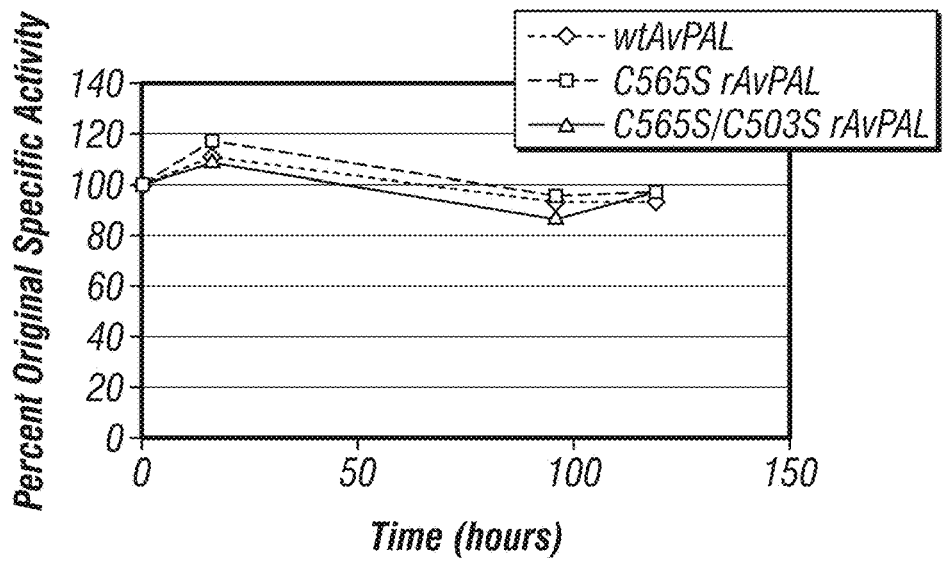
FIGS. 6A-6B show effect of variants of unpegylated or pegylated *Anabaena variabilis* PAL (AvPAL) on in vitro PAL specific enzyme activity. (A) Effect of cysteine to serine substitutions at position 565 or both positions 565 and 503 of unpegylated AvPAL on in vitro PAL specific enzyme activity after incubation for various lengths of time at 37° C. (B) Effect of cysteine to serine substitutions at position 565 or both positions 565 and 503 of pegylated AvPAL on in vitro PAL specific enzyme activity after incubation for various lengths of time at 37° C.
Figure 6B:
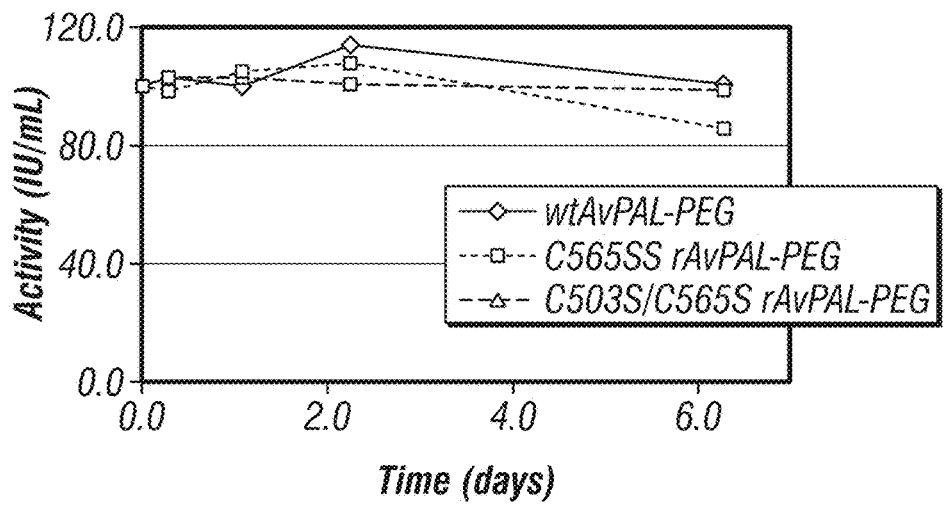

As shown in FIG. 6A, the specific activities of the unpegylated AvPAL proteins were stable for at least 5 days at 37° C., and were not adversely affected by serine substitution of the cysteine residues at position 565, or at both positions 503 and 565. Similarly, as shown in FIG. 6B, the specific activities of the pegylated AvPAL proteins were stable for at least 6 days at 37° C. The single cysteine AvPAL mutant, AvPAL_C565S, showed somewhat reduced stability compared to wild-type AvPAL and the double cysteine AvPAL mutant, AvPAL_C565SC503S, after 6 days at 37° C.
Aggregate Formation The effect of serine substitution of cysteine residues in AvPAL on formation of protein aggregates in solution was determined by separating the purified, unpegylated wild-type AvPAL and AvPAL cysteine mutants by either denaturing and native gel electrophoresis or by SEC-HPLC.

The purified AvPAL preparations were separated by gel electrophoresis under either denaturing conditions (4-12% NuPAGE Bis-Tris) or native conditions (8% Tris-Gly, pH 8.3). The separated AvPAL proteins were stained with Coomassie Blue.

The purified AvPAL preparations were separated by SEC-HPLC. AvPAL proteins were loaded onto a TSK gel column (G3000SWxl, 7.8 mm×30 cm, 5 μm (Tosoh Bioscience, LLC)) in 20 mM Na-phosphate, 300 mM NaCl, pH 6.9, and eluted at a flow rate of 0.5 mL/min. The separated AvPAL proteins were analyzed on an Agilent series 1100 spectrometer.

Figure 7A:
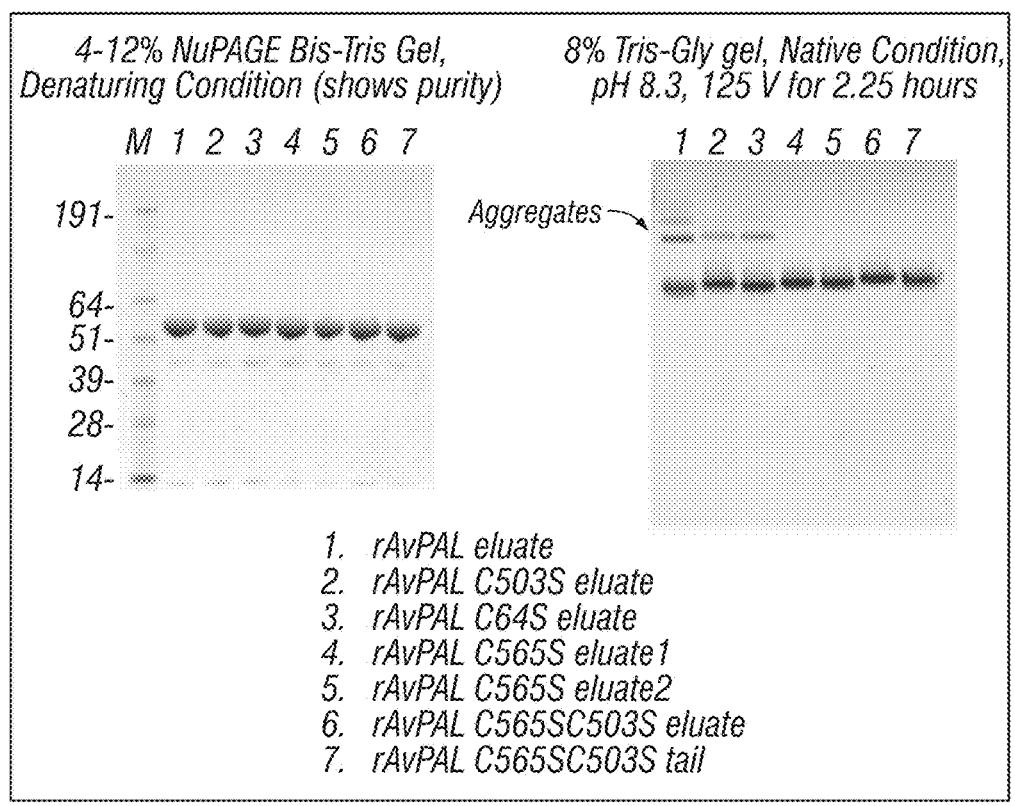
FIGS. 7A-7B show effect of cystein to serine substitution in AvPAL on formation of protein aggregates. (A) Effect of cysteine to serine substitutions in AvPAL on formation of protein aggregates in solution as analyzed by gel electrophoresis under denaturing conditions (left panel) or native conditions (right panel). (B) Effect of cysteine to serine substitutions in AvPAL on formation of protein aggregates in solution as analyzed by SEC-HPLC.
Figure 7B:
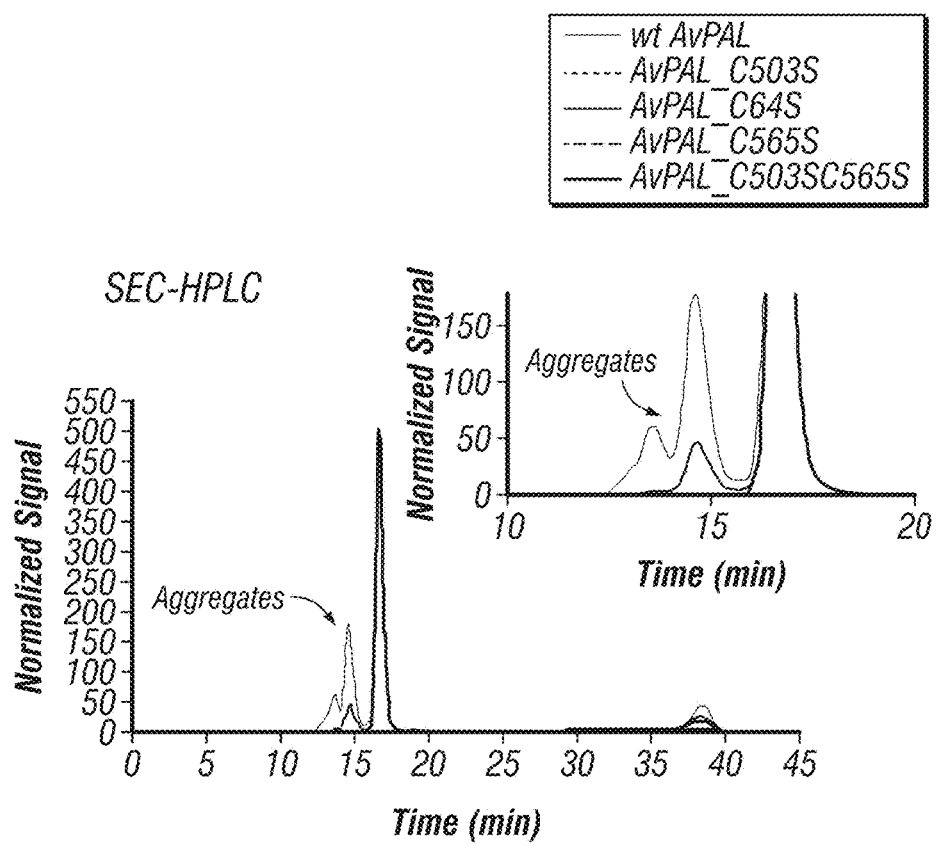

Aggregates were present in the wild-type AvPAL preparation and in the AvPAL_C503S and AvPAL_C64S preparations, but not in the AvPAL_C565S and AvPAL_C565S C503S preparations, as judged by either gel electrophoresis (FIG. 7A) or SEC-HPLC (FIG. 7B).
Site-Specific Pegylation The effect of serine substitution of cysteine residues in AvPAL on site-specific pegylation was determined by pegylating the wild-type AvPAL and double cysteine mutant AvPAL_C503SC565S as described in EXAMPLE 6, and then comparing the relative pegylation at the AvPAL lysine residues: K2, K10, K32, K115, K145, K195, K301, K335, K413, K419, K493, K494 and K522.

Approximately 100 μg (10 μL at 10 μs/μL) of unpegylated or pegylated AvPAL proteins were denatured in 8 M urea. The denatured proteins were then digested in a 100 μL reaction volume with trypsin in 0.8 M urea at pH 8.2 overnight (~20 hours) at 37° C. The trypsin-digested proteins were reduced by treatment with 1 μL of 1 M DTT for 1 hour at 37° C., followed by quenching with 3 μL 15% TFA. Digested proteins were separated on a C18 reverse-phase column. Percent pegylation of each of the pegylated AvPAL peptides was calculated by subtractive peptide mapping of the corresponding unpegylated peptide.

Figure 8:
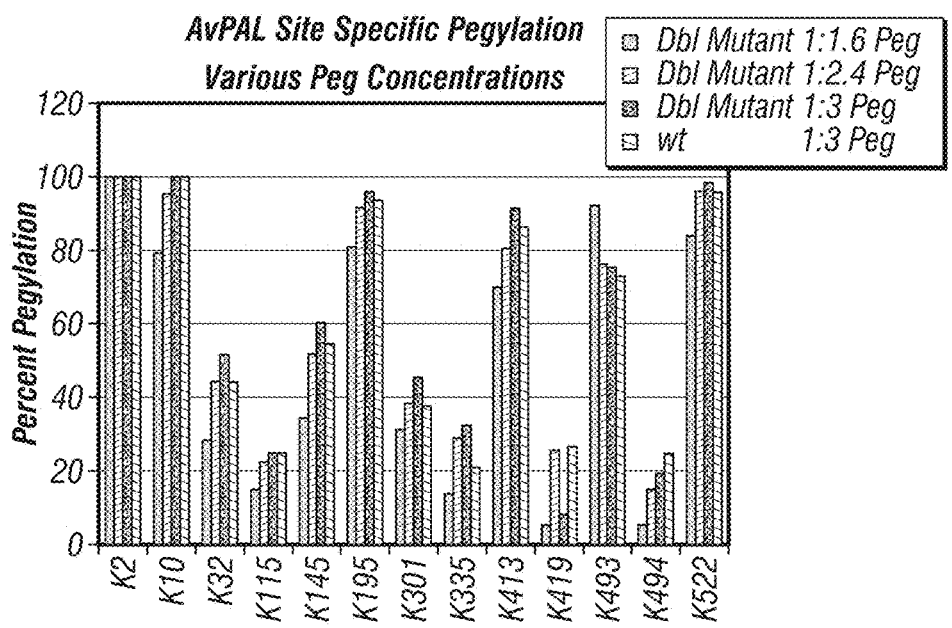
FIG. 8 Effect of cysteine to serine substitutions at positions 565 and 503 (dbl Mutant) in AvPAL on site-specific pegylation at various PEG concentrations.

As shown in FIG. 8, at a ratio of AvPAL protein:PEG of 1:3, there was no striking difference in the percent pegylation of any of the lysine (K) residues with the possible exception of K419, in which the percent pegylation of the double cysteine mutant C565SC503S was lower compared to wild-type AvPAL. However, the results obtained using the double cysteine mutant at increasing AvPAL protein:PEG ratios, in which no dose-response relationship was observed, taken together with the relatively small percent pegylation, indicates that the observed differences at K1419 are not likely to be meaningful. Thus, serine substitution of cysteine residues at positions 503 and 565 does not appear to affect site-specific pegylation of AvPAL.

Example 10

Mechanism of Aggregation of AvPAL Proteins

Studies were performed to investigate the mechanism of aggregation of bacterially expressed AvPAL proteins.

Concentrating the purified AvPAL preparations, and incubating the concentrated protein solutions for 2 hours at 37° C., accelerated aggregation of purified AvPAL proteins in solution. Aggregation was detected by separating the AvPAL proteins by SEC-HPLC. To determine whether disulfide cross-linking was responsible for the aggregation, 50 mM dithiothreitol (DTT) was added to the concentrated protein solution, followed by incubation for 2 hours at 37° C.

AvPAL proteins expressed in bacteria were purified as described in EXAMPLE 2, and concentrated using a spin filter (Millipore Biomax—10K NMWL). Proteins were spun at about 15,000 g for a few minutes in an Eppendorf Centrifuge 5415C. For cysteine mutants that tend to aggregate (e.g., AvPAL_C503S and AvPAL_C64S), proteins were concentrated to about 20 mg/mL and incubated for 2 hours at 37° C. For cysteine mutants that are resistant to aggregation (e.g., AvPAL_C565S and AvPAL_C565SC503S), proteins were concentrated to about 40 mg/mL and incubated for 2 hours at 37° C.

As shown in Table 2, preparations of purified AvPAL cysteine mutants AvPAL_C64S and AvPAL_C503S formed aggregates upon incubation for 2 hours at 37° C. As expected, this aggregation was exacerbated when the AvPAL proteins were concentrated prior to incubation for 2 hours at 37° C. The aggregation could be blocked by exposure of the concentrated proteins to DTT, indicating that the aggregation is due to disulfide cross-linking. In contrast, the preparations of purified AvPAL cysteine mutants AvPAL_C565S and AvPAL_C565SC503S did not form aggregates upon incubation for 2 hours at 37° C., indicating that the cysteine residue at position 565 is involved in aggregation of AvPAL via disulfide cross-linking.

TABLE 2

Disulfide Cross-link Related Aggregation of AvPAL Cysteine Mutants

| AvPAL Protein | Treatment | Aggregate Formation |
| --- | --- | --- |
| AvPAL_C503S | 37° C./2 h | + |
| AvPAL_C64S | 37° C./2 h | + |
| AvPAL_C565S E1 | 37° C./2 h | − |
| AvPAL_C565S E2 | 37° C./2 h | − |
| AvPAL_C565SC503S | 37° C./2 h | − |
| AvPAL_C503S | Concentrate + 37° C./2 h | ++ |
| AvPAL_C64S | Concentrate + 37° C./2 h | ++ |
| AvPAL_C565S E1 | Concentrate + 37° C./2 h | − |
| AvPAL_C565S E2 | Concentrate + 37° C./2 h | − |
| AvPAL_C565SC503S | Concentrate + 37° C./2 h | − |
| AvPAL_C503S | Conc. + DTT + 37° C./2 h | − |
| AvPAL_C64S | Conc. + DTT + 37° C./2 h | − |
| AvPAL_C565S E1 | Conc. + DTT + 37° C./2 h | − |
| AvPAL_C565S E2 | Conc. + DTT + 37° C./2 h | − |
| AvPAL_C565SC503S | Conc. + DTT + 37° C./2 h | − |

To determine which cysteine residues exist as free sulfhydryls, a purified AvPAL preparation was denatured in the presence of 8 M urea, alkylated by iodoacetamide, digested with trypsin, and analyzed by LC/MS. All of the AvPAL cysteine residues were labeled by iodoacetamide, indicating that all of the cysteine residues of bacterially expressed AvPAL exist as free sulfhydryls (data not shown).

To determine which cysteine residues are present on the surface of the native protein, a purified AvPAL preparation was first treated with N-ethylmaleimide (NEM), then denatured in the presence of 8 M urea, alkylated by iodoacetamide, digested with trypsin, and analyzed by LC/MS. The cysteine residues at positions 235 and 424 were not alkylated by NEM, and the cysteine residue at position 318 was only partially alkylated by NEM, indicating that the cysteine residues at positions 64, 503 and 565 are on the surface of native AvPAL and the cysteine residue at position 318 is partially exposed on the surface of native AvPAL (data not shown).

To determine which cysteine residues are involved in the inter-chain disulfide cross-linking, 67 μL of a 0.7 mg/mL solution of purified, unpegylated wild-type AvPAL preparation was denatured and alkylated in 8 M urea containing 20 mM iodoacetamide for 1 hour at 37° C., and then digested in a 100 μL reaction volume with trypsin at pH 8.2 overnight (~17.5 hours) at 25° C. The trypsin-digested proteins were separated and analyzed by mass spectrometry, in which peptides corresponding to the predicted disulfide pairs were identified and quantitated as total ion counts (TIC).

Table 3 shows that disulfide pairs were detected for C503-0503, C503-0565, C565-C318 and C565-0565. The cysteine residues at position 565, and to a lesser extent at position 503, were found in disulfide pairs in the purified AvPAL preparation.

TABLE 3

Aggregate Disulfide Pairs

| Disulfide Pair | Results (TIC/1000) |
| --- | --- |
| C64-C318 | n.d.# |
| C64-C64 | n.d. |
| C64-C503 | n.d. |
| C64-C565 | n.d. |
| C503-C318 | n.d. |
| C503-C503 | 11 |
| C503-C565 | 112 |
| C565-C318 | 13 |

TABLE 3-continued

Aggregate Disulfide Pairs

| Disulfide Pair | Results (TIC/1000) |
|---|---|
| C565-C565 | 37 |
| C318-C318 | n.d. | not detected

Studies were performed to determine whether additional mechanisms besides disulfide cross-linking might be involved in AvPAL protein aggregation.

Figure 9:
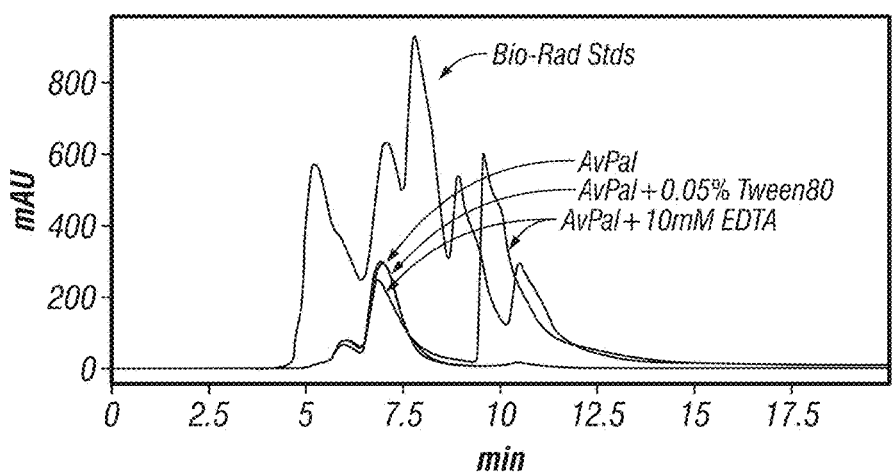
FIG. 9 Effect of treatment of AvPAL with 0.05% Tween80 or 10 mM EDTA on formation of protein aggregates in solution as analyzed by SEC-HPLC.

Purified AvPAL preparations were incubated with either 0.05% Tween or 10 mM EDTA, and then separated by SEC-HPLC as described in EXAMPLE 9. Tween reduces protein aggregation due to hydrophobic interactions, and EDTA reduces protein aggregation due to the presence of divalent cations. As shown in FIG. 9, exposure to 0.05% Tween or 10 mM EDTA had no effect on AvPAL protein aggregation. The additional peak at 10 minutes in the 10 mM EDTA treated AvPAL is due to absorbance of EDTA at 210 nm.

Figure 10A:
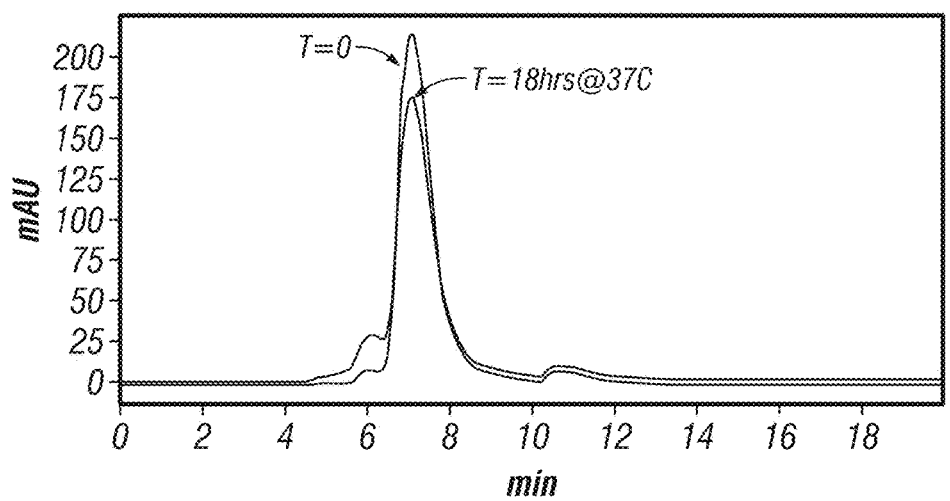
FIGS. 10A-10B show effect of treatment of AvPAL by only dithiotreitol (DTT) or by a combination of DTT and N-ethylmaleimide (NEM) on formation of protein aggregates. (A) Effect of treatment of AvPAL by dithiotreitol (DTT) on formation of protein aggregates in solution as analyzed by SEC-HPLC. (B) Effect of treatment of AvPAL by DTT and N-ethylmaleimide (NEM) on formation of protein aggregates in solution as analyzed by SEC-HPLC.
Figure 10B:
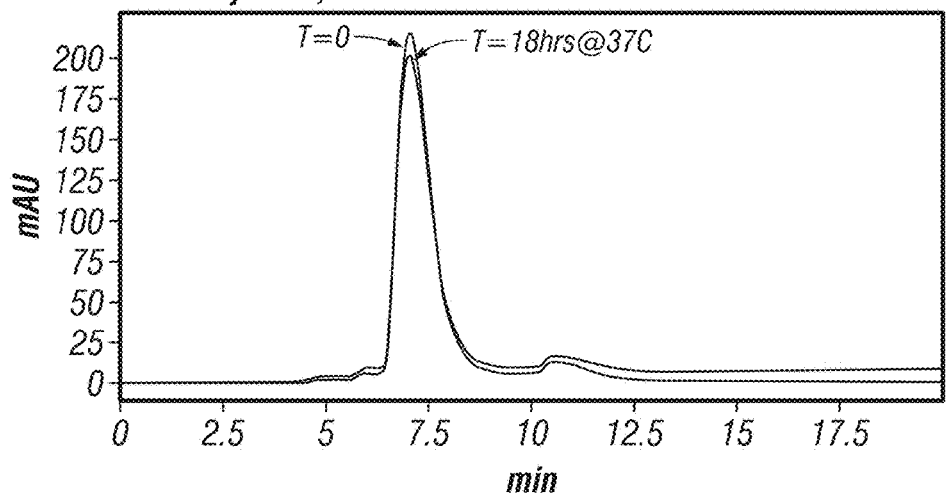

To further investigate the role of disulfide cross-linking in AvPAL protein aggregation, purified AvPAL was reduced by treatment with DTT and then desalted prior to separation by SEC-HPLC. As shown in FIG. 10A, AvPAL protein aggregation was minimized by treatment with DTT, and aggregates re-formed following incubation for 18 hours at 37° C. In contrast, as shown in FIG. 10B, aggregates did not re-form once the AvPAL surface cysteines were modified (i.e., alkylated) by treatment with N-methylmaleimide (NEM) after DTT exposure, but before desalting and incubation for 18 hours at 37° C.

Based on the above, aggregation of bacterially expressed AvPAL appears to be due solely to formation of inter-chain disulfide bonds, and not due to hydrophobic effects or presence of divalent cations. The cysteine residues at positions 565 and 503 are involved in formation of inter-chain disulfide bonds in AvPAL preparations.

Example 11

Liquid Formulations of PEGylated Forms of AvPAL Variants (Cysteine Mutants)

Studies were performed to investigate the effect of various excipients, e.g., stabilizers, on the accelerated stability of a PEGylated form of an AvPAL polypeptide variant (e.g., with serine substitution of the cysteine residues at positions 503 and 565) in formulations provided herein.

The pegylated AvPAL double cysteine mutant AvPAL_C565SC503S was prepared as described in EXAMPLE 7.

Accelerated stability of different formulations of pegylated AvPAL_C565SC503S was determined using an in vitro activity assay, either a cuvette assay or a plate assay. For the cuvette assay, purified pegylated AvPAL_C565SC503S was diluted in TBS dilution buffer and then added to an assay buffer containing 22.5 mM Phe, 100 mM Tris-HCl, pH 8.5. After incubation for 2 minutes at 30° C., the amount of trans-cinnamic acid (t-CA) released was measured by absorbance at 290 nm. For the plate assay, purified pegylated AvPAL_C565SC503S was diluted in TBS dilution buffer plus BSA/Phe/Brij and then added to an assay buffer containing 22.5 mM Phe, 100 mM Tris-HCl, pH 8.5. After incubation for 10-20 minutes at 30° C., the amount of trans-cinnamic acid (t-CA) released was measured by absorbance at 290 nm. One IU of PAL activity is equal to 1 µMol TCA/min.

In a first accelerated stability study, the effect of pH on stability of the pegylated double cysteine mutant AvPAL AvPAL_C565SC503S was evaluated. Purified pegylated AvPAL_C565SC503S was pre-formulated in 10 mM buffer and 140 mM NaCl at various pH, from 4 to 9. Buffers tested: citrate (pH 4), acetate (pH 5), histidine (pH 6), phosphate (pH 7), Tris (pH 7.5, pH 8) and arginine (pH 9). After storing the enzyme formulations for up to 30 days at 4° C., 25° C. or 37° C., in vitro activity was measured. A total loss of PAL enzyme activity was observed at pH 4. A pH range from 7 to 8 was chosen for further evaluation.

In a second accelerated stability study, the effect of pH and a variety of excipients on stability of the pegylated AvPAL double cysteine mutant AvPAL_C565SC503S was evaluated. Purified pegylated AvPAL_C565SC503S was pre-formulated in 10 mM Tris and 140 mM NaCl at pH 7, 7.5 or 8.0 in the absence or presence of 0.5% EDTA, 0.5% EDTA plus 0.5% ascorbic acid or 0.5% EDTA plus 5 mM methionine (Met). After storing the enzyme formulations for up to 60 days at 4° C., 25° C. or 37° C., in vitro activity was measured. pH 7.0 and 7.5 appeared equivalent in maintaining enzyme activity, EDTA had little or no effect on enzyme activity, and the anti-oxidants ascorbic acid and methionine negatively affected enzyme activity.

In the same accelerated stability study, the effect of pegylation of the AvPAL double cysteine mutant AvPAL_C565SC503S was evaluated. The rate of loss of enzyme activity was similar between unpegylated and pegylated AvPAL_C565SC503S.

In a third accelerated stability study, the effect of enzyme substrate and product as excipient on stability of the pegylated AvPAL double cysteine mutant AvPAL_C565SC503S was evaluated. Purified pegylated AvPAL_C565SC503S at approximately 12 mg/mL (0.2 mM) was pre-formulated in 10 mM Tris and 140 mM NaCl at pH 7.5 in the absence or presence of 1 mM Phe (substrate at 5 moles per mole active site), 2 mM TCA (product at 10 moles per mole active site) or 0.05% Tween 80 (a surfactant). After storing the enzyme formulations for various times at 4° C., 25° C. or 37° C., in vitro activity was measured weekly. Both Phe and t-CA significantly increased stability of the enzyme, whereas Tween had no effect on enzyme stability.

Figure 11:
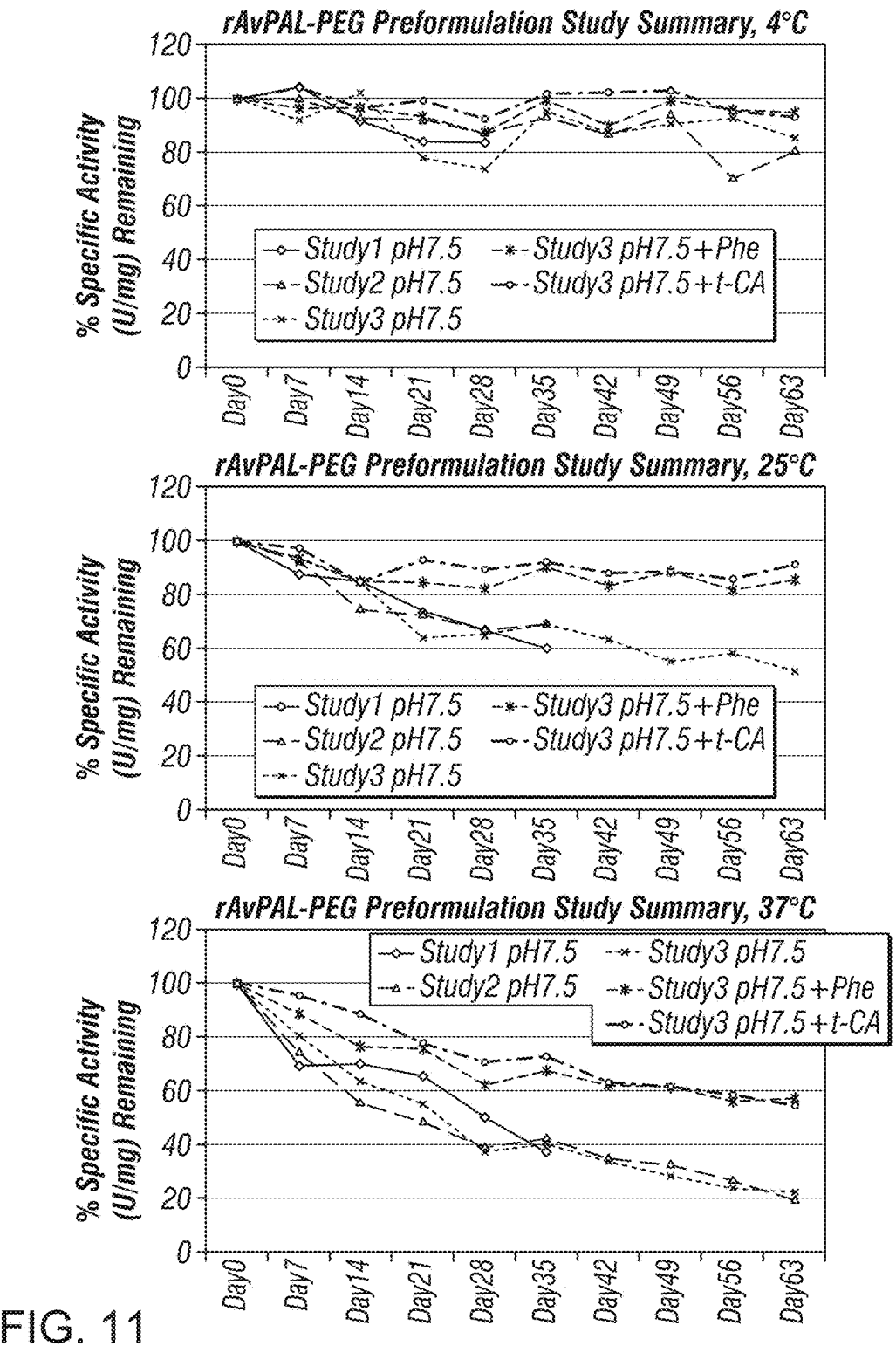
FIG. 11 Effect of Phe and trans-cinnamic acid (t-CA) as indicated on the enzyme activity of a pegylated AvPAL with cysteine to serine substitutions at positions 565 and 503 (AvPAL_C565SC503S) (rAV-PAL-PEG) stored for various times (days) at 4° C. (top panel), at 25° C. (middle panel) and at 37° C. (bottom panel).

A summary of the accelerated stability studies 1, 2 and 3 is shown in FIG. 11.

In a fourth accelerated stability study, the effect of Phe and t-CA at low concentrations as excipient on stability of the pegylated AvPAL double cysteine mutant AvPAL_C565SC503S was evaluated. Purified pegylated AvPAL_C565SC503S at approximately 12 mg/mL (0.2 mM) was pre-formulated in 10 mM Tris and 140 mM NaCl at pH 7.5 in the absence or presence of 0.4 mM Phe (substrate at 2 moles per mole active site) or 0.4 mM TCA (product at 2 moles per mole active site). After storing the enzyme formulations for various times at 4° C., 25° C. or 37° C., in vitro activity was measured weekly. Both Phe and t-CA at low concentration were effective at stabilizing enzyme activity.

Figure 12:
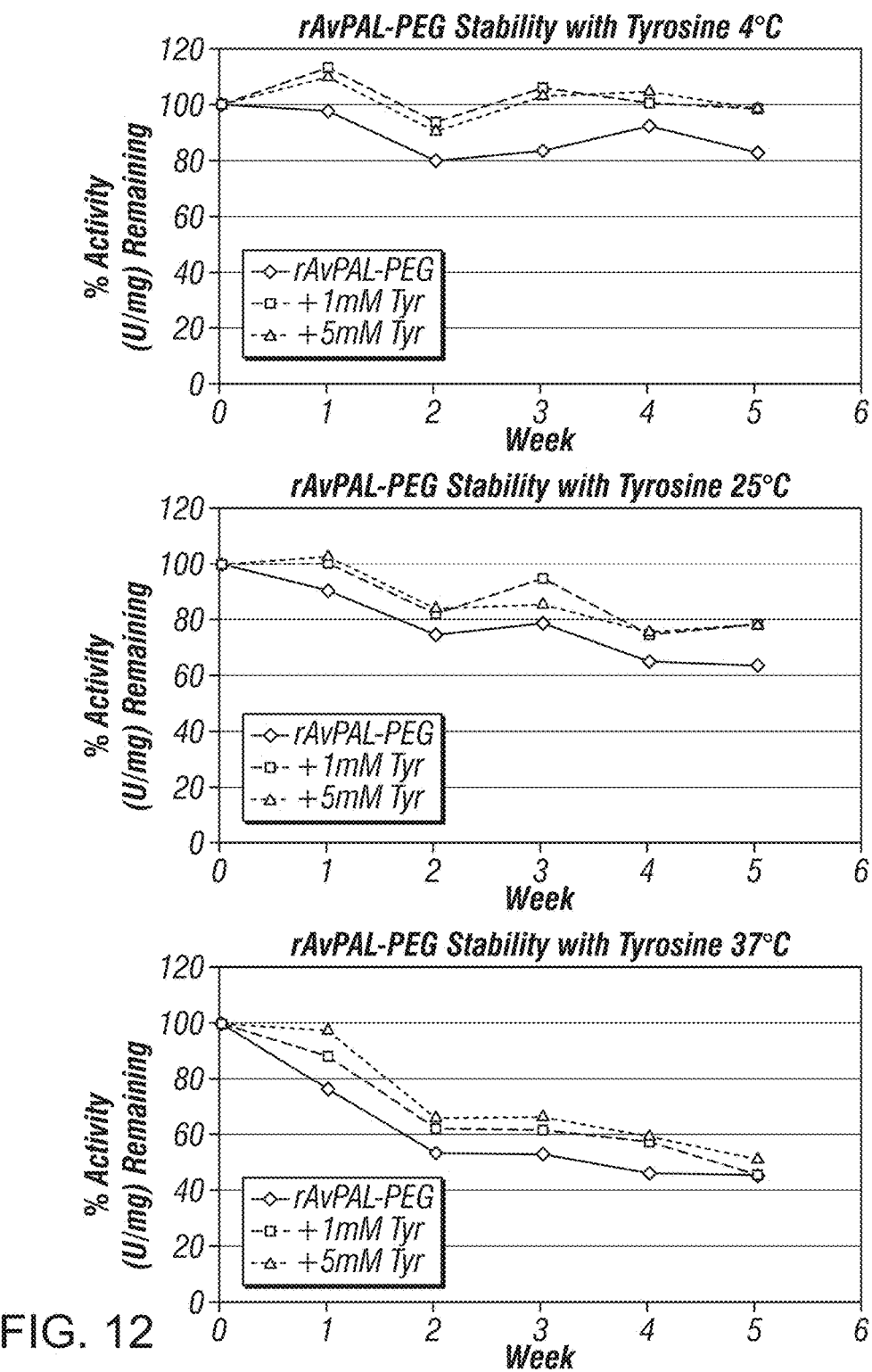
FIG. 12 Effect of tyrosine (Tyr) at 1 and 5 mM as indicated on the enzyme activity of a pegylated AvPAL with cysteine to serine substitutions at positions 565 and 503 (AvPAL_C565SC503S) (rAV-PAL-PEG) stored for various times (days) at 4° C. (top panel), at 25° C. (middle panel) and at 37° C. (bottom panel).

In a fifth accelerated stability study, the effect of a weak enzyme substrate, tyrosine (Tyr), as excipient on stability of the pegylated AvPAL double cysteine mutant AvPAL_C565SC503S was evaluated. Purified pegylated AvPAL_C565SC503S at approximately 12 mg/mL (0.2 mM) was pre-formulated in 10 mM Tris and 140 mM NaCl at pH 7.5 in the absence or presence of 1 or 5 mM Tyr (substrate at 5 or 25 moles per mole active site, respectively). After storing the enzyme formulations for various times at 4° C., 25° C. or 37° C., in vitro activity was measured weekly. Tyr had a minimal, non-dose dependent stabilizing effect on enzyme activity (FIG. 12).

Figure 13A:
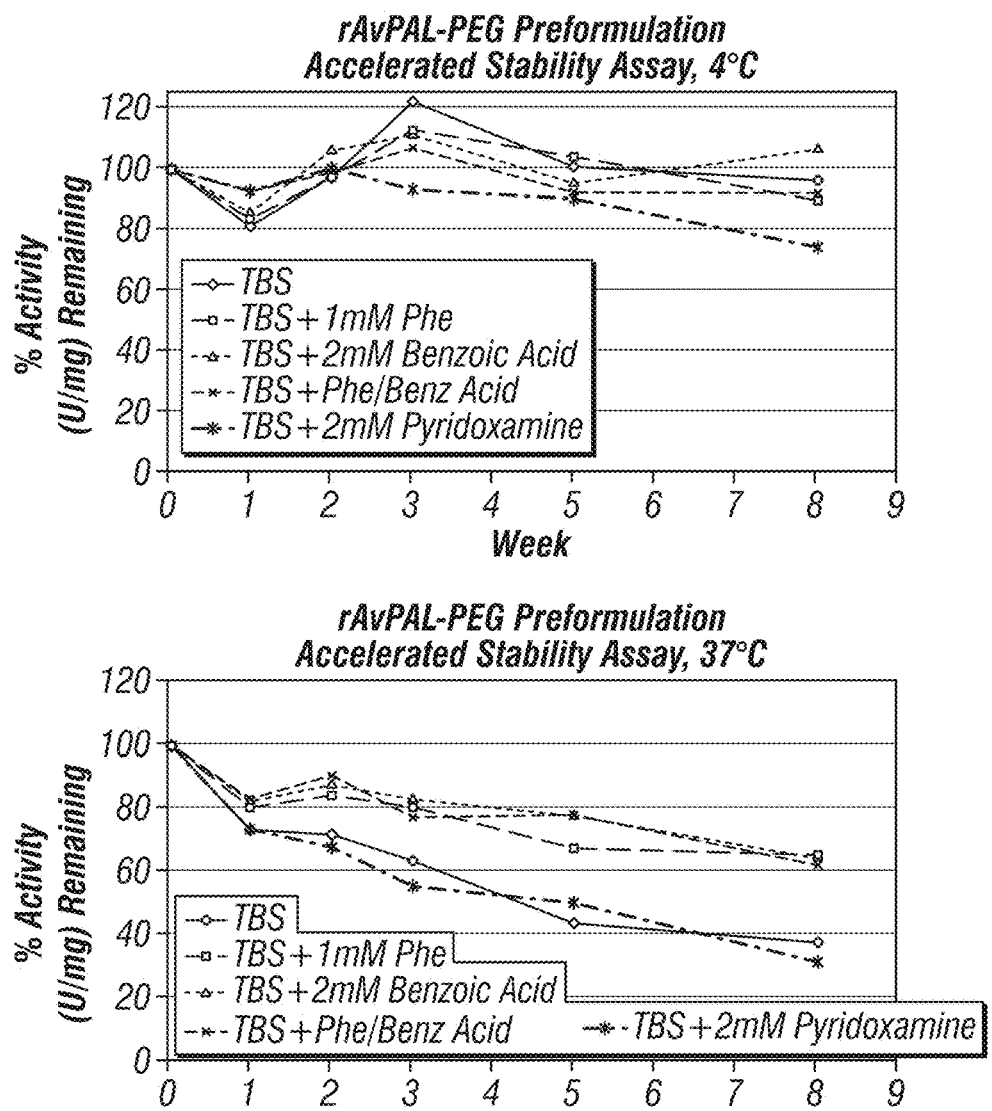
FIGS. 13A-13B show effect of Phe, benzoic acid, and pyridoxamine on the enzyme activity of a pegylated AvPAL variant. (A) Effect of Phe, benzoic acid and pyridoxamine, alone or in combination as indicated, on the enzyme activity of a pegylated AvPAL with cysteine to serine substitutions at positions 565 and 503 (AvPAL_C565SC503S) (rAV-PAL-PEG) stored for various times (weeks) at 4° C. (top panel) and at 37° C. (bottom panel). (B) The chemical structures of benzoic acid (left), phenylalanine (middle) and trans-cinnamic acid (right) are depicted.

In a sixth accelerated stability study, the effect of nucleophilic scavengers as excipient on stability of the pegylated AvPAL double cysteine mutant AvPAL_C565SC503S was evaluated. Purified pegylated AvPAL_C565SC503S at approximately 20 mg/mL (0.33 mM) was pre-formulated in 10 mM Tris and 140 mM NaCl at pH 7.5 in the absence or presence of 1 Phe (substrate at 3 moles per mole active site), 2 mM nucleophilic scavenger (either benzoic acid or pyridoxamine at 6 moles per mole active site), or both 1 mM Phe and 2 mM nucleophilic scavenger. After storing the enzyme formulations for various times at 4° C. or 37° C., in vitro activity was measured weekly. Benzoic acid, but not pyridoxamine, was effective at stabilizing enzyme activity (FIG. 13A). There was no additive effect of Phe and benzoic acid, suggesting a similar stabilizing mechanism.

Figure 13B:
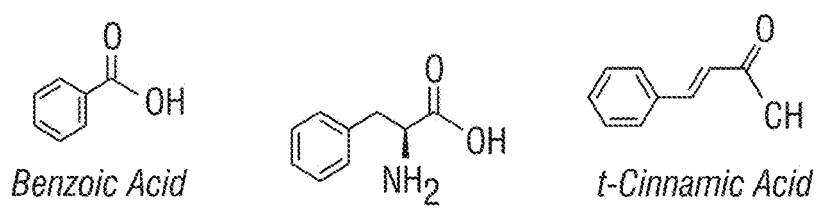

The stabilizing effects of benzoic acid and t-CA suggest that they function as structural analogs of Phe (see FIG. 13B).

The data from the six accelerated stability studies were combined in order to predict the effective shelf-life of the pegylated AvPAL double cysteine mutant AvPAL_C565SC503S in various formulations. Shelf-life was determined as follows: (1) determining the rate of activity decay ($k_{decay}$), which followed first order kinetics, for each formulation condition; (2) plotting the $\ln(k_{decay})$ v. 1/Temperature (° K); (3) determining the Ea ($\Delta G_{decay}$) required for activity decay for a given formulation condition; (4) extrapolating the $k_{decay}$ at 4° C. using the calculated Ea and the observed $k_{decay}$ at a given temperature; and (5) determining the shelf life ($T_{90}$), which is the time in which specific enzyme activity has dropped by ≥10% at 4° C.

Table 4 shows that Phe and t-CA greatly enhances the predicted shelf-life of the pegylated AvPAL double cysteine mutant AvPAL_C565SC503S.

TABLE 4

Predicted Shelf-Life $T_{90}$ (in Weeks) of Pegylated Double Cysteine Mutant AvPAL_C565SC503S with Various Excipients

| Excipient | 42° C. | 37° C. | 25° C. | 4° C.* | 4° C. (Observed) |
|---|---|---|---|---|---|
| None (TBS) | 0.67 | 0.8 | 2.1 | 12.9 | ~9-13 |
| Phe | 1.63 | 2.2 | 9.1 | 85 | >20 |
| t-CA | ND | 2.0 | 7.1 | 85.8 | >20 |

*Numbers are estimates based on data from up to 6 different experiments.

In summary, the above preformulation studies indicate that the pH optimum for the pegylated AvPAL double cysteine mutant AvPAL_C565SC503S is 7 to 7.5. The presence of anti-oxidants results in a drastic loss of enzyme activity. Both Phe and trans-cinnamic acid (t-CA) increase the stability of rAvPAL-PEG by 50% or more under accelerated conditions (25° C. and 37° C.). A 2-fold excess Phe or t-CA per rAvPAL-PEG active site is sufficient to stabilize activity and higher concentrations appear to have no additional benefit. A weaker PAL substrate, tyrosine (Tyr), does not appear to stabilize enzyme activity, whereas benzoic acid stabilizes rAvPAL-PEG activity to a similar degree as its structural analog, Phe. When combined with Phe, no additional activity stabilization is observed with benzoic acid, suggesting a common mechanism for activity stabilization.

Example 12

Lyophilized Formulations of PEGylated Forms of AvPAL Variants (Cysteine Mutants)

Studies were performed to investigate the effect of various solid (e.g., lyophilized) formulations on the activity of a PEGylated form of an AvPAL polypeptide variant (e.g., with serine substitution of the cysteine residues at positions 503 and 565).

The pegylated AvPAL double cysteine mutant AvPAL_C565SC503S was prepared as described in EXAMPLE 7.

The pegylated AvPAL double cysteine mutant AvPAL_C565SC503S was formulated as follows: (F1) 10 mg/mL AvPAL_C565SC503S, 10 mM Tris, pH 7.5; (F2) 10 mg/mL AvPAL_C565SC503S, 10 mM Tris, pH 7.5, 25 mg/mL mannitol; or (F3) 10 mg/mL AvPAL_C565SC503S, 10 mM Tris, pH 7.5, 20 mg/mL mannitol, 5 mg/mL sucrose. After formulation, the PAL enzyme activity of each was 1.7 to 1.8 U/mg. After lyophilization, the formulations were stored for up to 26 at 4° C., and then resuspended in fresh, sterile-filtered MilliQ water. The PAL enzyme activities were determined as described in EXAMPLE 11. Table 5 shows that there appeared to be no loss of activity upon lyophilization, storage or resuspension of the various AvPAL_C565SC503S formulations.

TABLE 5

Specific Activity of Pegylated Double Cysteine Mutant AvPAL_C565SC503S Upon Lyophilized Formulation (LF)

| LF | Before LF | After LF | After LF + 5 days/4° C. | After LF + 11 days/4° C. | After LF + 26 days/ 4° C. |
|---|---|---|---|---|---|
| F1 | 1.78 +/− 0.04 | 1.60 | 1.59 | 1.71 | 1.48 |
| F2 | 1.72 +/− 0.01 | 1.67 | 1.62 | 1.68 | 1.72 |
| F3 | 1.65 +/− 0.09 | 1.66 | 1.73 | 1.76 | 1.59 |

Example 13

Formulations of PEGylated AvPAL Variants

Studies were performed to investigate the effect of various excipients, e.g., stabilizers and preservatives (i.e., anti-microbial agents), on the accelerated stability of a PEGylated form of an AvPAL polypeptide variant, e.g., with serine substitutions of the cysteine residues at positions 503 and 565, AvPAL_C565SC503S) in formulations provided herein.

The pegylated AvPAL double cysteine mutant AvPAL_C565SC503S was prepared as described in EXAMPLE 7.

Accelerated stability of different formulations of pegylated AvPAL_C565SC503S was determined using an in vitro activity assay as described in EXAMPLE 11.

In a preliminary preservative compatibility study, the effect of the presence of a preservative, i.e., anti-microbial agent, on activity and stability of the pegylated AvPAL double cysteine mutant AvPAL_C565SC503S was evaluated. Purified pegylated AvPAL_C565SC503S was formulated in 10 mM Tris buffer and 135 mM NaCl at pH 7.35. Preservatives tested: benzyl alcohol (0.15%); m-cresol (0.3%); chloro-cresol (0.25%); and phenol (0.5%). After incubating the enzyme formulations in the absence of preservative or in the presence of benzyl alcohol, m-cresol, chloro-cresol or phenol for 1 hour at room temperature, an initial activity measurement was made. After storing the enzyme formulations for up to 65 days at 4° C., in vitro activity was measured. The initial enzyme activity was unaffected by the preservatives, and the enzyme was compatible with each of the preservatives tested, although a slow decay in activity was observed for m-cresol.

In a first preservative compatibility study, the effect of the presence of a preservative, i.e., anti-microbial agent, in the presence or absence of a stabilizer, i.e., L-phenylalanine (Phe) or Gly, on activity and stability of the pegylated AvPAL double cysteine mutant AvPAL_C565SC503S was evaluated. Purified pegylated AvPAL_C565SC503S was formulated in 10 mM Tris buffer and 135 mM NaCl at pH 7.35. Preservatives tested: benzyl alcohol (0.15%); m-cresol (0.3%); and phenol (0.5%). Stabilizers tested: Phe (1 mM); and Gly (1 mM). After storing the enzyme formulations in the absence of any preservative or stabilizer, or in the presence of one of the preservatives, one of the stabilizers, or various combinations of one of the preservatives and one of the stabilizers for up to 18 weeks at 4° C., 25° C. or 40° C., in vitro activity was measured. All of the preservatives reduced the initial enzyme activity in this study, and the combination of phenol and Gly was a potent enzyme inhibitor. In all cases, the enzymes formulated in the presence of preservative were less stable than those in the presence of Phe alone. In a follow-up study, similar results were obtained using 12 mg/mL (0.19 mM) enzyme formulated in 50 mM Tris buffer, 135 mM NaCl at pH 7.3.

In a second preservative compatibility study, the effect of different Tris buffer concentrations, and the effect of the presence of a preservative, i.e., anti-microbial agent, in the presence or absence of a stabilizer, i.e., Phe or Gly, on stability of the pegylated AvPAL double cysteine mutant AvPAL_C565SC503S were evaluated. Purified pegylated AvPAL_C565SC503S was formulated in 10 mM, 25 mM or 50 mM Tris buffer and 135 mM NaCl at pH 7.3. Preservative tested: benzyl alcohol (1.5%). Stabilizers tested: Phe (1 mM); and Gly (1 mM). After storing the enzyme formulations in the different Tris buffers alone, or in 50 mM Tris buffer in the presence of benzyl alcohol or Phe alone, or various combinations of benzyl alcohol, Phe and Gly, for up to 12 weeks at 4° C., 25° C. or 40° C., in vitro activity was measured. The enzyme activity was decreased as the Tris buffer concentration was increased. At the concentration tested, benzyl alcohol was incompatible with the enzyme. The enzymes in all of the formulations tested were less stable than the enzyme formulated in the presence of Phe alone.

Figure 14:
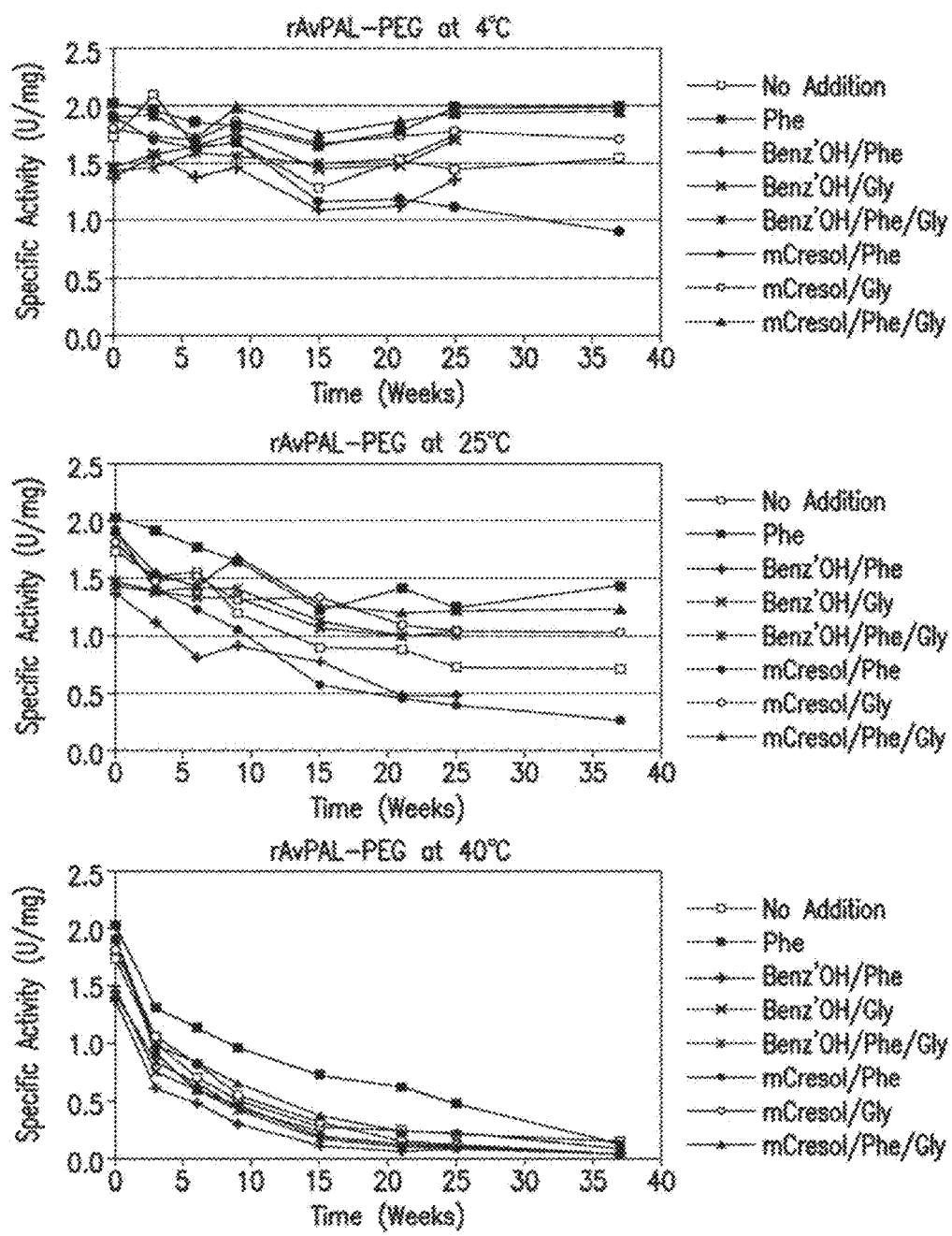
FIG. 14 Effect of preservatives benzyl alcohol (Benz'OH, 1.5%) or m-cresol (mCresol, 0.3%) and/or stabilizers L-phenylalanine (Phe, 1 mM) and/or glycine (Gly, 1 mM) as indicated on the specific activity (U/mg) of a pegylated AvPAL with cysteine to serine substitutions at positions 565 and 503 (AvPAL_C565SC503S) (rAv-PAL-PEG) stored for various times (weeks) at 4° C. (top panel), at 25° C. (middle panel) and at 40° C. (bottom panel).

In a third preservative compatibility study, the effect of the presence of various combinations of preservative, i.e., anti-microbial agent, and one or more stabilizers, i.e., Phe and Gly, on stability of the pegylated AvPAL double cysteine mutant AvPAL_C565SC503S was evaluated. Purified pegylated AvPAL_C565SC503S was formulated in 10 mM Tris buffer and 135 mM NaCl at pH 7.35. Preservatives tested: benzyl alcohol (1.5%); and m-cresol (0.3%). Stabilizers tested: Phe (1 mM); and Gly (1 mM). After storing the enzyme formulations in Phe alone, or in various combinations of Phe, Gly and either benzyl alcohol or m-cresol, for up to 37 weeks at 4° C., 25° C. or 40° C., in vitro activity was measured. The results of this study are shown in FIG. 14. As seen previously, the presence of preservative in the formulations reduced initial enzyme activity, however, the loss in enzyme activity was only transient in the enzyme formulation containing m-cresol, Phe and Gly at 4° C. and 25° C. This enzyme formulation was found to most closely approximate the stabilizing effect observed in EXAMPLE 11 for Phe alone.

In a fourth preservative comparability study, the effect of different Gly concentrations in the presence of a preservative, i.e., m-cresol, and a stabilizer, i.e., Phe, on the stability of the pegylated AvPAL double cysteine mutant AvPAL_C565SC503S was evaluated. Purified pegylated AvPAL_C565SC503S was formulated in 10 mM Tris buffer, 135 mM NaCl, 1 mM Phe and 3.2 mg/mL (0.32%) at pH 7.2, in the absence of Gly or in the presence of 1, 3, 5, 10 or 20 mM Gly. After storing the enzyme formulations for up to 12 weeks at 25° C. or 40° C., in vitro activity was measured. The results of this study are shown in FIG. 15A. The enzyme activity loss upon storage at 25° C. or 40° C., reported as normalized activity (% of enzyme activity prior to storage in the various formulations), was reduced in a dose-dependent manner by the addition of Gly. The improved stability of enzyme activity by Gly in preservative-containing formulations correlated well with maintenance of the main peak of pegylated AvPAL_C565SC503S, as determined by RP-HPLC.

In a fifth preservative comparability study, the effect of different Gly concentrations in the presence of a stabilizer, i.e., Phe, but in the absence of a preservative on the stability of the pegylated AvPAL double cysteine mutant AvPAL_C565SC503S was evaluated. Purified pegylated AvPAL_C565SC503S was formulated in 10 mM Tris buffer, 135 mM NaCl and 1 mM Phe at pH 7.2, in the presence of various concentrations of Gly, ranging from 20 to 100 mM. After storing the enzyme formulations for up to 8 weeks at 40° C., in vitro activity is measured. The results of this study are shown in FIG. 15B. The enzyme activity loss upon storage at 40° C. was reduced in a dose-dependent manner by the addition of Gly in non-preservative containing pegylated AvPAL_C565SC503S formulations.

Example 14

Effects of AvPAL Variants (Cysteine Mutants) and their PEGylated Forms in Mice

The purpose of these studies was to determine the effect of serine substitution of the cysteine residues at positions 503 and 565 in the AvPAL polypeptide on in vivo Phe levels in mice.

The pegylated forms of the AvPAL double cysteine mutant AvPAL_C565SC503S were tested for in vivo activity in homozygous ENU2 (also known as BTBR$^{enu2}$) mice basically as described in Examples 7 through 9 of prior co-pending U.S. patent application Ser. No. 11/451,999 filed on Jun. 12, 2006, which is herein incorporated by reference in its entirety. The ENU2 mouse is homozygous mutant at the PAH locus resulting in an animal with severe HPA. The high plasma Phe levels make this animal the appropriate model for evaluating the ability of PAL to reduce plasma Phe.

In the first study, the AvPAL double cysteine mutant AvPAL_C565SC503S was tested at various doses. ENU2 mice (males and females) were divided into 5 dose groups: 4 test groups (n=4) and one vehicle group (n=2). Each mouse was given 8 weekly s.c. doses of vehicle, low dose pegylated double cysteine mutant AvPAL (0.25 IU), mid dose pegylated double cysteine mutant AvPAL (1.0 IU), high dose pegylated double cysteine mutant AvPAL (4.0 IU), or pegylated wild-type AvPAL (4.0 IU). Plasma was collected pre-dose and at 48 hours post-dose (up to day 57) and analyzed for Phe levels. Serum was also collected pre-dose and at 48 hours post-dose (up to day 57) for analysis of anti-AvPAL antibody levels. Mice were also weighed once per week beginning 2 days prior to the first dose (up to day 40).

Two mice died during the study, one vehicle-treated mouse and one low dose pegylated double cysteine mutant AvPAL-treated mouse. As shown in FIG. 16, a dose-dependent reduction in Phe levels was observed in plasma 48 hours after each s.c. injection of pegylated double cysteine mutant AvPAL. At equivalent doses, there was no difference in plasma Phe levels between mice treated with pegylated wild-type AvPAL or pegylated double cysteine mutant AvPAL. As shown in FIG. 17, there was also no significant difference in body weights between mice treated with vehicle, pegylated wild-type AvPAL, or pegylated double cysteine mutant AvPAL. It is likely that no significant differences in body weights were observed because the both male and female mice were used in the study.

The anti-AvPAL antibody titers in these mice were analyzed with an indirect ELISA assay. In this assay, microtiter plates were coated with AvPAL, blocked, and then exposed to appropriately diluted sera from each mouse bleed. AvPAL, which was bound to the surface of microtiter plates, was recognized and bound by AvPAL-specific antibodies present in the serum samples. Detectably labeled goat anti-mouse IgG antibodies detected the bound anti-AvPAL antibodies. Serum samples were initially diluted 1:50, and analyzed in comparison to the "cutpoint," which came from pooled mouse serum diluted 1:50. The samples with signal lower than the cutpoint were reported as <50, or "Negative."

The rest of the samples, deemed "Positive," were further diluted in 1:3 series titering to a dilution in which the signal dropped to below the cutpoint. The highest dilution factor that gave a positive signal (i.e., higher than the cutpoint) was reported as the titer of that sample. During this titer series, a 3-fold change of titer may not reflect a significant difference of the antibody detected because the difference could be the result of a minimal change of signal at the cutpoint level.

As shown in Table 6, the anti-AvPAL antibody titers were lower in mice treated with the pegylated double cysteine mutant AvPAL as compared to mice treated with an equivalent dose (4.0 IU) of pegylated wild-type AvPAL. Although no clear dose response was observed, mice treated with the high dose (4.0 IU) of pegylated double cysteine mutant AvPAL had higher anti-AvPAL antibody titers than mice treated with the low dose (0.25 IU) of pegylated double cysteine mutant AvPAL.

TABLE 6

Anti-AvPAL IgG Titers

| Pegylated AvPAL Protein | Sample | Pre | D 8 | D 15 | D 22 | D 29 |
|---|---|---|---|---|---|---|
| AvPAL_C565SC503S (0.25 IU) | S 2 03 | <50 | 50 | <50 | 50 | 50 |
| | S 2 04 | <50 | 50 | 50 | 50 | 450 |
| | S 2 05 | <50 | <50 | <50 | <50 | <50 |
| | S 2 06 | <50 | <50 | 50 | 50 | 50 |
| AvPAL_C565SC503S (1.0 IU) | S 3 07 | <50 | <50 | <50 | <50 | <50 |
| | S 3 08 | <50 | <50 | <50 | <50 | <50 |
| | S 3 09 | <50 | <50 | <50 | <50 | 50 |
| | S 3 10 | <50 | <50 | <50 | <50 | <50 |
| AvPAL_C565SC503S (4.0 IU) | S 4 11 | <50 | <50 | <50 | 50 | 50 |
| | S 4 12 | <50 | <50 | 50 | 50 | 50 |
| | S 4 13 | 50 | 50 | 50 | 450 | 150 |
| | S 4 14 | <50 | <50 | <50 | <50 | <50 |
| WT AvPAL (4.0 IU) | S 5 15 | <50 | <50 | 150 | 150 | 450 |
| | S 5 16 | <50 | 50 | 150 | 150 | 450 |
| | S 5 17 | <50 | <50 | 150 | 4050 | 12150 |
| | S 5 18 | <50 | 50 | 150 | 450 | 150 |

| Pegylated AvPAL_Protein | Sample | Pre | D 36 | D 43 | D 50 | D 57 |
|---|---|---|---|---|---|---|
| AvPAL_C565SC503S (0.25 IU) | S 2 03 | <50 | <50 | 150 | 150 | <50 |
| | S 2 04 | <50 | >1350 | >1350 | >1350 | 4050 |
| | S 2 05 | <50 | N/A* | N/A | N/A | N/A |
| | S 2 06 | <50 | <50 | 50 | 50 | <50 |
| AvPAL_C565SC503S (1.0 IU) | S 3 07 | <50 | 50 | 150 | >1350 | 150 |
| | S 3 08 | <50 | <50 | <50 | <50 | <50 |
| | S 3 09 | <50 | 450 | >1350 | >1350 | 450 |
| | S 3 10 | <50 | <50 | 50 | 50 | <50 |
| AvPAL_C565SC503S (4.0 IU) | S 4 11 | <50 | 50 | 150 | 50 | 50 |
| | S 4 12 | <50 | 150 | 150 | 150 | 50 |
| | S 4 13 | 50 | 450 | 450 | 450 | 150 |
| | S 4 14 | <50 | 150 | 150 | 150 | 150 |
| WT AvPAL (4.0 IU) | S 5 15 | <50 | 450 | 1350 | 1350 | 150 |
| | S 5 16 | <50 | 150 | 450 | 450 | 150 |
| | S 5 17 | <50 | 4050 | 4050 | 4050 | 450 |
| | S 5 18 | <50 | 50 | 50 | 50 | <50 |

*No sample/data not available

The reduced anti-AvPAL IgG titers in mice administered 4.0 IU of pegylated double cysteine mutant AvPAL as compared to 4.0 IU pegylated wild-type AvPAL were maintained throughout the study.

In the second study, the AvPAL double cysteine mutant AvPAL_C565SC503S was tested at different pegylation ratios. Male ENU2 mice were divided into 5 dose groups: 4 test groups (n=4) and one vehicle group (n=2). Each mouse was given 8 weekly s.c. doses of vehicle, low dose pegylated double cysteine mutant AvPAL (4 IU and 1:1.6 AvPAL:PEG ratio), mid dose pegylated double cysteine mutant AvPAL (4 IU and 1:2.4 AvPAL:PEG ratio), high dose pegylated double cysteine mutant AvPAL (4 IU and 1:3 AvPAL:PEG ratio), or pegylated wild-type AvPAL (4 IU and 1:3 AvPAL:PEG ratio). Plasma was collected pre-dose and at 4 days post-dose (to day 61) and analyzed for Phe levels. Serum was also collected pre-dose at 4 days post-dose (up to day 57) for analysis of anti-AvPAL antibody levels. Mice were also weighed once per week beginning 2 days prior to the first dose (to day 40).

One vehicle-treated mouse died during the study. As shown in FIG. 18, a PEG ratio-dependent reduction in Phe levels was observed in plasma 4 days after each s.c. injection of pegylated double cysteine mutant AvPAL. At equivalent PEG ratios, there was no difference in plasma Phe levels between mice treated with pegylated wild-type AvPAL or pegylated double cysteine mutant AvPAL. As shown in FIG. 19, the body weights of mice treated with pegylated wild-type AvPAL or pegylated double cysteine mutant AvPAL were significantly higher than vehicle-treated mice.

The anti-AvPAL antibody titers in these mice were analyzed with the indirect ELISA assay described above.

As shown in Table 7, the anti-AvPAL antibody titers were lower in mice treated with the pegylated double cysteine mutant AvPAL as compared to mice treated with an equivalent dose of pegylated wild-type AvPAL having the same ratio (1:3) of AvPAL to PEG. An inverse dose response was observed between the anti-AvPAL antibody titers and the ratio of AvPAL to PEG, consistent with the expectation that pegylation of proteins, such as AvPAL, is associated with reduced immunogenicity in vivo.

The above results also show that the pegylated AvPAL variant, which has reduced protein aggregation in vitro due to cysteine to serine substitutions at both positions 503 and 565, has reduced immunogenicity compared to the pegylated wild-type AvPAL. Because pegylation itself is associated with reduced immunogenicity, it is concluded that AvPAL variants have reduced immunogenicity in vivo as compared to wild-type AvPAL.

Example 15

Toxicity/Pharmacokinetic Studies of PEGylated Forms of AvPAL Variants (Cysteine Mutants) in Cynomolgus Monkeys and Rats Toxicity/pharmacokinetic studies were performed to determine the effect of administration of a single dose of a PEGylated form of an AvPAL polypeptide variant (e.g., with serine substitution of the cysteine residues at positions 503 and 565) in Cynomolgus monkeys and in rats.

The pegylated AvPAL double cysteine mutant AvPAL_C565SC503S was prepared as described in EXAMPLE 7.

Cynomolgus Monkey Toxicity/Pharmacokinetic Study

This study used four (4) groups of monkeys, each with three males and three females. Group 1 received placebo (mL/kg); and Groups 2, 3 and 4 received a single subcutaneous injection of pegylated AvPAL double cysteine mutant AvPAL_C565SC503S in solution at 4, 12 and 60 mg/kg, respectively. Plasma samples were collected from the monkeys pre-dose, and at various times post-dose, from 3 to 504

TABLE 7

Anti-AvPAL IgG Titers

| PEGylated AvPAL Protein | Sample | Pre | D 15 | D 28 | D 43 | D 64 |
|---|---|---|---|---|---|---|
| WT AvPAL (PEG 1:3 NOF) | S 1 01 | <50 | 450 | 12150 | 4050 | >1350 |
|  | S 1 06 | <50 | 450 | 450 | 450 | 4050 |
|  | S 1 10 | <50 | 50 | 50 | 150 | 450 |
|  | S 1 17 | <50 | 150 | 450 | 450 | 1350 |
| AvPAL_C565SC503S (PEG 1:1.6) | S 2 02 | 50 | 450 | 12150 | 1350 | 1350 |
|  | S 2 07 | <50 | 1350 | 12150 | 12150 | 36450 |
|  | S 2 11 | <50 | 450 | 1350 | 12150 | 12150 |
|  | S 2 18 | 50 | 150 | 36450 | 26.57M | >36450 |
| AvPAL_C565SC503S (PEG 1:2.4) | S 3 03 | <50 | 50 | 150 | 450 | 4050 |
|  | S 3 08 | <50 | 50 | 50 | 50 | 450 |
|  | S 3 12 | <50 | 50 | 150 | 450 | 4050 |
|  | S 3 13 | <50 | 50 | 450 | 1350 | 4050 |
| AvPAL_C565SC503S (PEG 1:3) | S 4 04 | <50 | 50 | 50 | 450 | 450 |
|  | S 4 09 | 50 | 50 | 50 | 150 | 450 |
|  | S 4 14 | <50 | <50 | 50 | 450 | 1350 |
|  | S 4 16 | <50 | <50 | 150 | 50 | 450 |
| Vehicle | S 5 05 | <50 | <50 | <50 | <50 | N/A* |
|  | S 5 15 | <50 | <50 | <50 | <50 | <50 |

*N/A: no serum sample for this timepoint

The above results show that the pegylated double cysteine mutant AvPAL AvPAL_C565SC503S has in vivo PAL enzyme activity that is comparable to the pegylated wild-type AvPAL. Because unpegylated wild-type AvPAL had no detectable in vivo PAL enzyme activity (see Example 8 in U.S. patent application Ser. No. 11/451,999 filed on Jun. 12, 2006), it is concluded that AvPAL variants, including the pegylated double cysteine mutant AvPAL, AvPAL_C565SC503S, and the pegylated wild-type AvPAL have greater phenylalanine converting activity than the wild-type AvPAL.

hours. The 60 mg/kg dose was found to be toxic to the monkeys, so the Group 4 portion of this study was terminated.

FIG. 20A shows the concentration of pegylated AvPAL double cysteine mutant AvPAL_C565SC503S in the plasma at various times after a single subcutaneous injection at 4 and 12 mg/kg. The data shows monophasic elimination of the pegylated AvPAL double cysteine mutant AvPAL_C565SC503S. A single compartment model with $1^{st}$ order absorption appears to describe the plasma profile of the pegylated AvPAL double cysteine mutant AvPAL_C565SC503S after a single subcutaneous injection.

FIG. 20B shows the concentrations of Phe and pegylated AvPAL double cysteine mutant AvPAL_C565SC503S in the plasma at various times after a single subcutaneous injection at 4 mg/kg. At this dose, the plasma Phe concentration was reduced to below the limit of quantitation in the GC/MS assay within 24 hours, and the drop in plasma Phe was sustained over 10 days.

Rat Toxicity/Pharmacokinetic Study

This study used eight (8) groups of rats, with 3 males and 3 females in the placebo groups, and 6 males and 6 females in the test groups. Groups 1 and 5 received single intravenous and subcutaneous injections of placebo. Groups 2, 3 and 4 received single intravenous injections of pegylated AvPAL double cysteine mutant AvPAL_C565SC503S at 1, 5 and 25 mg/kg, respectively. Groups 6, 7 and 8 received single subcutaneous injections of pegylated AvPAL double cysteine mutant AvPAL_C565SC503S at 10, 25 and 250 mg/kg, respectively. Blood samples were collected from the rats pre-dose, and at various times post-dose, from 1 to 360 hours. At each collection time, blood was collected from 3 rats in each group. No toxicity was observed in the rats in this study.

FIG. 21A shows the concentration of pegylated AvPAL double cysteine mutant AvPAL_C565SC503S in the plasma at various times after a single intravenous injection at 1, 5 and 25 mg/kg. The data shows monophasic elimination of the pegylated AvPAL double cysteine mutant AvPAL_C565SC503S from the plasma after a single intravenous injection.

FIG. 21B shows the concentration of pegylated AvPAL double cysteine mutant AvPAL_C565SC503S in the plasma at various times after a single subcutaneous injection at 10, 25 and 250 mg/kg. A single compartment model with first order absorption appears to describe the plasma profile of the pegylated AvPAL double cysteine mutant AvPAL_C565SC503S after a single subcutaneous injection.

Table 8 shows pharmacokinetic parameters of the pegylated AvPAL double cysteine mutant AvPAL_C565SC503S after a single intravenous or subcutaneous injection.

TABLE 8

Pharmacokinetic Parameters of Pegylated Double Cysteine Mutant AvPAL_C565SC503S After a Single Intravenous or Subcutaneous Dose

| Route | Dose (mg/kg) | $AUC_{0-\infty}$ (ng-hr/mL) | $C_{max}$ (ng/mL) | $T_{max}$ (hr) | $t_{1/2}$* (hr) | F (%) |
|---|---|---|---|---|---|---|
| Intravenous | 1 | 657131 | 12600 | 4.5 | 27.9 | — |
| | 5 | 3579327 | 87667 | 2 | 39.1 | — |
| | 25 | 10860907 | 202238 | 9.0 | 30.4 | — |
| Subcutaneous | 10 | 1304016 | 16674 | 18.0 | 46.9 | 19.7 |
| | 25 | 2290754 | 29260 | 42.0 | 21.0 | 12.5# |
| | 250 | 37254683 | 225200 | 72.0 | 62.8 | 34.0 |

*For the subcutaneous route of administration, terminal $t_{1/2}$ is longer than intravenous; this may be due to a slower rate of absorption from subcutaneous tissues than the rate of elimination (so that the $t_{1/2}$ observed is actually absorption).
Bioavailability using intravenous AUC data at 25 mg/kg is 21.5%.

There appeared to be no gender difference in this pharmacokinetic study. The $AUC_{inf}$ and $C_{max}$ were roughly proportional with dose for both the intravenous and subcutaneous routes of administration.

Multiple Dose Toxicity Studies in Rats and Cynomolgus Monkeys

The safety of pegylated AvPAL double cysteine mutant AvPAL_C565SC503S was evaluated in repeat-dose toxicity studies in rats and Cynomolgus monkeys.

Rats administered up to 25 mg/kg pegylated AvPAL double cysteine mutant AvPAL_C565SC503S twice weekly, subcutaneously over 28 days exhibited no toxicity.

Cynomolgus monkeys administered up to doses of 1 mg/kg pegylated AvPAL double cysteine mutant AvPAL_C565SC503S twice weekly, subcutaneously over 28 days exhibited no significant toxicity. A dose dependent decrease in plasma Phe levels was observed after the first dose; however, after the seventh dose, plasma Phe levels returned to baseline in all dose groups, indicating a possible antibody response toward the administered enzyme. Minimal anti-AvPAL_C565SC503S IgG titers were observed in most 1 mg/kg treated animals at day 28. No IgM titers were observed in any animal in the study at day 28.

Example 16

Exemplary Prokaryotic PAL Formulations

The following example provides guidance on the parameters to be used to formulate compositions comprising prokaryotic PAL or biologically active fragments, mutant, variants or analogs thereof, which are useful for treatment of diseases and disorders characterized by elevated levels of phenylalanine, e.g., HPA, including PKU, and other disorders, including cancer. Parameters to be used to formulate prokaryotic PAL compositions include, but are not limited to, buffering agents to maintain pH, isotonicity-adjusting agents, absence or presence of stabilizers, and absence or presence of other excipients, vehicles, diluents, and the like.

In EXAMPLE 11, the pegylated AvPAL double cysteine mutant AvPAL_C565SC503S was formulated at a concentration of about 12-20 mg/mL (about 0.2-0.33 mM). One prokaryotic PAL variant is formulated at a concentration ranging from about 1 to 50 mg/mL (about 0.016 to 0.8 mM), such as from about 5 to 20 mg/mL (about 0.08 to 0.33 mM), or from about 5 to 15 mg/mL (about 0.08 to 0.25 mM). One exemplary formulation of the prokaryotic PAL compositions provided herein has a PAL enzyme concentration of about 10+/−5 mg/mL (about 0.16+/−0.08 mM).

In EXAMPLE 11, the pegylated AvPAL double cysteine mutant AvPAL_C565SC503S was formulated in 10 mM Tris-HCl, 140 mM NaCl at pH 7.0, 7.5 and 8.0. One exemplary buffering agent is Tris-HCl, or its equivalent, with a concentration ranging from 5 to 50 mM, such as from 5 to 20 mM, or from 5 to 15 mM. An exemplary formulation of the prokaryotic PAL compositions provided herein has a Tris-HCl buffer concentration of about 10+/−5 mM.

One exemplary pH of the pharmaceutical composition is about pH 6.0-8.5, such as about pH 7.0-8.0, or about pH 7.0-7.6. An exemplary formulation of the prokaryotic PAL compositions provided herein has a pH of about pH 7.3+/−0.3.

One exemplary isotonicity-adjusting agent is NaCl, or its equivalent, with a concentration ranging from about 100 to 200 mM, such as from about 130 to 170 mM, or from about 130 to 150 mM. An exemplary formulation of the prokaryotic PAL compositions provided herein has a NaCl concentration of about 140+/−10 mM.

As shown in EXAMPLE 11, the pegylated AvPAL double cysteine mutant AvPAL_C565SC503S was stabilized in the presence of Phe, and certain of its structural analogs, including, for example, t-CA and benzoic acid; Tyr had a minimal stabilizing effect on the PAL enzyme. One exemplary stabilizer is Phe, or structural analog thereof, with a range for the stabilizer from about 0.1 to 20 moles of stabilizer per mole active site of prokaryotic PAL, such as from about 0.5 to 10 moles of stabilizer per mole active site of prokaryotic PAL, or from about 1 to 10 moles of stabilizer per mole active site of prokaryotic PAL. An exemplary formulation of the prokaryotic PAL compositions provided herein has a stabilizer concentration of about 5+/−4 moles of stabilizer per mole active site of prokaryotic PAL.

The pegylated AvPAL double cysteine mutant AvPAL_C565SC503S was not significantly stabilized at pH<7 or pH>7.6, or in the presence of EDTA, aminoguanidine or Tween 80; the anti-oxidants ascorbic acid and methionine destabilized the PAL enzyme (EXAMPLE 11 and data not shown). However, the compositions provided herein can include one or more of these ingredients.

Prokaryotic PAL compositions can be made as liquid formulations, but can also be prepared as solid (e.g., lyophilized) formulations. In such case, excipients, e.g., bulking agents, such as mannitol and/or sucrose, can be added. In EXAMPLE 12, the pegylated AvPAL double cysteine mutant AvPAL_C565SC503S was formulated and lyophilized in 10 mM Tris-HCl, 140 mM NaCl at pH 7.5 in the absence of mannitol or sucrose, in the presence of 25 mg/mL mannitol, or in the presence of 20 mg/mL mannitol plus 5 mg/mL sucrose. One exemplary lyophilized formulation comprises mannitol at a concentration from about 1 to 5% (w/v) or 10 to 50 mg/mL, such as from about 2 to 4%, or from about 2 to 3%. Another lyophilized formulation comprises mannitol and sucrose, with a concentration of mannitol from about 1 to 5% (w/v) (or 10 to 50 mg/mL), such as from about 1 to 3%, or from about 1.5 to 2.5%; and a concentration of sucrose from about 0.1 to 2% (w/v) (or 0.1 to 2 mg/mL), such as from about 0.2% to 1%, or from about 0.3% to 0.7%. Yet another lyophilized formulation of the prokaryotic PAL compositions has a mannitol concentration of about 2.5+/−0.5% mannitol or 2.0+/−0.5% mannitol plus 0.5+/−0.2% sucrose.

Accordingly, an exemplary formulation of the prokaryotic PAL compositions provided herein is shown in Table 9.

TABLE 9

Exemplary Formulations of Prokaryotic PAL Variants

| Ingredient Class | Ingredient Type | Concentration Range |
| --- | --- | --- |
| Prokaryotic PAL Variant | Pegylated AvPAL_C565SC503S | 10 +/− 5 mg/mL (0.16 +/− 0.08 mM) |
| Buffering Agent | Tris-HCl | 10 mM +/− 5 mM, and pH 7.3 +/− 0.3 |
| Isotonicity-Adjusting Agent | NaCl | 140 mM +/− 10 mM |
| Stabilizer | Phe, t-CA, or Benzoic Acid | 5 +/− 4 moles of stabilizer per mole PAL active site |
| Other Excipients, Bulking Agents* | Mannitol +/− Sucrose | 2.5 +/− 0.5% (w/v) mannitol; 2.0 +/− 0.5% (w/v) mannitol + 0.5 +/− 0.2% (w/v) sucrose |

*For lyophilized prokaryotic PAL formulations

Example 17

Exemplary Formulations of PEGylated AvPAL Variants

The following example provides exemplary formulations of compositions comprising a pegylated AvPAL variant, i.e., double cysteine mutant AvPAL_C565SC503S, which is useful for treatment of diseases and disorders characterized by elevated levels of phenylalanine, e.g., HPA, including PKU, and other disorders, including cancer. Parameters that can be used to formulate prokaryotic PAL compositions include, but are not limited to, buffering agents to maintain pH, isotonicity-adjusting agents, absence or presence of stabilizers, and absence or presence of other excipients, vehicles, diluents, and the like, e.g., a preservative or anti-microbial agent. It is understood that these formulations are applicable to other pegylated AvPAL variants, such as other AvPAL cysteine mutants as described herein.

In EXAMPLE 13, the pegylated AvPAL double cysteine mutant AvPAL_C565SC503S was formulated at a concentration of about 8-20 mg/mL (about 0.13-0.33 mM). One pegylated AvPAL variant is formulated at a concentration ranging from about 1 to 50 mg/mL (about 0.016 to 0.8 mM), such as from about 5 to 20 mg/mL (about 0.08 to 0.33 mM), or from about 5 to 15 mg/mL (about 0.08 to 0.25 mM). A formulation of the pegylated AvPAL variant compositions provided herein has an enzyme concentration of about 10+/−5 mg/mL (about 0.16+/−0.08 mM).

In EXAMPLE 13, the pegylated AvPAL double cysteine mutant AvPAL_C565SC503S was formulated in 10 mM Tris-HCl, 135 mM NaCl at pH 7.3. One exemplary buffering agent for formulations provided herein is Tris-HCl, or its equivalent, with a concentration ranging from 5 to 50 mM, such as from 5 to 20 mM, or from 5 to 15 mM. One formulation of the AvPAL variant compositions provided herein has a Tris-HCl buffer concentration of about 10+/−5 mM.

An exemplary pH of the pharmaceutical composition is about pH 6.0-8.0, such as about pH 6.5-7.5, onrabout pH 7.0-7.6. One formulation of the AvPAL variant compositions provided herein has a pH of about pH 7.3+/−0.3.

An exemplary isotonicity-adjusting agent is NaCl, or its equivalent, with a concentration ranging from about 100 to 200 mM, such as from about 120 to 170 mM, or from about 120 to 150 mM. One formulation of the AvPAL variant compositions provided herein has a NaCl concentration of about 135+/−15 mM.

As shown in EXAMPLE 13, the pegylated AvPAL double cysteine mutant AvPAL_C565SC503S was stabilized in the presence of a combination of a preservative or anti-microbial agent, i.e., m-cresol, and two stabilizers, i.e., Phe and Gly. An exemplary preservative is m-cresol or structural analog thereof, with a range for the preservative from about 0.1% to 1% (w/v), such as from about 0.1% to 0.5% (w/v), or from about 0.3% to 0.5% (w/v). One formulation of the AvPAL variant compositions has a preservative concentration of about 0.4%+/−0.1% (w/v). Exemplary stabilizers are Phe or structural analog thereof and/or Gly or structural analog thereof, with a range of Phe or structural analog from about 0.1 to 10 mM, such as from about 0.5 to 5 mM, or from about 0.5 to 1.5 mM, and with a range of Gly or structural analog from about 0.1 to 100 mM, such as from about 1.0 to 100 mM, from about 1.0 to 20 mM, or from about 20 to 100 mM. One formulation of the AvPAL variant compositions provided herein has a concentration for Phe of about 1.0+/−0.5 mM and Gly of about 50.5+/−49.5 mM. Another formulation of the AvPAL variant compositions provided herein has a concentration for Phe of about 1.0+/−0.5 mM and Gly of about 10.5+/−9.5 mM. Another formulation of the AvPAL variant compositions provided herein has a concentration for Phe of about 1.0+/−0.5 mM and Gly of about 60+/−40 mM.

Accordingly, one exemplary formulation of the pegylated AvPAL variant compositions provided herein is shown in Table 10. It should be understood that the presence of the preservative, i.e., m-cresol, is optional in this exemplary formulation.

TABLE 10

Exemplary Formulations of Pegylated AvPAL Cysteine Mutants

| Ingredient Class | Ingredient Type | Concentration Range |
|---|---|---|
| AvPAL Variant | Pegylated AvPAL_C565SC503S | 10 +/− 5 mg/mL (0.16 +/− 0.08 mM) |
| Buffering Agent | Tris-HCl | 10 mM +/− 5 mM, and pH 7.3 +/− 0.3 |
| Isotonicity-Adjusting Agent | NaCl | 135 mM +/− 15 mM |
| Preservative | m-Cresol | 0.4% +/− 0.1% (w/v) |
| Stabilizer | Phe | 1 mM +/− 0.5 mM |
| Stabilizer | Glycine | 50.5 mM +/− 49.5 mM |

Example 18

Production of AvPAL Variants with Reduced Aggregation

Control of aggregation is a concern in the production and formulation of protein-based therapeutics, in particular when the protein itself is immunogenic. A production process was developed that would allow for large scale manufacturing of a pegylated AvPAL polypeptide variant (e.g., with serine substitution of the cysteine residues at positions 503 and 565) with minimal aggregation. As used herein, "minimal aggregation" means that the ratio of aggregated (i.e., form eluting from SE-HPLC prior to the tetrameric form) AvPAL variant to non-aggregated (i.e., tetrameric form) AvPAL variant is less than 1%, such as less than 0.5%, less than 0.2%, or less than 0.1%.

During development of a production process for large scale manufacturing of a pegylated AvPAL polypeptide variant, it was found that the enzyme was susceptible to precipitation and aggregation. Precipitates can be removed by filtration, although they can readily re-form. Appropriate use of filters and certain non-ionic detergents can solve the problem of precipitation. Two types of soluble aggregates were identified: very large 100 nm aggregates that are detected by dynamic light scattering and can be removed by filtration; and smaller aggregates that are detected by SE-HPLC and cannot be removed by filtration. Appropriate steps were taken to reduce or minimize the presence of precipitates and aggregates in the production process.

A flow chart depicting an exemplary production process for the large scale manufacturing of the AvPAL double cysteine mutant AvPAL_C565SC503S is shown in FIG. 22. The leftward pointing arrows indicate the production steps in which a reduction in aggregation of the AvPAL double cysteine mutant AvPAL_C565SC503S was achieved, including, from top to bottom: (a) order of chromatography steps during enzyme purification; (b) addition of cryoprotectant prior to freeze-thaw of the purified enzyme; (c) use of various excipients and filtration steps; and (d) choice of buffer conditions and use of excipients during pre-PEGylation processing of purified enzyme. However, it will be appreciated that any one or more of these production steps can be used alone or in any combination to achieve an AvPAL variant or a pegylated AvPAL variant having decreased aggregation (e.g., minimal aggregation) as compared to an AvPAL variant or pegylated AvPAL prepared by a method without the one or more production steps. Each of the steps in an exemplary production process for the AvPAL double cysteine mutant AvPAL_C565SC503S is summarized below.

Fermentation.

A seed vial of BLR(DE3)/pLysS (Novagen) cells expressing AvPAL variant polypeptide AvPAL_C565SC503S (see EXAMPLE 7) was thawed, transferred into a 2.8 L flask containing approximately 500 mL culture media, and incubated at 37° C. with agitation until a cell density of 2 to 4 $OD_{600}$ was reached. The seed flask was transferred into a first bioreactor (4 L fermenter), and fermentation proceeded at 37° C. until the culture reached a cell density of 10 to 20 $OD_{600}$. The first bioreactor (4 L fermentation) culture was transferred into a second bioreactor (100 L fermenter), and fermentation proceeded at 37° C. until the culture reached a cell density of at least 200 $OD_{600}$. The culture broth was cooled to 15° C., and the cells were separated from the culture medium by centrifugation using a CEPA Z61 centrifuge or a Westfalia CSC-6 continuous disc stack centrifuge. The cell paste was frozen at −80° C. The above process may be scaled up for a third bioreactor (e.g., 500 L or larger production fermenter).

Cell Lysis.

The frozen cell paste was thawed and resuspended in a buffer of room temperature 20 mM Tris-HCl, 100 mM NaCl, pH 8.0 to generate a cell slurry with a density of about 120 to 140 $OD_{600}$. The cells were lysed by homogenization by two passes through a Niro NS30006 homogenizer at 700-800 Bar in which the temperature was controlled to below 30° C. The temperature of the lysate was monitored to ensure that it remained below 50° C. during the homogenization process.

Heat Step.

After homogenization, the temperature of the cell lysate was adjusted to 20° C., and the pH was adjusted to about 8.0 by addition of 1N NaOH. The cell lysate was gently heated to 65° C., maintained at 65° C. for 30 to 120 minutes, and then cooled to 15° C.

Centrifugation and Filtration.

The heated cell lysate was clarified by centrifugation using a CEPA Z61 centrifuge or a Westfalia CSC-6 continuous disc stack centrifuge. The supernatant containing soluble AvPAL variant polypeptide was retained, and the insoluble lysate pellet was discarded. The clarified heat-treated lysate from the Westfalia centrifuge had suspended particles that fouled downstream filters. After testing a variety of filters, a filtration scheme suitable for processing 250 L clarified heat-treated lysate was identified: 150 LMH flow rate of the clarified heat-treated lysate in series through (a) 1.3 m² Cuno R55SP Zetacarbon depth filter, 0.5-1.0 μm, (b) 7.5 m² Pall KS50P single layer cellulose based depth filter, 0.4-0.8 μm, (c) 7.5 m² Pall EKMP single layer cellulose based depth filter, 0.2-0.5 μm, and (d) 6.6 m² Pall EDF double layer PES/PVDF sterilizing grade filter, 0.2 μm.

AIEX Chromatography and HIC Chromatography.

The AvPAL variant polypeptide AvPAL_C565SC503S was purified from the clarified heat-treated lysate by sequential passage over a hydrophobic interaction (HIC) column and an anion exchange (AIEX) column as described in EXAMPLE 2, except that the AIEX column resin was changed from MacroPrep High Q to Toyopearl Giga Cap Q 650M (TPGQ, Tosoh Biosciences), and the column order was reversed so that the TPGQ AIEX column was first and the Toyopearl Butyl 650M (TPB, Tosoh Biosciences) HIC column was second. It should be appreciated that other AIEX and HIC column resins can be used, and that the HIC column can be replaced by size exclusion chromatography.

The clarified heat-treated lysate was diluted 2× in 25 mM Tris-HCl, pH 7.8, and loaded onto a TPGQ AIEX column equilibrated in 25 mM Tris-HCl, pH 7.8. The column was washed with 25 mM Tris-HCl, 130 mM NaCl, pH 7.8, and the AvPAL_C565SC503S was eluted using a gradient of 130 to 1000 mM NaCl in 25 mM Tris-HCl, pH 7.8. Fractions containing AvPAL_C565SC503S were pooled and diluted 2× with 25 mM Tris-HCl, 1.2 M $(NH_4)_2SO_4$, pH 6.5, and loaded onto a TPB HIC column equilibrated in 25 mM Tris-HCl, 0.64 M $(NH_4)_2SO_4$, pH 6.5. The column was washed with 25 mM Tris-HCl, 0.58 M $(NH_4)_2SO_4$, pH 6.5, and the AvPAL_C565SC503S was eluted using a gradient of 0.58 to 0 M $(NH_4)_2SO_4$ in 25 mM Tris-HCl, pH 6.5. Fractions containing AvPAL_C565SC503S were pooled.

At this stage of the production process, purified AvPAL_C565SC503S showed a high level of purity as determined by anti-*E. coli* host cell protein (ECP) ELISA, by SDS-PAGE followed by Coomassie staining, silver staining, anti-AvPAL Western blotting and anti-ECP Western blotting, and by SE-HPLC. Reversing the column order so that the HIC column followed the AIEX column resulted in decreased aggregation of the purified AvPAL_C565SC503S as determined by SE-HPLC. In three runs, 0.07%+/−0.03% aggregates (ratio in percent of aggregated to non-aggregated (i.e., tetrameric) enzyme) were detected in the purified AvPAL_C565SC503S after the HIC column, compared to 7.58%+/−1.68% after the AIEX column.

AvPAL Bulk (Store Frozen).

After elution from the HIC column, the purified AvPAL_C565SC503S is typically stored frozen. For large scale manufacturing, the bulk purified AvPAL_C565SC503S is frozen in liquid nitrogen using discrete temperature steps, and then stored at about −30° C. or at a lower temperature, e.g., at about −70° C. or about −80° C. A controlled freeze resulted in reduced enzyme aggregation compared to uncontrolled freeze. Addition of sugars or polyols, including 5%, 10% or 15% glycerol, 10% sucrose or 10% sorbitol, to the bulk purified AvPAL_C565SC503S prior to freezing resulted in reduced aggregation upon thawing. It should be appreciated that addition of one or more sugars or polyols, such as, for example and not for limitation, glycerol, sucrose, trehalose, glycerin, sorbitol, mannitol, and the like, at various concentrations ranging from 5% to 20% (v/v for liquids and w/v for powders), to the bulk purified AvPAL_C565SC503S prior to freezing results in reduced aggregation upon thawing.

Small scale studies were performed to determine whether bulk purified AvPAL_C565SC503S could be concentrated prior to freezing without adversely affecting the integrity or specific activity of the enzyme, or the amount of aggregation.

A preparation of purified AvPAL_C565SC503S in 25 mM Tris-HCl, ~0.24 M $(NH_4)_2SO_4$, pH 6.5 was adjusted to a final concentration of 10% (v/v) glycerol, aliquoted into bottles, frozen on dry ice and stored at −80° C. Frozen bulk AvPAL_C565SC503S was thawed in a 30° C. water bath, filtered though a 0.2 μm PES vacuum filter and concentrated by ultrafiltration using a Hydrosart 30 kDa molecular weight cut-off membrane (Sartorius). AvPAL_C565SC503S was concentrated by ultrafiltration. Aliquots were removed when the enzyme was 2×, 4×, 8× and 16× concentrated, resulting in enzyme concentrations from 2.5 mg/mL up to about 35 mg/mL. The samples removed for analysis were filtered through a 0.2 μm Acrodisk Supor syringe filter, frozen to −80° C., stored for three days, and thawed in a 30° C. water bath. As judged by protein recovery, specific activity recovery, protein integrity and level of aggregation following freeze-thaw, concentration of bulk AvPAL_C565SC503S did not result in any deleterious effect on the enzyme.

Bulk AvPAL (Thawed).

For large scale manufacturing, frozen bulk purified AvPAL_C565SC503S is thawed in discrete controlled steps. A controlled thaw resulted in reduced enzyme aggregation compared to uncontrolled thaw.

Ultrafiltration/Diafiltration.

A series of filtration steps were implemented in order to concentrate the bulk purified AvPAL_C565SC503S with minimal aggregation prior to pegylation. The thawed bulk purified AvPAL_C565SC503S was filtered through a glass fiber filter followed by a nylon filter to remove large aggregates. The filtered bulk purified AvPAL_C565SC503S was subjected to ultrafiltration/diafiltration to concentrate the enzyme to about 75 mg/mL. The original diafiltration buffer was 200 mM potassium phosphate (KPi), pH 8.5, but was changed to 50 mM potassium phosphate (KPi), 10 mM trans-cinnamic acid (t-CA), 5% glycerol, pH 8.5. It was found that reduction in KPi concentration and addition of t-CA and glycerol resulted in reduced protein aggregation as detected by SE-HPLC. Other buffers, such as carbonate and borate, and other phosphate salts, such as sodium phosphate (NaPi), can be used, so long as the buffer concentration is kept as low as is compatible with the subsequent pegylation process. After ultrafiltration/diafiltration, the bulk purified AvPAL_C565SC503S was re-filtered through glass fiber filter followed by a nylon filter.

The ultrafiltered/diafiltered AvPAL_C565SC503S was adjusted to about 60 mg/mL in 200 mM KPi, 8 mM t-CA, 4% glycerol, 0.02% polysorbate 80 (PS80), pH 8, and then filtered through a PVDF filter. It was found that addition of PS80 prevented formation of protein precipitates. Other non-ionic detergents can be used to prevent precipitation, such as polysorbate 20 (PS20), Brij 35, and the like.

Add NHS-PEG.

Purified AvPAL_C565SC503S was pegylated basically as described in EXAMPLE 6, except that the concentrations were adjusted as a consequence of increasing the enzyme concentration above. The final pegylation reaction mixture was 15 mg/mL AvPAL_C565SC503S, 13.1 mM 20 kDa NETS-activated PEG (NOF), 1.5 mM t-CA and 0.005% PS80. After 3 hours at ambient temperature, the reaction mixture was diluted to an enzyme concentration of about 2.3 mg/mL, and quenched by addition of a Tris/NaCl buffer.

Free PEG Removal and Final Formulation.

Free PEG was removed from the pegylated AvPAL_C565SC503S by ultrafiltration/diafiltration basically as described in EXAMPLE 6 and then formulated basically as described in EXAMPLES 11 and 13.

Pegylated AvPAL_C565SC503S Formulated Bulk Drug Substance (PEG-PAL FBDS) (Store Frozen).

The formulated pegylated AvPAL_C565SC503S was frozen and stored at −70° C. The final formulated drug product has an enzyme concentration of 10 mg/mL with minimal aggregation.

Example 19

Clinical Evaluation with Prokaryotic PAL Compositions

The following example provides guidance on the parameters to be used for the clinical evaluation of compositions comprising prokaryotic PAL or biologically active variants, mutants, and fragments thereof ("prokaryotic PAL") in the therapeutic methods of provided herein. As discussed elsewhere, prokaryotic PAL can be used in the treatment of HPA, mild PKU and classic PKU. Clinical trials will be conducted which will provide an assessment of oral or subcutaneous doses of prokaryotic PAL for safety, pharmacokinetics, and initial response of both surrogate and defined clinical endpoints. The trial will be conducted for a minimum, but not necessarily limited to, 24 weeks to collect sufficient safety information for 100 evaluable patients. The initial dose for the trials will vary from about 0.001 to about 1.0 mg/kg/week. In the event that this dose does not produce a reduction in excess plasma Phe levels in a patient, or produce a significant direct clinical benefit measured as an ability to increase daily oral Phe intake without increases in plasma Phe levels, the dose can be increased as necessary and maintained for an additional minimal period of, but necessarily limited to, 24 weeks to establish safety and to evaluate further efficacy.

Measurements of safety will include adverse events, allergic reactions, complete clinical chemistry panel (kidney and liver function), urinalysis, and CBC with differential. In addition, other parameters including the reduction in levels of blood Phe levels, neuropsychological and cognitive testing, and global assessments also will be monitored. The present example also contemplates the determination of pharmacokinetic parameters of the drug in the circulation, and general distribution and half-life of prokaryotic PAL in blood. It is anticipated that these measures will help relate dose to clinical response.

Methods

Patients who have elevated levels of plasma Phe will undergo a baseline a medical history and physical exam, neuropsychological and cognitive testing, a standard set of clinical laboratory tests (CBC, Panel 20, CH50, UA), levels of urinary pterins, dihydropteridine reductase (DHPR) levels, and a fasting blood (plasma) panel of serum amino acids. The patient will be followed closely with weekly visits to the clinic. Patients will return to the clinic for a complete evaluation one week after completing the treatment period. Should dose escalation be required, the patients will follow the same schedule outlined above. Safety will be monitored throughout the trial.

Diagnosis and Inclusion/Exclusion Criteria

The patient can be male or female, with a documented diagnosis of HPA or mild PKU confirmed by genetic testing and evidence of elevated Phe levels in blood. The study will include HPA or PKU patients who do not accurately follow dietary control. Female patients of childbearing potential must have a negative pregnancy test (urine β-hCG) just prior to each dosing and must be advised to use a medically accepted method of contraception throughout the study. A patient will be excluded from this study if the patient is pregnant or lactating; has received an investigational drug within 30 days prior to study enrollment; or has a medical condition, serious intercurrent illness, or other extenuating circumstance that can significantly decrease study compliance.

Dietary Intervention

Following the initial randomization and two-week treatment period, all study participants will undergo dietary counseling and will follow a standard diet and/or a standard Phe-restricted diet complemented with Phe-specific medical foods for a total of four to six weeks. Diets will be managed at home and dietary intake will be recorded in daily logs. Analyses of the intakes of nutrients and medical foods and the percent of Recommended Dietary Intakes (RDI) will be compared among the treatment groups.

Prokaryotic PAL Safety

Prokaryotic PAL therapy will be determined to be safe if no significant acute or chronic drug reactions occur during the course of the study. The longer-term administration of the drug will be determined to be safe if no significant abnormalities are observed in the clinical examinations, clinical labs, or other appropriate studies.

Example 20

Clinical Evaluation of a Pegylated AvPAL Variant

The pegylated double cysteine mutant AvPAL, AvPAL_C565SC503S will be clinically evaluated in humans. The objective of the clinical evaluation is to determine the safety, tolerability, pharmacokinetics (PK), and efficacy in PKU patients. Blood Phe levels will serve as a clinical endpoint.

Phase 1

Phase 1 is an open label, single dose escalation study in 35 PKU patients of ages between 16 and 50 years. The primary objective is to assess the safety and tolerability of pegylated double cysteine mutant AvPAL, AvPAL_C565SC503S, and the secondary objectives are to evaluate the pegylated enzyme's PK and Phe reduction. Seven cohorts of 5 subjects are administered sequentially with increasing doses of 0.001, 0.003, 0.01, 0.03, 0.1, 0.3 and 1 mg/kg pegylated AvPAL_C565SC503S. The subjects in each cohort receive a single dose, and then are followed up for a total of 6 weeks. The inclusion criteria is that the blood Phe level at screening and the average blood Phe level over the past 3 years is ≥600 μM.

Phase 2

The Phase 2 study is divided into two parts with no interruption:
Part 1—16 week—8-week administration, then dose optimization
Part 2—40 week—extension Phase 2 is a two-part, open label, dose optimization study in 35 subjects with PKU. Part 1 conducted over a period of 16 weeks duration involves the administration of doses of pegylated AvPAL_C565SC503S once weekly for 8 weeks, followed by a period of dose optimization. Each subject's dose is adjusted to attain blood Phe concentrations below 600 The primary objective is to evaluate the safety and tolerability of multiple administration of the pegylated AvPAL_C565SC503S, and the secondary objectives are to evaluate the pegylated enzyme's effects on blood Phe concentrations, immune response, e.g., anti-AvPAL antibody titers, and steady state PK. In part 2, the subjects are administered pegylated AvPAL_C565SC503S for 40 weeks, with individualized optimized dose and frequency of administration.

Phase 3

Once the Phase 1 and 2 studies are complete, additional studies may potentially include a Phase 3 six-month double-blinded study in a greater number of subjects, with additional studies in special populations, such as, for example and not for limitation, non-PKU HPA patients, BH4-responsive PKU patients and non-BH4-responsive PHU patients.

Numerous modifications and variations in the invention as set forth in the above illustrative examples are expected to occur to those skilled in the art. Consequently only such limitations as appear in the appended claims should be placed on the invention.

What is claimed:

1. A method for purifying an *Anabaena variabilis* phenylalanine ammonia-lyase (AvPAL) variant with minimal aggregation comprising:
   (a) lysing bacterial cells containing the AvPAL variant by homogenization to generate a cell lysate;
   (b) heating the cell lysate to 65° C. for 30 to 120 minutes;
   (c) centrifuging the heated cell lysate, wherein a supernatant comprising the AvPAL variant is retained;
   (d) filtering the supernatant to remove precipitates; and
   (e) separating the AvPAL variant from contaminating proteins by sequential chromatography over an anion exchange (AIEX) column followed by a hydrophobic interaction (HIC) column, wherein the eluate from the HIC column comprises the AvPAL variant,
   wherein the AvPAL variant has the amino acid sequence of SEQ ID NO: 11.

2. The method of claim 1, further comprising:
   (f) ultrafiltering or ultrafiltering/diafiltering the eluate from the HIC column comprising the AvPAL variant;
   (g) pegylating the AvPAL variant by mixing polyethylene glycol with the AvPAL variant;
   (h) removing free polyethylene glycol from the pegylated AvPAL variant by ultrafiltation/diafiltration; and
   (i) formulating the pegylated AvPAL variant,
   wherein said AvPAL variant comprises polyethylene glycol.

3. The method of claim 2, wherein the ratio of AvPAL variant and the polyethylene glycol is about 1:3.

4. The method of claim 2, wherein the AIEX column is a Toyopearl Giga Cap Q 650M column.

5. The method of claim 2, wherein the HIC column is a Toyopearl Butyl 650M column.

6. The method of claim 2, further comprising freezing and thawing the eluate from the HIC column comprising the AvPAL variant obtained in step (e), wherein one or more polyols or sugars selected from the group consisting of glycerol, sucrose, glucose, trehalose, mannitol and sorbitol are added to the HIC column eluate prior to freezing.

7. The method of claim 6, wherein the polyol is glycerol.

8. The method of claim 7, wherein the concentration of glycerol is 10% (v/v).

9. The method of claim 6, wherein the sugar is sucrose.

10. The method of claim 9, wherein the concentration of sucrose is 10% (v/v).

11. The method of claim 6, wherein freezing the eluate from the HIC column comprising the AvPAL variant is performed in discrete temperature steps.

12. The method of claim 6, wherein thawing the eluate from the HIC column comprising the AvPAL variant is performed in discrete temperature steps.

13. The method of claim 6, wherein freezing and thawing the eluate from the HIC column comprising the AvPAL variant are performed in discrete temperature steps.

14. The method of claim 2, wherein a diafiltration buffer in step (f) comprises potassium phosphate (KPi) and one or more agents consisting of trans-cinnamic acid (t-CA) and glycerol.

15. The method of claim 14, wherein the diafiltration buffer comprises 50 mM KPi, 10 mM t-CA, 5% glycerol, pH 8.5.

16. The method of claim 2, wherein a non-ionic detergent is added to the ultrafiltered or ultrafiltered/diafiltered eluate from the HIC column comprising the AvPAL variant obtained in step (f).

17. The method of claim 16, wherein the non-ionic detergent is polysorbate 80 (PS80).

18. The method of claim 17, wherein the concentration of PS80 is 0.02%.

* * * * *

SEQUENCE LISTING

<160> NUMBER OF SEQ ID NOS: 33

<210> SEQ ID NO 1
<211> LENGTH: 1710
<212> TYPE: DNA
<213> ORGANISM: Nostoc punctiforme

<400> SEQUENCE: 1

| | | | | | |
|---|---|---|---|---|---|
| atgaatataa | catctctaca | acagaacata | acgcgttctt | ggcaaatacc | tttcactaat | 60 |
| agttcagatt | caatcgtaac | tgtaggcgat | cgcaatctga | caatcgacga | ggttgtaaat | 120 |
| gttgctcgtc | atggaacaca | ggtgcgctta | actgataatg | cagatgtcat | tcggggtgtt | 180 |
| caagcatctt | gtgattacat | taacaatgca | gtcgaaacag | cacagccaat | ttacggggtg | 240 |
| acatctggct | ttggcggtat | ggcagatgtt | gtcatctctc | gcgaacaagc | agcggaactt | 300 |
| cagactaatt | taatttggtt | tctgaaatcc | ggcgcaggaa | acaaattatc | gttagcagac | 360 |
| gtgcgtgcag | ctatgctctt | acgtgcaaat | tcacatttgt | atggtgcgtc | tggtatacga | 420 |
| ctcgaactta | ttcagcggat | tgaaactttc | tcaacgctg | gcgtgacacc | ccatgtctat | 480 |
| gagtttggct | ctatcggtgc | tagcggcgat | ttggtgccat | atcctacat | tactggggca | 540 |
| ctaatcggtc | tagatcctag | ctttacagtt | gacttcgacg | gtaaagaaat | ggatgccgtt | 600 |
| acagccttgt | ctcgtttggg | tttgccaaag | ttgcaattgc | aaccgaaaga | aggtttagca | 660 |
| atgatgaatg | gcacctcagt | catgacaggt | attgcagcta | actgtgtgta | cgatgcgaaa | 720 |
| gttttgctcg | ctctgacaat | gggtgtacac | gccttagcca | tccaaggttt | atacggaacg | 780 |
| aatcaatctt | tccacccgtt | tattcatcag | tgcaagccac | atcccggtca | actatggaca | 840 |
| gcagatcaaa | tgttttctct | gctgaaagat | tcatctttag | ttcgtgaaga | gttggatggt | 900 |
| aaacacgaat | accgtggtaa | agatctgata | caggatcgtt | attctctccg | ctgtctggca | 960 |
| cagttcatag | ggccaatcgt | tgatgggtaa | tcagagatta | ccaagcaaat | cgaggtagaa | 1020 |
| atgaactcag | tcaccgataa | cccattgatt | gatgtcgaga | accaagttag | ttatcacggc | 1080 |
| ggcaattttc | tcggacagta | tgtgggtgtg | acaatggatc | gcctacgtta | ttacataggg | 1140 |
| ctattggcca | aacacatcga | tgtgcagatt | gcacttcttg | tctcgccaga | gtttagcaac | 1200 |
| ggcttaccac | cctctttagt | tggtaatagc | gatcgcaaag | ttaatatggg | actcaaaggt | 1260 |
| ttgcaaatca | gtggaaactc | gattatgcca | ctgttgagct | tctatggaaa | ttccctagcc | 1320 |
| gatcgctttc | ctacccacgc | cgagcaattt | aatcaaaata | ttaacagcca | aggctatatt | 1380 |
| tccgcaaatt | tgacacgtcg | ttccgtagac | atatttcaga | attatatggc | gatcgcgttg | 1440 |
| atgtttggag | ttcaagctgt | tgacctccgc | acatataaga | tgaaaggtca | ttatgatgca | 1500 |
| cgtacatgcc | tctcacccaa | tactgtgcag | ttatacacag | cagtctgcga | ggtagttgga | 1560 |
| aagccactaa | cgtctgtgcg | tccatacatt | tggaacgaca | acgagcaatg | tttagatgag | 1620 |
| catattgccc | ggatttcagc | tgatatcgct | ggtggtggtt | taattgtgca | agcagttgag | 1680 |
| catatttttt | cgagcttaaa | gtcaacgtaa | | | | 1710 |

<210> SEQ ID NO 2
<211> LENGTH: 569
<212> TYPE: PRT
<213> ORGANISM: Nostoc punctiforme

<400> SEQUENCE: 2

Met Asn Ile Thr Ser Leu Gln Gln Asn Ile Thr Arg Ser Trp Gln Ile
1               5                   10                  15

-continued

```
Pro Phe Thr Asn Ser Ser Asp Ser Ile Val Thr Val Gly Asp Arg Asn
             20                  25                  30

Leu Thr Ile Asp Glu Val Val Asn Val Ala Arg His Gly Thr Gln Val
         35                  40                  45

Arg Leu Thr Asp Asn Ala Asp Val Ile Arg Gly Val Gln Ala Ser Cys
     50                  55                  60

Asp Tyr Ile Asn Asn Ala Val Glu Thr Ala Gln Pro Ile Tyr Gly Val
 65                  70                  75                  80

Thr Ser Gly Phe Gly Gly Met Ala Asp Val Val Ile Ser Arg Glu Gln
                 85                  90                  95

Ala Ala Glu Leu Gln Thr Asn Leu Ile Trp Phe Leu Lys Ser Gly Ala
             100                 105                 110

Gly Asn Lys Leu Ser Leu Ala Asp Val Arg Ala Ala Met Leu Leu Arg
         115                 120                 125

Ala Asn Ser His Leu Tyr Gly Ala Ser Gly Ile Arg Leu Glu Leu Ile
     130                 135                 140

Gln Arg Ile Glu Thr Phe Leu Asn Ala Gly Val Thr Pro His Val Tyr
145                 150                 155                 160

Glu Phe Gly Ser Ile Gly Ala Ser Gly Asp Leu Val Pro Leu Ser Tyr
                 165                 170                 175

Ile Thr Gly Ala Leu Ile Gly Leu Asp Pro Ser Phe Thr Val Asp Phe
             180                 185                 190

Asp Gly Lys Glu Met Asp Ala Val Thr Ala Leu Ser Arg Leu Gly Leu
         195                 200                 205

Pro Lys Leu Gln Leu Gln Pro Lys Glu Gly Leu Ala Met Met Asn Gly
     210                 215                 220

Thr Ser Val Met Thr Gly Ile Ala Ala Asn Cys Val Tyr Asp Ala Lys
225                 230                 235                 240

Val Leu Leu Ala Leu Thr Met Gly Val His Ala Leu Ala Ile Gln Gly
                 245                 250                 255

Leu Tyr Gly Thr Asn Gln Ser Phe His Pro Phe Ile His Gln Cys Lys
             260                 265                 270

Pro His Pro Gly Gln Leu Trp Thr Ala Asp Gln Met Phe Ser Leu Leu
         275                 280                 285

Lys Asp Ser Ser Leu Val Arg Glu Glu Leu Asp Gly Lys His Glu Tyr
     290                 295                 300

Arg Gly Lys Asp Leu Ile Gln Asp Arg Tyr Ser Leu Arg Cys Leu Ala
305                 310                 315                 320

Gln Phe Ile Gly Pro Ile Val Asp Gly Val Ser Glu Ile Thr Lys Gln
                 325                 330                 335

Ile Glu Val Glu Met Asn Ser Val Thr Asp Asn Pro Leu Ile Asp Val
             340                 345                 350

Glu Asn Gln Val Ser Tyr His Gly Gly Asn Phe Leu Gly Gln Tyr Val
         355                 360                 365

Gly Val Thr Met Asp Arg Leu Arg Tyr Tyr Ile Gly Leu Leu Ala Lys
     370                 375                 380

His Ile Asp Val Gln Ile Ala Leu Leu Val Ser Pro Glu Phe Ser Asn
385                 390                 395                 400

Gly Leu Pro Pro Ser Leu Val Gly Asn Ser Asp Arg Lys Val Asn Met
                 405                 410                 415

Gly Leu Lys Gly Leu Gln Ile Ser Gly Asn Ser Ile Met Pro Leu Leu
             420                 425                 430

Ser Phe Tyr Gly Asn Ser Leu Ala Asp Arg Phe Pro Thr His Ala Glu
```

```
                435                 440                 445
Gln Phe Asn Gln Asn Ile Asn Ser Gln Gly Tyr Ile Ser Ala Asn Leu
    450                 455                 460

Thr Arg Arg Ser Val Asp Ile Phe Gln Asn Tyr Met Ala Ile Ala Leu
465                 470                 475                 480

Met Phe Gly Val Gln Ala Val Asp Leu Arg Thr Tyr Lys Met Lys Gly
                485                 490                 495

His Tyr Asp Ala Arg Thr Cys Leu Ser Pro Asn Thr Val Gln Leu Tyr
            500                 505                 510

Thr Ala Val Cys Glu Val Val Gly Lys Pro Leu Thr Ser Val Arg Pro
        515                 520                 525

Tyr Ile Trp Asn Asp Asn Glu Gln Cys Leu Asp Glu His Ile Ala Arg
    530                 535                 540

Ile Ser Ala Asp Ile Ala Gly Gly Gly Leu Ile Val Gln Ala Val Glu
545                 550                 555                 560

His Ile Phe Ser Ser Leu Lys Ser Thr
                565

<210> SEQ ID NO 3
<211> LENGTH: 1704
<212> TYPE: DNA
<213> ORGANISM: Anabaena variabilis

<400> SEQUENCE: 3
atgaagacac tatctcaagc acaaagcaaa acctcatctc aacaattttc ttttactgga      60
aattcttctg ccaatgtaat tattggtaat cagaaactca caatcaatga tgttgcaagg     120
gtagcgcgta atggcacctt agtgtcttta accaataaca ctgatatttt gcagggtatt     180
caggcatctt gtgattacat taataatgct gttgaatctg gggaaccaat ttatggagtg     240
acatctggtt ttggcggtat ggccaatgtt gccatatccc gtgaacaagc atctgaactc     300
caaaccaact tagtttggtt cctgaaaaca ggtgcaggga caaaattacc cttggcggat     360
gtgcgcgcag ctatgctctt gcgtgcaaac tctcatatgc gcggtgcatc tggcatcaga     420
ttagaactta tcaagcgtat ggagattttc cttaacgctg tgtcacacc atatgtgtat     480 gagtttggtt caattggtgc aagtggtgat ttagtgccac tatcctacat tactggttca     540
ctgataggct agatcccag ttttaaggtt gacttcaacg gtaaagaaat ggatgcgcca     600
acagctctac gtcaactgaa tttgtcaccc ttgacattgt tgccgaagga aggcttggcg     660
atgatgaacg gcacttcagt catgacaggt attgcagcaa actgcgtcta cgatactcaa     720
attttaactg cgatcgctat gggcgttcac gctctagata tccaagcttt aaacggaacc     780
aatcaatcat ccatccatt tatccataat tccaaaccac atcctggtca attatgggca     840
gcagatcaga tgatttcttt gttagccaat tcccagttag ttcgtgatga gttagatggt     900
aaacacgatt atcgtgatca cgagttgatt caagatcgtt actcactccg atgccttccc     960
cagtatttgg ggccaatcgt tgatggaatt tcccagattg ccaaacaaat tgaaatcgaa    1020
atcaactcag tcaccgataa cccactaatt gatgttgata ccaagctag ctatcatgga    1080 ggaaatttcc tcggacagta cgtgggtatg gaatggatc acctgcgtta ctatattggg    1140
ttattggcta aacacctaga tgtgcagatt gccctcctcg cctcaccaga gtttagcaat    1200
ggactaccac catctttatt aggcaaccga gaacgtaaag tcaatatggg actcaaaggt    1260 ctgcaaaatat gcgtaactc aattatgcca ctgttgacct tctatggaaa ttccatcgcc    1320
gatcgctttc ctaccccatgc agaacaattt aatcagaaca tcaacagtca aggatacact    1380
```

```
tcagcgactc tagcccgccg ttctgtggat atcttccaga attatgtggc gatcgctctg    1440
atgtttggag tccaagctgt tgacctccgc acatataaaa agactggtca ttacgatgca    1500
cgcgcctgtc tatcacctgc aactgagcgc ttatattcag cagtccgcca cgtagttgga    1560
caaaaaccaa cttcagatcg cccatatatt tggaatgata atgagcaagg actggatgag    1620
catattgccc ggatttctgc tgatatcgct gctggtggtg tgattgtgca agcagttcaa    1680
gatatcttac cctgcttgca ttaa                                           1704
```

<210> SEQ ID NO 4
<211> LENGTH: 567
<212> TYPE: PRT
<213> ORGANISM: Anabaena variabilis

<400> SEQUENCE: 4

```
Met Lys Thr Leu Ser Gln Ala Gln Ser Lys Thr Ser Ser Gln Gln Phe
  1               5                  10                  15

Ser Phe Thr Gly Asn Ser Ser Ala Asn Val Ile Ile Gly Asn Gln Lys
                 20                  25                  30

Leu Thr Ile Asn Asp Val Ala Arg Val Ala Arg Asn Gly Thr Leu Val
             35                  40                  45

Ser Leu Thr Asn Asn Thr Asp Ile Leu Gln Gly Ile Gln Ala Ser Cys
         50                  55                  60

Asp Tyr Ile Asn Asn Ala Val Glu Ser Gly Glu Pro Ile Tyr Gly Val
 65                  70                  75                  80

Thr Ser Gly Phe Gly Gly Met Ala Asn Val Ala Ile Ser Arg Glu Gln
                 85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
```

```
            305                 310                 315                 320

Gln Tyr Leu Gly Pro Ile Val Asp Gly Ile Ser Gln Ile Ala Lys Gln
                    325                 330                 335

Ile Glu Ile Glu Ile Asn Ser Val Thr Asp Asn Pro Leu Ile Asp Val
                    340                 345                 350

Asp Asn Gln Ala Ser Tyr His Gly Asn Phe Leu Gly Gln Tyr Val
                    355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
    385                 390                 395                 400

Gly Leu Pro Pro Ser Leu Leu Gly Asn Arg Glu Arg Lys Val Asn Met
                    405                 410                 415

Gly Leu Lys Gly Leu Gln Ile Cys Gly Asn Ser Ile Met Pro Leu Leu
                    420                 425                 430

Thr Phe Tyr Gly Asn Ser Ile Ala Asp Arg Phe Pro Thr His Ala Glu
                    435                 440                 445

Gln Phe Asn Gln Asn Ile Asn Ser Gln Gly Tyr Thr Ser Ala Thr Leu
                    450                 455                 460

Ala Arg Arg Ser Val Asp Ile Phe Gln Asn Tyr Val Ala Ile Ala Leu
    465                 470                 475                 480

Met Phe Gly Val Gln Ala Val Asp Leu Arg Thr Tyr Lys Lys Thr Gly
                    485                 490                 495

His Tyr Asp Ala Arg Ala Cys Leu Ser Pro Ala Thr Glu Arg Leu Tyr
                    500                 505                 510

Ser Ala Val Arg His Val Val Gly Gln Lys Pro Thr Ser Asp Arg Pro
                    515                 520                 525

Tyr Ile Trp Asn Asp Asn Glu Gln Gly Leu Asp Glu His Ile Ala Arg
                    530                 535                 540

Ile Ser Ala Asp Ile Ala Ala Gly Gly Val Ile Val Gln Ala Val Gln
    545                 550                 555                 560

Asp Ile Leu Pro Cys Leu His
                    565

<210> SEQ ID NO 5
<211> LENGTH: 523
<212> TYPE: PRT
<213> ORGANISM: Streptomyces maritimus

<400> SEQUENCE: 5

Met Thr Phe Val Ile Glu Leu Asp Met Asn Val Thr Leu Asp Gln Leu
1               5                   10                  15

Glu Asp Ala Ala Arg Gln Arg Thr Pro Val Glu Leu Ser Ala Pro Val
                20                  25                  30

Arg Ser Arg Val Arg Ala Ser Arg Asp Val Leu Val Lys Phe Val Gln
            35                  40                  45

Asp Glu Arg Val Ile Tyr Gly Val Asn Thr Ser Met Gly Gly Phe Val
        50                  55                  60

Asp His Leu Val Pro Val Ser Gln Ala Arg Gln Leu Gln Glu Asn Leu
65                  70                  75                  80

Ile Asn Ala Val Ala Thr Asn Val Gly Ala Tyr Leu Asp Asp Thr Thr
                85                  90                  95

Ala Arg Thr Ile Met Leu Ser Arg Ile Val Ser Leu Ala Arg Gly Asn
                100                 105                 110
```

```
Ser Ala Ile Thr Pro Ala Asn Leu Asp Lys Leu Val Ala Val Leu Asn
            115                 120                 125

Ala Gly Ile Val Pro Cys Ile Pro Glu Lys Gly Ser Leu Gly Thr Ser
130                 135                 140

Gly Asp Leu Gly Pro Leu Ala Ile Ala Leu Val Cys Ala Gly Gln
145                 150                 155                 160

Trp Lys Ala Arg Tyr Asn Gly Gln Ile Met Pro Gly Arg Gln Ala Leu
                165                 170                 175

Ser Glu Ala Gly Val Glu Pro Met Glu Leu Ser Tyr Lys Asp Gly Leu
            180                 185                 190

Ala Leu Ile Asn Gly Thr Ser Gly Met Val Gly Leu Gly Thr Met Val
            195                 200                 205

Leu Gln Ala Ala Arg Arg Leu Val Asp Arg Tyr Leu Gln Val Ser Ala
210                 215                 220

Leu Ser Val Glu Gly Leu Ala Gly Met Thr Lys Pro Phe Asp Pro Arg
225                 230                 235                 240

Val His Gly Val Lys Pro His Arg Gly Gln Arg Gln Val Ala Ser Arg
                245                 250                 255

Leu Trp Glu Gly Leu Ala Asp Ser His Leu Ala Val Asn Glu Leu Asp
            260                 265                 270

Thr Glu Gln Thr Leu Ala Gly Glu Met Gly Thr Val Ala Lys Ala Gly
            275                 280                 285

Ser Leu Ala Ile Glu Asp Ala Tyr Ser Ile Arg Cys Thr Pro Gln Ile
            290                 295                 300

Leu Gly Pro Val Asp Val Leu Asp Arg Ile Gly Ala Thr Leu Gln
305                 310                 315                 320

Asp Glu Leu Asn Ser Ser Asn Asp Asn Pro Ile Val Leu Pro Glu Glu
                325                 330                 335

Ala Glu Val Phe His Asn Gly His Phe His Gly Gln Tyr Val Ala Met
                340                 345                 350

Ala Met Asp His Leu Asn Met Ala Leu Ala Thr Val Thr Asn Leu Ala
            355                 360                 365

Asn Arg Arg Val Asp Arg Phe Leu Asp Lys Ser Asn Ser Asn Gly Leu
370                 375                 380

Pro Ala Phe Leu Cys Arg Glu Asp Pro Gly Leu Arg Leu Gly Leu Met
385                 390                 395                 400

Gly Gly Gln Phe Met Thr Ala Ser Ile Thr Ala Glu Thr Arg Thr Leu
                405                 410                 415

Thr Ile Pro Met Ser Val Gln Ser Leu Thr Ser Thr Ala Asp Phe Gln
                420                 425                 430

Asp Ile Val Ser Phe Gly Phe Val Ala Ala Arg Arg Ala Arg Glu Val
            435                 440                 445

Leu Thr Asn Ala Ala Tyr Val Val Ala Phe Glu Leu Leu Cys Ala Cys
450                 455                 460

Gln Ala Val Asp Ile Arg Gly Ala Asp Lys Leu Ser Ser Phe Thr Arg
465                 470                 475                 480

Pro Leu Tyr Glu Arg Thr Arg Lys Ile Val Pro Phe Phe Asp Arg Asp
                485                 490                 495

Glu Thr Ile Thr Asp Tyr Val Glu Lys Leu Ala Ala Asp Leu Ile Ala
            500                 505                 510

Gly Glu Pro Val Asp Ala Ala Val Ala Ala His
            515                 520
```

```
<210> SEQ ID NO 6
<211> LENGTH: 510
<212> TYPE: PRT
<213> ORGANISM: Pseudomonas putida

<400> SEQUENCE: 6
```

| | | | | | | | | | | | | | | |
|---|---|---|---|---|---|---|---|---|---|---|---|---|---|---|
| Met | Thr | Glu | Leu | Thr | Leu | Lys | Pro | Gly | Thr | Leu | Thr | Leu | Ala | Gln | Leu |
| 1 | | | | 5 | | | | | 10 | | | | | 15 | |
| Arg | Ala | Ile | His | Ala | Ala | Pro | Val | Arg | Leu | Gln | Leu | Asp | Ala | Ser | Ala |
| | | | 20 | | | | | 25 | | | | | 30 | | |
| Ala | Pro | Ala | Ile | Asp | Ala | Ser | Val | Ala | Cys | Val | Glu | Gln | Ile | Ile | Ala |
| | | 35 | | | | | 40 | | | | | 45 | | | |
| Glu | Asp | Arg | Thr | Ala | Tyr | Gly | Ile | Asn | Thr | Gly | Phe | Gly | Leu | Leu | Ala |
| | 50 | | | | | 55 | | | | | 60 | | | | |
| Ser | Thr | Arg | Ile | Ala | Ser | His | Asp | Leu | Glu | Asn | Leu | Gln | Arg | Ser | Leu |
| 65 | | | | | 70 | | | | | 75 | | | | | 80 |
| Val | Leu | Ser | His | Ala | Ala | Gly | Ile | Gly | Ala | Pro | Leu | Asp | Asp | Asp | Leu |
| | | | | 85 | | | | | 90 | | | | | 95 | |
| Val | Arg | Leu | Ile | Met | Val | Leu | Lys | Ile | Asn | Ser | Leu | Ser | Arg | Gly | Phe |
| | | | 100 | | | | | 105 | | | | | 110 | | |
| Ser | Gly | Ile | Arg | Arg | Lys | Val | Ile | Asp | Ala | Leu | Ile | Ala | Leu | Val | Asn |
| | | 115 | | | | | 120 | | | | | 125 | | | |
| Ala | Glu | Val | Tyr | Pro | His | Ile | Pro | Leu | Lys | Gly | Ser | Val | Gly | Ala | Ser |
| | 130 | | | | | 135 | | | | | 140 | | | | |
| Gly | Asp | Leu | Ala | Pro | Leu | Ala | Thr | Met | Ser | Leu | Val | Leu | Leu | Gly | Glu |
| 145 | | | | | 150 | | | | | 155 | | | | | 160 |
| Gly | Lys | Ala | Arg | Tyr | Lys | Gly | Gln | Trp | Leu | Ser | Ala | Thr | Glu | Ala | Leu |
| | | | | 165 | | | | | 170 | | | | | 175 | |
| Ala | Val | Ala | Gly | Leu | Glu | Pro | Leu | Thr | Leu | Ala | Ala | Lys | Glu | Gly | Leu |
| | | | 180 | | | | | 185 | | | | | 190 | | |
| Ala | Leu | Leu | Asn | Gly | Thr | Gln | Ala | Ser | Thr | Ala | Tyr | Ala | Leu | Arg | Gly |
| | | 195 | | | | | 200 | | | | | 205 | | | |
| Leu | Phe | Tyr | Ala | Glu | Asp | Leu | Tyr | Ala | Ala | Ile | Ala | Cys | Gly | Gly |
| | 210 | | | | | 215 | | | | | 220 | | | | |
| Leu | Ser | Val | Glu | Ala | Val | Leu | Gly | Ser | Arg | Ser | Pro | Phe | Asp | Ala | Arg |
| 225 | | | | | 230 | | | | | 235 | | | | | 240 |
| Ile | His | Glu | Ala | Arg | Gly | Gln | Arg | Gly | Gln | Ile | Asp | Thr | Ala | Ala | Cys |
| | | | | 245 | | | | | 250 | | | | | 255 | |
| Phe | Arg | Asp | Leu | Leu | Gly | Asp | Ser | Ser | Glu | Val | Ser | Leu | Ser | His | Lys |
| | | | 260 | | | | | 265 | | | | | 270 | | |
| Asn | Cys | Asp | Lys | Val | Gln | Asp | Pro | Tyr | Ser | Leu | Arg | Cys | Gln | Pro | Gln |
| | | 275 | | | | | 280 | | | | | 285 | | | |
| Val | Met | Gly | Ala | Cys | Leu | Thr | Gln | Leu | Arg | Gln | Ala | Ala | Glu | Val | Leu |
| | 290 | | | | | 295 | | | | | 300 | | | | |
| Gly | Ile | Glu | Ala | Asn | Ala | Val | Ser | Asp | Asn | Pro | Leu | Val | Phe | Ala | Ala |
| 305 | | | | | 310 | | | | | 315 | | | | | 320 |
| Glu | Gly | Asp | Val | Ile | Ser | Gly | Gly | Asn | Phe | His | Ala | Glu | Pro | Val | Ala |
| | | | | 325 | | | | | 330 | | | | | 335 | |
| Met | Ala | Ala | Asp | Asn | Leu | Ala | Leu | Ala | Ile | Ala | Glu | Ile | Gly | Ser | Leu |
| | | | 340 | | | | | 345 | | | | | 350 | | |
| Ser | Glu | Arg | Arg | Ile | Ser | Leu | Met | Met | Asp | Lys | His | Met | Ser | Gln | Leu |
| | | 355 | | | | | 360 | | | | | 365 | | | |
| Pro | Pro | Phe | Leu | Val | Glu | Asn | Gly | Gly | Val | Asn | Ser | Gly | Phe | Met | Ile |
| | 370 | | | | | 375 | | | | | 380 | | | | |

-continued

```
Ala Gln Val Thr Ala Ala Leu Ala Ser Glu Asn Lys Ala Leu Ser
385                 390                 395                 400

His Pro His Ser Val Asp Ser Leu Pro Thr Ser Ala Asn Gln Glu Asp
                405                 410                 415

His Val Ser Met Ala Pro Ala Ala Gly Lys Arg Leu Trp Glu Met Ala
            420                 425                 430

Glu Asn Thr Arg Gly Val Pro Ala Ile Glu Trp Leu Gly Ala Cys Gln
                435                 440                 445

Gly Leu Asp Leu Arg Lys Gly Leu Lys Thr Ser Ala Lys Leu Glu Lys
        450                 455                 460

Ala Arg Gln Ala Leu Arg Ser Glu Val Ala His Tyr Asp Arg Asp Arg
465                 470                 475                 480

Phe Phe Ala Pro Asp Ile Glu Lys Ala Val Glu Leu Leu Ala Lys Gly
                485                 490                 495

Ser Leu Thr Gly Leu Leu Pro Ala Gly Val Leu Pro Ser Leu
                500                 505                 510

<210> SEQ ID NO 7
<211> LENGTH: 567
<212> TYPE: PRT
<213> ORGANISM: Artificial Sequence
<220> FEATURE:
<223> OTHER INFORMATION: Anabaena variabilis PAL
<220> FEATURE:
<223> OTHER INFORMATION: Cysteine to serine substitution at position 64

<400> SEQUENCE: 7

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Ser
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
```

```
            225                 230                 235                 240
    Ile Leu Thr Ala Ile Ala Met Gly Val His Ala Leu Asp Ile Gln Ala
                    245                 250                 255
    Leu Asn Gly Thr Asn Gln Ser Phe His Pro Phe Ile His Asn Ser Lys
                260                 265                 270
    Pro His Pro Gly Gln Leu Trp Ala Asp Gln Met Ile Ser Leu Leu
            275                 280                 285
    Ala Asn Ser Gln Leu Val Arg Asp Glu Leu Asp Gly Lys His Asp Tyr
            290                 295                 300
    Arg Asp His Glu Leu Ile Gln Asp Arg Tyr Ser Leu Arg Cys Leu Pro
    305                 310                 315                 320
    Gln Tyr Leu Gly Pro Ile Val Asp Gly Ile Ser Gln Ile Ala Lys Gln
                    325                 330                 335
    Ile Glu Ile Glu Ile Asn Ser Val Thr Asp Asn Pro Leu Ile Asp Val
                340                 345                 350
    Asp Asn Gln Ala Ser Tyr His Gly Gly Asn Phe Leu Gly Gln Tyr Val
                355                 360                 365
    Gly Met Gly Met Asp His Leu Arg Tyr Tyr Ile Gly Leu Leu Ala Lys
            370                 375                 380
    His Leu Asp Val Gln Ile Ala Leu Leu Ala Ser Pro Glu Phe Ser Asn
    385                 390                 395                 400
    Gly Leu Pro Pro Ser Leu Leu Gly Asn Arg Glu Arg Lys Val Asn Met
                    405                 410                 415
    Gly Leu Lys Gly Leu Gln Ile Cys Gly Asn Ser Ile Met Pro Leu Leu
                420                 425                 430
    Thr Phe Tyr Gly Asn Ser Ile Ala Asp Arg Phe Pro Thr His Ala Glu
            435                 440                 445
    Gln Phe Asn Gln Asn Ile Asn Ser Gln Gly Tyr Thr Ser Ala Thr Leu
            450                 455                 460
    Ala Arg Arg Ser Val Asp Ile Phe Gln Asn Tyr Val Ala Ile Ala Leu
    465                 470                 475                 480
    Met Phe Gly Val Gln Ala Val Asp Leu Arg Thr Tyr Lys Lys Thr Gly
                    485                 490                 495
    His Tyr Asp Ala Arg Ala Cys Leu Ser Pro Ala Thr Glu Arg Leu Tyr
                500                 505                 510
    Ser Ala Val Arg His Val Val Gly Gln Lys Pro Thr Ser Asp Arg Pro
            515                 520                 525
    Tyr Ile Trp Asn Asp Asn Glu Gln Gly Leu Asp Glu His Ile Ala Arg
            530                 535                 540
    Ile Ser Ala Asp Ile Ala Ala Gly Gly Val Ile Val Gln Ala Val Gln
    545                 550                 555                 560
    Asp Ile Leu Pro Cys Leu His
                    565

<210> SEQ ID NO 8
<211> LENGTH: 567
<212> TYPE: PRT
<213> ORGANISM: Artificial Sequence
<220> FEATURE:
<223> OTHER INFORMATION: Anabaena variabilis PAL
<220> FEATURE:
<223> OTHER INFORMATION: Cysteine to serine substitution at position 318

<400> SEQUENCE: 8

Met Lys Thr Leu Ser Gln Ala Gln Ser Lys Thr Ser Ser Gln Gln Phe
1               5                   10                  15
```

```
Ser Phe Thr Gly Asn Ser Ser Ala Asn Val Ile Ile Gly Asn Gln Lys
             20                  25                  30

Leu Thr Ile Asn Asp Val Ala Arg Val Ala Arg Asn Gly Thr Leu Val
             35                  40                  45

Ser Leu Thr Asn Asn Thr Asp Ile Leu Gln Gly Ile Gln Ala Ser Cys
 50                  55                  60

Asp Tyr Ile Asn Asn Ala Val Glu Ser Gly Glu Pro Ile Tyr Gly Val
 65                  70                  75                  80

Thr Ser Gly Phe Gly Gly Met Ala Asn Val Ala Ile Ser Arg Glu Gln
                 85                  90                  95

Ala Ser Glu Leu Gln Thr Asn Leu Val Trp Phe Leu Lys Thr Gly Ala
             100                 105                 110

Gly Asn Lys Leu Pro Leu Ala Asp Val Arg Ala Ala Met Leu Leu Arg
             115                 120                 125

Ala Asn Ser His Met Arg Gly Ala Ser Gly Ile Arg Leu Glu Leu Ile
 130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                 165                 170                 175

Ile Thr Gly Ser Leu Ile Gly Leu Asp Pro Ser Phe Lys Val Asp Phe
             180                 185                 190

Asn Gly Lys Glu Met Asp Ala Pro Thr Ala Leu Arg Gln Leu Asn Leu
             195                 200                 205

Ser Pro Leu Thr Leu Leu Pro Lys Glu Gly Leu Ala Met Met Asn Gly
 210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                 245                 250                 255

Leu Asn Gly Thr Asn Gln Ser Phe His Pro Phe Ile His Asn Ser Lys
             260                 265                 270

Pro His Pro Gly Gln Leu Trp Ala Ala Asp Gln Met Ile Ser Leu Leu
             275                 280                 285

Ala Asn Ser Gln Leu Val Arg Asp Glu Leu Asp Gly Lys His Asp Tyr
 290                 295                 300

Arg Asp His Glu Leu Ile Gln Asp Arg Tyr Ser Leu Arg Ser Leu Pro
305                 310                 315                 320

Gln Tyr Leu Gly Pro Ile Val Asp Gly Ile Ser Gln Ile Ala Lys Gln
                 325                 330                 335

Ile Glu Ile Glu Ile Asn Ser Val Thr Asp Asn Pro Leu Ile Asp Val
             340                 345                 350

Asp Asn Gln Ala Ser Tyr His Gly Gly Asn Phe Leu Gly Gln Tyr Val
 355                 360                 365

Gly Met Gly Met Asp His Leu Arg Tyr Tyr Ile Gly Leu Leu Ala Lys
             370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                 405                 410                 415

Gly Leu Lys Gly Leu Gln Ile Cys Gly Asn Ser Ile Met Pro Leu Leu
             420                 425                 430
```

Thr Phe Tyr Gly Asn Ser Ile Ala Asp Arg Phe Pro Thr His Ala Glu
                435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
                500                 505                 510

Ser Ala Val Arg His Val Val Gly Gln Lys Pro Thr Ser Asp Arg Pro
                515                 520                 525

Tyr Ile Trp Asn Asp Asn Glu Gln Gly Leu Asp Glu His Ile Ala Arg
                530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 9
<211> LENGTH: 567
<212> TYPE: PRT
<213> ORGANISM: Artificial Sequence
<220> FEATURE:
<223> OTHER INFORMATION: Anabaena variabilis PAL
<220> FEATURE:
<223> OTHER INFORMATION: Cysteine to serine substitution at position 503

<400> SEQUENCE: 9

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
                35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
                115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
                195                 200                 205

Ser Pro Leu Thr Leu Leu Pro Lys Glu Gly Leu Ala Met Met Asn Gly

```
            210                 215                 220
Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
                260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
        290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
        370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
        450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
        530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 10
<211> LENGTH: 567
<212> TYPE: PRT
<213> ORGANISM: Artificial Sequence
<220> FEATURE:
<223> OTHER INFORMATION: Anabaena variabilis PAL
<220> FEATURE:
<223> OTHER INFORMATION: Cysteine to serine substitution at position 565

<400> SEQUENCE: 10
```

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
            195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
            245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
        290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
            370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415
```

```
Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
            515                 520                 525

Tyr Ile Trp Asn Asp Asn Glu Gln Gly Leu Asp Glu His Ile Ala Arg
            530                 535                 540

Ile Ser Ala Asp Ile Ala Ala Gly Gly Val Ile Val Gln Ala Val Gln
545                 550                 555                 560

Asp Ile Leu Pro Ser Leu His
                565

<210> SEQ ID NO 11
<211> LENGTH: 567
<212> TYPE: PRT
<213> ORGANISM: Artificial Sequence
<220> FEATURE:
<223> OTHER INFORMATION: Anabaena variabilis PAL
<220> FEATURE:
<223> OTHER INFORMATION: Cysteine to serine substitutions at positions
      565 and 503

<400> SEQUENCE: 11

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190
```

```
Asn Gly Lys Glu Met Asp Ala Pro Thr Ala Leu Arg Gln Leu Asn Leu
        195                 200                 205

Ser Pro Leu Thr Leu Leu Pro Lys Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Ser Leu His
                565
```

<210> SEQ ID NO 12
<211> LENGTH: 38
<212> TYPE: DNA
<213> ORGANISM: Artificial Sequence
<220> FEATURE:
<223> OTHER INFORMATION: Nostoc punctiforme PAL primer 1 (forward)

```
<400> SEQUENCE: 12
cactgtcata tgaatataac atctctacaa cagaacat                              38

<210> SEQ ID NO 13
<211> LENGTH: 45
<212> TYPE: DNA
<213> ORGANISM: Artificial Sequence
<220> FEATURE:
<223> OTHER INFORMATION: Nostoc punctiforme PAL primer 2 (reverse)

<400> SEQUENCE: 13
gacagtggcg gccgctcacg ttgactttaa gctcgaaaaa atatg                      45

<210> SEQ ID NO 14
<211> LENGTH: 38
<212> TYPE: DNA
<213> ORGANISM: Artificial Sequence
<220> FEATURE:
<223> OTHER INFORMATION: Anabaena variabilis PAL primer 1 (forward, N-
      terminal fragment)

<400> SEQUENCE: 14
cactgtgcta gcatgaagac actatctcaa gcacaaag                              38

<210> SEQ ID NO 15
<211> LENGTH: 49
<212> TYPE: DNA
<213> ORGANISM: Artificial Sequence
<220> FEATURE:
<223> OTHER INFORMATION: Anabaena variabilis PAL primer 2 (reverse, N-
      terminal fragment)

<400> SEQUENCE: 15
ggaaatttcc tccatgatag ctggcttggt tatcaacatc aattagtgg                  49

<210> SEQ ID NO 16
<211> LENGTH: 49
<212> TYPE: DNA
<213> ORGANISM: Artificial Sequence
<220> FEATURE:
<223> OTHER INFORMATION: Anabaena variabilis PAL primer 3 (forward,
      C-terminal fragment)

<400> SEQUENCE: 16
ccactaattg atgttgataa ccaagccagc tatcatggag gaaatttcc                  49

<210> SEQ ID NO 17
<211> LENGTH: 41
<212> TYPE: DNA
<213> ORGANISM: Artificial Sequence
<220> FEATURE:
<223> OTHER INFORMATION: Anabaena variabilis PAL primer 4 (reverse,
      C-terminal fragment)

<400> SEQUENCE: 17
cactgtgcgg ccgcttaatg caagcagggt aagatatctt g                          41

<210> SEQ ID NO 18
<211> LENGTH: 35
<212> TYPE: DNA
<213> ORGANISM: Artificial Sequence
<220> FEATURE:
<223> OTHER INFORMATION: Anabaena variabilis PAL forward primer

<400> SEQUENCE: 18
```

```
cactgtcata tgaagacact atctcaagca caaag                                35
```

<210> SEQ ID NO 19
<211> LENGTH: 36
<212> TYPE: DNA
<213> ORGANISM: Artificial Sequence
<220> FEATURE:
<223> OTHER INFORMATION: Anabaena variabilis PAL reverse primer

<400> SEQUENCE: 19

```
cactgtctcg agatgcaagc agggtaagat atcttg                               36
```

<210> SEQ ID NO 20
<211> LENGTH: 38
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site (forward, N-terminal)

<400> SEQUENCE: 20

```
cactgtgcta gcatgaagac actatctcaa gcacaaag                             38
```

<210> SEQ ID NO 21
<211> LENGTH: 49
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site  (reverse, N-terminal)

<400> SEQUENCE: 21

```
ggaaatttcc tccatgatag ctggcttggt tatcaacatc aattagtgg                 49
```

<210> SEQ ID NO 22
<211> LENGTH: 49
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site (forward, C-terminal
      fragment)

<400> SEQUENCE: 22

```
ccactaattg atgttgataa ccaagccagc tatcatggag gaaatttcc                 49
```

<210> SEQ ID NO 23
<211> LENGTH: 41
<212> TYPE: DNA
<213> ORGANISM: Artificial Sequence
<220> FEATURE:
<223> OTHER INFORMATION: Anabaena variabilis PAL primer to create 5'
      NheI site and delete internal NheI site  (reverse, C-terminal
      fragment)

<400> SEQUENCE: 23

```
acagtggcgg ccgcttaatg caagcagggt aagatatctt g                         41
```

<210> SEQ ID NO 24
<211> LENGTH: 38
<212> TYPE: DNA
<213> ORGANISM: Artificial Sequence
<220> FEATURE:
<223> OTHER INFORMATION: Anabaena variabilis PAL primer to create 5'
      NheI site and 3' SmaI site (forward)

<400> SEQUENCE: 24
cactgtgaat tcatgaagac actatctcaa gcacaaag        38

<210> SEQ ID NO 25
<211> LENGTH: 37
<212> TYPE: DNA
<213> ORGANISM: Artificial Sequence
<220> FEATURE:
<223> OTHER INFORMATION: Anabaena variabilis PAL primer to create 5'
      NheI site and 3' SmaI site (reverse)

<400> SEQUENCE: 25
cactgtcccg ggttaatgca agcagggtaa gatatct        37

<210> SEQ ID NO 26
<211> LENGTH: 41
<212> TYPE: DNA
<213> ORGANISM: Artificial Sequence
<220> FEATURE:
<223> OTHER INFORMATION: Anabaena variabilis PAL primer to create
      cysteine to serine substitution at position 503 (forward)

<400> SEQUENCE: 26
gtcattacga tgcacgcgcc tctctatcac ctgcaactga g        41

<210> SEQ ID NO 27
<211> LENGTH: 41
<212> TYPE: DNA
<213> ORGANISM: Artificial Sequence
<220> FEATURE:
<223> OTHER INFORMATION: Anabaena variabilis PAL primer to create
      cysteine to serine substitution at position 503 (reverse)

<400> SEQUENCE: 27
ctcagttgca ggtgatagag aggcgcgtgc atcgtaatga c        41

<210> SEQ ID NO 28
<211> LENGTH: 42
<212> TYPE: DNA
<213> ORGANISM: Artificial Sequence
<220> FEATURE:
<223> OTHER INFORMATION: Anabaena variabilis PAL primer to create
      cysteine to serine substitution at position 565 (forward)

<400> SEQUENCE: 28
cagttcaaga tatcttaccc tccttgcatt aacccgggct gc        42

<210> SEQ ID NO 29
<211> LENGTH: 42
<212> TYPE: DNA
<213> ORGANISM: Artificial Sequence
<220> FEATURE:
<223> OTHER INFORMATION: Anabaena variabilis PAL primer to create
      cysteine to serine substitution at position 565 (reverse)

<400> SEQUENCE: 29
gcagcccggg ttaatgcaag gagggtaaga tatcttgaac tg        42

<210> SEQ ID NO 30
<211> LENGTH: 44
<212> TYPE: DNA
<213> ORGANISM: Artificial Sequence
<220> FEATURE:
<223> OTHER INFORMATION: Anabaena variabilis PAL primer to create
      cysteine to serine substitution at position 64 (forward)

<400> SEQUENCE: 30
gcagggtatt caggcatctt ctgattacat taataatgct gttg        44

```
<210> SEQ ID NO 31
<211> LENGTH: 44
<212> TYPE: DNA
<213> ORGANISM: Artificial Sequence
<220> FEATURE:
<223> OTHER INFORMATION: Anabaena variabilis PAL primer to create
      cysteine to serine substitution at position 64 (reverse)

<400> SEQUENCE: 31
caacagcatt attaatgtaa tcagaagatg cctgaatacc ctgc            44

<210> SEQ ID NO 32
<211> LENGTH: 43
<212> TYPE: DNA
<213> ORGANISM: Artificial Sequence
<220> FEATURE:
<223> OTHER INFORMATION: Anabaena variabilis PAL primer to create
      cysteine to serine substitution at position 318 (forward)

<400> SEQUENCE: 32
caagatcgtt actcactccg atcccttccc cagtatttgg ggc             43

<210> SEQ ID NO 33
<211> LENGTH: 43
<212> TYPE: DNA
<213> ORGANISM: Artificial Sequence
<220> FEATURE:
<223> OTHER INFORMATION: Anabaena variabilis PAL primer to create
      cysteine to serine substitution at position 318 (reverse)

<400> SEQUENCE: 33
gccccaaata ctggggaagg gatcggagtg agtaacgatc ttg             43
```